United States Patent
Hu

(10) Patent No.: US 11,872,194 B2
(45) Date of Patent: Jan. 16, 2024

(54) METHODS AND COMPOSITIONS RELATED TO A TISSUE FACTOR-TARGETING IGG3 IMMUNOCONJUGATES

(71) Applicant: Ohio State Innovation Foundation, Columbus, OH (US)

(72) Inventor: Zhiwei Hu, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 991 days.

(21) Appl. No.: 16/494,177

(22) PCT Filed: Mar. 14, 2018

(86) PCT No.: PCT/US2018/022443
§ 371 (c)(1),
(2) Date: Sep. 13, 2019

(87) PCT Pub. No.: WO2018/170134
PCT Pub. Date: Sep. 20, 2018

(65) Prior Publication Data
US 2020/0085922 A1 Mar. 19, 2020

Related U.S. Application Data

(60) Provisional application No. 62/471,045, filed on Mar. 14, 2017, provisional application No. 62/576,278, filed on Oct. 24, 2017, provisional application No. 62/623,269, filed on Jan. 29, 2018.

(51) Int. Cl.
*C07K 14/745* (2006.01)
*A61K 38/48* (2006.01)
*C07K 16/36* (2006.01)

(52) U.S. Cl.
CPC .......... *A61K 38/4846* (2013.01); *C07K 16/36* (2013.01); *C07K 2317/72* (2013.01); *C07K 2317/73* (2013.01); *C07K 2317/94* (2013.01); *C12Y 304/21021* (2013.01)

(58) Field of Classification Search
None
See application file for complete search history.

(56) References Cited

U.S. PATENT DOCUMENTS

| | | |
|---|---|---|
| 4,649,151 A | 3/1987 | Dougherty et al. |
| 4,866,168 A | 9/1989 | Dougherty et al. |
| 4,883,790 A | 11/1989 | Levy et al. |
| 4,920,143 A | 4/1990 | Levy et al. |
| 4,968,715 A | 11/1990 | Dougherty et al. |
| 5,002,962 A | 3/1991 | Pandey et al. |
| 5,028,621 A | 7/1991 | Dougherty et al. |
| 5,079,262 A | 1/1992 | Kennedy et al. |
| 5,093,349 A | 3/1992 | Pandey et al. |
| 5,095,030 A | 3/1992 | Levy et al. |
| 5,166,197 A | 11/1992 | Kenney et al. |
| 5,171,741 A | 12/1992 | Dougherty et al. |
| 5,171,749 A | 12/1992 | Levy et al. |
| 5,173,504 A | 12/1992 | Dougherty et al. |
| 5,190,966 A | 3/1993 | Dougherty et al. |
| 5,198,460 A | 3/1993 | Pandey et al. |
| 5,438,071 A | 8/1995 | Clauss et al. |
| 6,443,976 B1 | 9/2002 | Flower et al. |
| 6,693,093 B2 | 2/2004 | Chowdhary et al. |
| 6,924,359 B1 * | 8/2005 | Garen ............... C07K 16/18 435/328 |
| 2004/0110929 A1* | 6/2004 | Bjorn ............... C12N 9/6437 530/384 |
| 2005/0214298 A1 | 9/2005 | Garen et al. |
| 2006/0024730 A1 | 2/2006 | Bjorn et al. |
| 2008/0206227 A1 | 8/2008 | Garen et al. |
| 2013/0216513 A1 | 8/2013 | Salas et al. |

FOREIGN PATENT DOCUMENTS

| | | | |
|---|---|---|---|
| JP | 2003-504315 A | 2/2003 | |
| JP | 2007-500744 A | 1/2007 | |
| JP | 2013-534427 A | 9/2013 | |
| WO | 0102439 A1 | 1/2001 | |
| WO | 2004/101740 A1 | 11/2004 | |
| WO | 2004101739 A2 | 11/2004 | |
| WO | WO-2006020979 A2 * | 2/2006 | ............ A61K 38/41 |
| WO | 2012/006633 A1 | 1/2012 | |
| WO | 2012006633 A1 | 1/2012 | |
| WO | WO-2012006633 A1 * | 1/2012 | ............ A61K 38/36 |
| WO | 2015/021711 A1 | 2/2015 | |
| WO | 2017/021528 A1 | 2/2017 | |
| WO | 2017/181145 A1 | 10/2017 | |

OTHER PUBLICATIONS

Vidarsson et al., Front Immunol. Oct. 20, 2014;5:520. doi: 10.3389/fimmu.2014.00520. eCollection 2014. PMID: 25368619.*
Persson, E., FEBS Lett. Aug. 18, 1997;413(2):359-63. doi: 10.1016/s0014-5793(97)00941-1. PMID: 9280313.*
Abdulkadir, S.A., et al., Tissue factor expression and angiogenesis in human prostate carcinoma. Hum Pathol, 2000. 31(4): p. 443-7.
Adorno-Cruz, V., et al., Cancer stem cells: targeting the roots of cancer, seeds of metastasis, and sources of therapy resistance. Cancer Res, 2015. 75(6): p. 924-9.
Afuwape AO, Kiriakidis S and Paleolog EM. The role of the angiogenic molecule VEGF in the pathogenesis of rheumatoid arthritis. Histology and histopathology. 2002; 17(3):961-972.
Akashi, T., et al., Tissue factor expression and prognosis in patients with metastatic prostate cancer. Urology, 2003. 62(6): p. 1078-82.

(Continued)

*Primary Examiner* — Michael Szperka
(74) *Attorney, Agent, or Firm* — Meunier Carlin & Curfman LLC

(57) ABSTRACT

Disclosed are methods and compositions related to immunoconjugates. Particularly disclosed are immunoconjugates that comprise the Fc portion of IgG3 as well as Factor VII light chain or Factor VII. Also disclosed is an immunoconjugate protein, wherein said immunoconjugate protein comprises a hybrid Fc region of an IgG1 and an IgG3 immunoglobulin conjugated to Factor VII. These immunoconjugates can target Tissue Factor (TF) expressing cells.

11 Claims, 14 Drawing Sheets

Specification includes a Sequence Listing.

(56) References Cited

OTHER PUBLICATIONS

Altomare, D.F., et al., Tissue factor and vascular endothelial growth factor expression in colorectal cancer: relation with cancer recurrence. Colorectal Dis, 2007. 9(2): p. 133-8.
Andoh, K., et al., Tissue factor activity in leukemia cells. Special reference to disseminated intravascular coagulation. Cancer, 1987. 59(4): p. 748-54.
Badolato, Raffaele, and Joost J. Oppenheim. "Role of cytokines, acute-phase proteins, and chemokinesin the progression of rheumatoid arthritis." Seminars in arthritis and rheumatism. vol. 26. No. 2. WB Saunders, 1996. pp. 526-538.
Bauer, K.A., et al., Tissue factor gene expression in acute myeloblastic leukemia. Thromb Res, 1989. 56(3): p. 425-30.
Benaroch, P., et al., HIV-1 assembly in macrophages. Retrovirology, 2010. 7:29.
Bledsoe, J.G. and S.M. Slack, Tissue factor expression by rat osteosarcoma cells adherent to tissue culture polystyrene and selected orthopedic biomaterials. J Biomater Sci Polym Ed, 1998. 9(12): p. 1305-12.
Bora PS, Hu Z, Tezel TH, Sohn JH, Kang SG, Cruz JM, Bora NS, Garen A and Kaplan HJ. Immunotherapy for choroidal neovascularization in a laser-induced mouse model simulating exudative (wet) macular degeneration. Proceedings of the National Academy of Sciences of the United States of America. 2003; 100(5):2679-2684.
Breij, E.C., et al., An antibody-drug conjugate that targets tissue factor exhibits potent therapeutic activity against a broad range of solid tumors. Cancer Res, 2014. 74(4): p. 1214-26.
Brenchley, J.M., et al., Microbial translocation is a cause of systemic immune activation in chronic HIV infection. Nat Med, 2006. 12(12): p. 1365-71.
Busso, N., et al., Role of the tissue factor pathway in synovial inflammation. Arthritis Rheum, 2003. 48(3): p. 651-9.
Callander, N.S., N. Varki, and L.V. Rao, Immunohistochemical identification of tissue factor in solid tumors. Cancer, 1992. 70(5): p. 1194-201.
Camera, M., et al., The Role of Tissue Factor in Atherothrombosis and Coronary Artery Disease: Insights into Platelet Tissue Factor. Semin Thromb Hemost, 2015. 41(7): p. 737-46.
Camerer, E., A.B. Kolsto, and H. Prydz, Cell biology of tissue factor, the principal initiator of blood coagulation. Thromb Res, 1996. 81(1): p. 1-41.
Chen, L., et al., Tissue factor expression in rheumatoid synovium: a potential role in pannus invasion of rheumatoid arthritis. Acta Histochem, 2013, 692-697.
Cheng J, Xu J, Duanmu J, Zhou H, Booth CJ and Hu Z. Effective treatment of human lung cancer by targeting tissue factor with a factor VII-targeted photodynamic therapy. Current cancer drug targets. 2011; 11(9):1069-1081.
Christmas, N.J. A Phase 2 Study (EMERGE) Evaluating Repeated Intravitreal Administration of ICON-1 in Patients with Choroidal Neovascularization (CNV) Secondary to Age-related Macular Degeneration (AMD). Investig. Ophthalmol. Vis. Sci. 2016, 57, 4434.
Chudasama, A. Maruani, S. Caddick, Recent advances in the construction of antibody-drug conjugates. Nat Chem 8, 114-119 (2016).
Cocco, E., et al., hI-con1, a factor VII-IgGFc chimeric protein targeting tissue factor for immunotherapy of uterine serous papillary carcinoma. Br J Cancer, 2010. 103(6): p. 812-9.
Colville-Nash, P.R. and D.L. Scott, Angiogenesis and rheumatoid arthritis: pathogenic and therapeutic implications. Ann Rheum Dis, 1992. 51(7): p. 919-25.
Contrino J, Hair G, Kreutzer DL and Rickles FR. In situ detection of tissue factor in vascular endothelial cells: correlation with the malignant phenotype of human breast disease. Nature medicine. 1996; 2(2):209-215.
Contrino, J., et al., In situ characterization of antigenic and functional tissue factor expression in human tumors utilizing monoclonal antibodies and recombinant factor VIIa as probes. Am J Pathol, 1994. 145(6): p. 1315-22.

De Goeij, B.E., et al., High turnover of tissue factor enables efficient intracellular delivery of antibody-drug conjugates. Mol Cancer Ther, 2015. 14(5): p. 1130-40.
Deane et al., The number of elevated cytokines and chemokines in preclinical seropositive rheumatoid arthritis predicts time to diagnosis in an agedependent manner. Arthritis Rheum 62, 3161-3172 (2010).
Dorner, T. and G.R. Burmester, The role of B cells in rheumatoid arthritis: mechanisms and therapeutic targets. Curr Opin Rheumatol, 2003. 15(3): p. 246-52.
Dorner, T. and P.E. Lipsky, B-cell targeting: a novel approach to immune intervention today and tomorrow. Expert Opin Biol Ther, 2007. 7(9): p. 1287-99.
Dorner, T., et al., Current status on B-cell depletion therapy in autoimmune diseases other than rheumatoid arthritis. Autoimmun Rev, 2009. 9(2): p. 82-9.
Dorner, T., N. Kinnman, and P.P. Tak, Targeting B cells in immune-mediated inflammatory disease: a comprehensive review of mechanisms of action and identification of biomarkers. Pharmacol Ther, 2010. 125(3): p. 464-75.
Duanmu J, Cheng J, Xu J, Booth CJ and Hu Z. Effective treatment of chemoresistant breast cancer in vitro and in vivo by a factor VII-targeted photodynamic therapy. British journal of cancer. 2011; 104(9):1401-1409.
Ferrandina, G., et al., Targeting CD133 antigen in cancer. Expert Opin Ther Targets, 2009. 13(7): p. 823-37.
Ferrara N. VEGF and the quest for tumour angiogenesis factors. Nature reviews Cancer. 2002; 2(10):795-803.
Folkman J. Tumor angiogenesis and tissue factor. Nature medicine. 1996; 2(2):167-168.
Folkman, J., Angiogenesis in cancer, vascular, rheumatoid and other disease. Nat Med, 1995. 1(1): p. 27-31.
Folkman, J., Tumor angiogenesis: therapeutic implications. N Engl J Med, 1971. 285(21): p. 1182-6.
Freeburn, J.C., W.S. Gilmore, and J.J. Strain, The effect of cytokines on tissue factor expression in HL-60 and U937 cell lines. Biochem Soc Trans, 1995. 23(2): p. 286S.
Friedl, J., et al., Induction of permeability across endothelial cell monolayers by tumor necrosis factor (TNF) occurs via a tissue factor-dependent mechanism: relationship between the procoagulant and permeability effects of TNF. Blood, 2002. 100(4): p. 1334-9.
Fujimoto J, Sakaguchi H, Hirose R, Wen H and Tamaya T. Angiogenesis in endometriosis and angiogenic factors. Gynecologic and obstetric investigation. 1999; 48 Suppl 1:14-20.
Funderburg, N.T., et al., Increased tissue factor expression on circulating monocytes in chronic HIV infection: relationship to in vivo coagulation and immune activation. Blood, 2010. 115(2): p. 161-7.
Geisbert, T.W., et al., Mechanisms underlying coagulation abnormalities in ebola hemorrhagic fever: overexpression of tissue factor in primate monocytes/macrophages is a key event. J Infect Dis, 2003. 188(11): p. 1618-29.
Geisbert, T.W., et al., Treatment of Ebola virus infection with a recombinant inhibitor of factor VIIa/tissue factor: a study in rhesus monkeys. Lancet, 2003. 362(9400): p. 1953-8.
Grabowski, E.F., D.B. Zuckerman, and Y. Nemerson, The functional expression of tissue factor by fibroblasts and endothelial cells under flow conditions. Blood, 1993. 81(12): p. 3265-70. Abstract.
Grossniklaus, H.E., et al., Macrophage and retinal pigment epithelium expression of angiogenic cytokines in choroidal neovascularization. Mol Vis, 2002. 8: p. 119-26.
Guan, M., et al., Tissue factor expression and angiogenesis in human glioma. Clin Biochem, 2002. 35(4): p. 321-5.
Hair et al., Tissue factor expression in human leukemic cells. Leuk Res 20, 1-11 (1996).
Hamada, K., et al., Expression of tissue factor correlates with grade of malignancy in human glioma. Cancer, 1996. 77(9): p. 1877-83.
Hanahan, D. and R.A. Weinberg, Hallmarks of cancer: the next generation. Cell, 2011. 144(5): p. 646-74.
Hanahan, D. and R.A. Weinberg, The hallmarks of cancer. Cell, 2000. 100(1): p. 57-70.

(56) References Cited

OTHER PUBLICATIONS

Herbert, J.M., et al., IL-4 inhibits LPS-, IL-1 beta- and TNF alpha-induced expression of tissue factor in endothelial cells and monocytes. FEBS Lett, 1992. 310(1): p. 31-3.
Herbert, J.M., et al., Malformin-A1 inhibits the binding of interleukin-1 beta (IL1 beta) and suppresses the expression of tissue factor in human endothelial cells and monocytes. Biochem Pharmacol, 1994. 48(6): p. 1211-7.
Hu et al. Therapeutic antibody-like immunoconjugates against tissue factor with the potential to treat angiogenesis-dependent as well as macrophage-associated human diseases. Antibodies. 2018, 7(1), 8; doi:10.3390/antib7010008.
Hu et al., Targeting tissue factor as a novel therapeutic oncotarget for eradication of cancer stem cells isolated from tumor cell lines, tumor xenografts and patients of breast, lung and ovarian cancer. Oncotarget 8, 1481-1494 (2017).
Hu Z and Garen A. Intratumoral injection of adenoviral vectors encoding tumor-targeted immunoconjugates for cancer immunotherapy. Proceedings of the National Academy of Sciences of the United States of America. 2000; 97(16):9221-9225.
Hu Z and Garen A. Targeting tissue factor on tumor vascular endothelial cells and tumor cells for immunotherapy in mouse models of prostatic cancer. Proceedings of the National Academy of Sciences of the United States of America. 2001; 98(21):12180-12185.
Hu Z and Li J. Natural killer cells are crucial for the efficacy of Icon (factor VII/human IgG1 Fc) immunotherapy in human tongue cancer. BMC immunology. 2010; 11:49.
Hu Z, Cheng J, Xu J, Ruf W and Lockwood CJ. Tissue factor is an angiogenic-specific receptor for factor VII-targeted immunotherapy and photodynamic therapy. Angiogenesis. (2017) 20:85-96.
Hu Z, Rao B, Chen S and Duanmu J. Selective and effective killing of angiogenic vascular endothelial cells and cancer cells by targeting tissue factor using a factor VII-targeted photodynamic therapy for breast cancer. Breast cancer research and treatment. 2011; 126(3):589-600.
Hu Z, Rao B, Chen S and Duanmu J. Targeting tissue factor on tumour cells and angiogenic vascular endothelial cells by factor VII-targeted verteporfin photodynamic therapy for breast cancer in vitro and in vivo in mice. BMC cancer. 2010; 10:235.
Hu Z, Sun Y and Garen A. Targeting tumor vasculature endothelial cells and tumor cells for immunotherapy of human melanoma in a mouse xenograft model. Proceedings of the National Academy of Sciences of the United States of America. 1999; 96(14):8161-8166.
Hu, Factor VII—Targeted Photodynamic Therapy for Breast Cancer and Its Therapeutic Potential for Other Solid Cancers and Leukemia. Breast Cancer—Current and Alternative Therapeutic Modalities, Esra Gunduz and Mehmet Gunduz (Ed.), ISBN: 978-953-307-776-5, InTech. E. Gunduz, Gunduz, M., Ed., Breast Cancer—Current and Alternative Therapeutic Modalities (InTech, 2011), pp. 175-196.
Hu, Z., et al., Assessing the carcinogenic potential of low-dose exposures to chemical mixtures in the environment: focus on the cancer hallmark of tumor angiogenesis. Carcinogenesis, 2015. 36 Suppl 1: p. S184-S202.
Juarez, M., A. Filer, and C.D. Buckley, Fibroblasts as therapeutic targets in rheumatoid arthritis and cancer. Swiss Med Wkly, 2012. 142: p. w13529.
Kageshita, T., et al., Tissue factor expression and serum level in patients with melanoma does not correlate with disease progression. Pigment Cell Res, 2001. 14(3): p. 195-200.
Kaido, T., et al., Tissue factor is a useful prognostic factor of recurrence in hepatocellular carcinoma in 5-year survivors. Hepatogastroenterology, 2005. 52(65): p. 1383-7.
Kakkar, A.K., et al., Tissue factor expression correlates with histological grade in human pancreatic cancer. Br J Surg, 1995. 82(8): p. 1101-4.
Kaushal, V., et al., Expression of tissue factor in prostate cancer correlates with malignant phenotype. Appl Immunohistochem Mol Morphol, 2008. 16(1): p. 1-6.

Khorana, A.A., et al., Tissue factor expression, angiogenesis, and thrombosis in pancreatic cancer. Clin Cancer Res, 2007. 13(10): p. 2870-5.
Kim, J. K. et al. Mapping the site on human IgG for binding of the MHC class I-related receptor, FcRn. European journal of immunology 29, 1999, 2819-2825.
Klagsbrun M, Sullivan R, Smith S, Rybka R and Shing YE. Purification of endothelial cell growth factors by heparin affinity chromatography. Methods in enzymology. 1987; 147:95-105.
Koch U, Krause M and Baumann M. Cancer stem cells at the crossroads of current cancer therapy failures—radiation oncology perspective. Seminars in cancer biology. 2010; 20(2):116-124.
Kokkonen et al., Up-regulation of cytokines and chemokines predates the onset of rheumatoid arthritis. Arthritis Rheum 62, 383-391 (2010).
Konigsberg WH and Nemerson Y. Molecular cloning of the cDNA for human tissue factor. Cell. 1988; 52(5):639-640.
Koomagi, R. and M. Volm, Tissue-factor expression in human non-small-cell lung carcinoma measured by immunohistochemistry: correlation between tissue factor and angiogenesis. Int J Cancer, 1998. 79(1): p. 19-22.
Krikun G, Hu Z, Osteen K, Bruner-Tran KL, Schatz F, Taylor HS, Toti P, Arcuri F, Konigsberg W, Garen A, Booth CJ and Lockwood CJ. The immunoconjugate "icon" targets aberrantly expressed endothelial tissue factor causing regression of endometriosis. The American journal of pathology. 2010; 176(2):1050-1056.
Krikun, G., Endometriosis, angiogenesis and tissue factor. Scientifica (Cairo), 2012. 2012: p. 306830.
Krikun, F. Schatz, H. Taylor, C. J. Lockwood, Endometriosis and tissue factor. Ann N Y Acad Sci 1127, 101-105 (2008).
Kubota, T., et al., Tissue factor released from leukemic cells. Thromb Haemost, 1991. 65(1): p. 59-63.
Lewis, J.C., et al., Tissue factor expression during coculture of endothelial cells and monocytes. Exp Mol Pathol, 1995. 62(3): p. 207-18.
Lockwood, C.J., et al., The role of tissue factor in regulating endometrial haemostasis: implications for progestin-only contraception. Hum Reprod, 2000. 15 Suppl 3: p. 144-51.
Lopez-Pedrera, C., et al., Tissue factor as an effector of angiogenesis and tumor progression in hematological malignancies. Leukemia, 2006. 20(8): p. 1331-40.
Luther, T., et al., Flow cytometric analysis of tissue factor (TF) expression on stimulated monocytes—comparison to procoagulant activity of mononuclear blood cells. Blut, 1990. 61(6): p. 375-8.
Mackman, et al., Tissue Factor and Atherothrombosis, J of Athrosclerosis and Thrombosis 22:6, 543.
Marrelli, A., et al., Angiogenesis in rheumatoid arthritis: A disease specific process or a common response to chronic inflammation? Autoimmun Rev, 2011.
Maruotti, N., et al., Angiogenesis in rheumatoid arthritis. Histol Histopathol, 2006. 21(5): p. 557-66.
Mayr, M., et al., Proteomics, metabolomics, and immunomics on microparticles derived from human atherosclerotic plaques. Circ Cardiovasc Genet, 2009. 2(4): p. 379-88.
Mechiche, H. and P. Nguyen, IL-4 modulates tissue factor expression by human B lymphocytes in response to phorbol myristate acetate. Thromb Haemost, 2007. 97(1): p. 158-9.
Mechiche, H., P. Cornillet-Lefebvre, and P. Nguyen, A subpopulation of human B lymphocytes can express a functional Tissue Factor in response to phorbol myristate acetate. Thromb Haemost, 2005. 94(1): p. 146-54.
Meerarani, P., et al., Atherothrombosis: role of tissue factor; link between diabetes, obesity and inflammation. Indian J Exp Biol, 2007. 45(1): p. 103-10.
Moncharmont C, Levy A, Gilormini M, Bertrand G, Chargari C, Alphonse G, Ardail D, Rodriguez-Lafrasse C and Magne N. Targeting a cornerstone of radiation resistance: cancer stem cell. Cancer letters. 2012; 322(2):139-147.
Morrissey JH, Fakhrai H and Edgington TS. Molecular cloning of the cDNA for tissue factor, the cellular receptor for the initiation of the coagulation protease cascade. Cell. 1987; 50(1):129-135.

(56) References Cited

OTHER PUBLICATIONS

Mousa, S.A., Role of current and emerging antithrombotics in thrombosis and cancer. Timely Top Med Cardiovasc Dis, 2006. 10: p. E19. Abstract.
Nakasaki, T., et al., 5 Decreased tissue factor and tissue-plasminogen activator antigen in relapsed acute promyelocytic leukemia. Am J Hematol, 2000. 64(3): p. 145-50.
Nakasaki, T., et al., Elevated tissue factor levels in leukemic cell homogenate. Clin Appl Thromb Hemost, 2000. 6(1): p. 14-7.
Nakasaki, T., et al., Expression of tissue factor and vascular endothelial growth factor is associated with angiogenesis in colorectal cancer. Am J Hematol, 2002. 69(4): p. 247-54.
Natsume et al., Engineered antibodies of IgG1/IgG3 mixed isotype with enhanced cytotoxic activities. Cancer research 68, 3863-3872 (2008).
Nemerson Y. Tissue factor and hemostasis. Blood. 1988; 71(1):1-8.
Nemerson Y. Tissue factor and the initiation of blood coagulation. Advances in experimental medicine and biology. 1987; 214:83-94.
Nitori, N., et al., Prognostic significance of tissue factor in pancreatic ductal adenocarcinoma. Clin Cancer Res, 2005. 11(7): p. 2531-9.
Osterud, B. and E. Bjorklid, The production and availability of tissue thromboplastin in cellular populations of whole blood exposed to various concentrations of endotoxin. An assay for detection of endotoxin. Scand J Haematol, 1982. 29(2): p. 175-84.
Owens, A.P., 3rd and N. Mackman, Role of tissue factor in atherothrombosis. Curr Atheroscler Rep, 2012. 14(5): p. 394-401.
Paleolog, E.M. and R.A. Fava, Angiogenesis in rheumatoid arthritis: implications for future therapeutic strategies. Springer Semin Immunopathol, 1998. 20(1-2): p. 73-94.
Paleolog, E.M., Angiogenesis in rheumatoid arthritis. Arthritis Res, 2002. 4 Suppl 3: p. S81-90.
Pecen, P.E. and P.K. Kaiser, Current phase 1/2 research for neovascular age-related macular degeneration. Curr Opin Ophthalmol, 2015. 26(3): p. 188-93.
Pendurthi, U.R., D. Alok, and L.V. Rao, Binding of factor VIIa to tissue factor induces alterations in gene expression in human fibroblast cells: up-regulation of poly(A) polymerase. Proc Natl Acad Sci U S A, 1997. 94(23): p. 12598-603.
Phillips, T.M., W.H. McBride, and F. Pajonk, The response of CD24(-/low)/CD44+ breast cancer-initiating cells to radiation. J Natl Cancer Inst, 2006. 98(24): p. 1777-85.
Poon, R.T., et al., Tissue factor expression correlates with tumor angiogenesis and invasiveness in human hepatocellular carcinoma. Clin Cancer Res, 2003. 9(14): p. 5339-45.
Presta, L., et al., Generation of a humanized, high affinity anti-tissue factor antibody for use as a novel antithrombotic therapeutic. Thromb Haemost, 2001. 85(3): p. 379-89.
Rak, J., et al., Tissue factor in cancer and angiogenesis: the molecular link between genetic tumor progression, tumor neovascularization, and cancer coagulopathy. Semin Thromb Hemost, 2006.32(1): p. 54-70.
Rickles, F.R., et al., Tissue factor expression in human leukocytes and tumor cells. Thromb Haemost, 1995. 74(1): p. 391-5.
Rosenberg, Z.F. and A.S. Fauci, Immunopathogenesis of HIV infection. FASEB J, 1991. 5(10): p. 2382-90.
Saha, D., et al., Tissue factor and atherothrombosis. Curr Pharm Des, 2015. 21(9): p. 1152-7.
Sawada, M., et al., Expression of tissue factor in non-small-cell lung cancers and its relationship to metastasis. Br J Cancer, 1999. 79(3-4): p. 472-7.
Schatz, F., et al., Progestin-regulated expression of tissue factor in decidual cells: implications in endometrial hemostasis, menstruation and angiogenesis. Steroids, 2003. 68(10-13): p. 849-60.
Schecter, A.D., et al., Tissue factor expression in human arterial smooth muscle cells. TF is present in three cellular pools after growth factor stimulation. J Clin Invest, 1997. 100(9): p. 2276-85.
Sheridan, C., et al., CD44+/CD24- breast cancer cells exhibit enhanced invasive properties: an 20 early step necessary for metastasis. Breast Cancer Res, 2006. 8(5): p. R59.
Shigemori, C., et al., Tissue factor expression and metastatic potential of colorectal cancer. Thromb Haemost, 1998. 80(6): p. 894-8.
Shoji, M., et al., Activation of coagulation and angiogenesis in cancer: immunohistochemical localization in situ of clotting proteins and vascular endothelial growth factor in human cancer. Am J Pathol, 1998. 152(2): p. 399-411.
Spicer EK, Horton R, Bloem L, Bach R, Williams KR, Guha A, Kraus J, Lin TC, Nemerson Y and Konigsberg WH. Isolation of cDNA clones coding for human tissue factor: primary structure of the protein and cDNA. Proceedings of the National Academy of Sciences of the United States of America. 1987; 84(15):5148-5152.
Stapleton, N. M. et al. Competition for FcRn-mediated transport gives rise to short half-life of human IgG3 and offers therapeutic potential. Nature communications 2, 599, doi: 10.1038/ncomms1608 (2011).
Stupack, D.G., C.M. Storgard, and D.A. Cheresh, A role for angiogenesis in rheumatoid arthritis. Braz J Med Biol Res, 1999. 32(5): p. 573-81.
Sturm, U., et al., Immunohistological detection of tissue factor in normal and abnormal human mammary glands using monoclonal antibodies. Virchows Arch A Pathol Anat Histopathol, 1992. 421(2): p. 79-86.
Syed, The breast cancer market. Nature reviews. Drug discovery 14, 233-234 (2015).
Szekanecz, A. Pakozdi, A. Szentpetery, T. Besenyei, A. E. Koch, Chemokines and angiogenesis in rheumatoid arthritis. Front Biosci (Elite Ed) 1, 44-51 (2009).
Szekanecz, Z. and A.E. Koch, Angiogenesis and its targeting in rheumatoid arthritis. Vascul Pharmacol, 2009. 51(1): p. 1-7.
Szekanecz, Z. and A.E. Koch, Endothelial cells in inflammation and angiogenesis. Curr Drug Targets Inflamm Allergy, 2005. 4(3): p. 319-23.
Szekanecz, Z., et al., Angiogenesis in rheumatoid arthritis. Autoimmunity, 2009. 42(7): p. 563-73.
Szekanecz, Z., G. Szegedi, and A.E. Koch, Angiogenesis in rheumatoid arthritis: pathogenic and clinical significance. J Investig Med, 1998. 46(2): p. 27-41.
Szekanecz, Z., L. Gaspar, and A.E. Koch, Angiogenesis in rheumatoid arthritis. Front Biosci, 2005. 10: p. 1739-53.
Takano, S., et al., Tissue factor, osteopontin, alphavbeta3 integrin expression in microvasculature of gliomas associated with vascular endothelial growth factor expression. Br J Cancer, 2000. 82(12): p. 1967-73.
Tanaka, H., et al., Studies on leukemic cell tissue factor. Thromb Res, 1989. 53(6): p. 535-49.
Tanaka, M. and H. Yamanishi, The expression of tissue factor antigen and activity on the surface of leukemic cells. Leuk Res, 1993. 17(2): p. 103-11.
Tanaka, M. and T. Kishi, Induction of tissue factor by interleukin-2 in acute myelogenous leukemia (AML) cells. Growth Factors, 1990. 4(1): p. 1-8.
Tanaka, M., Induction of tissue factor-like activity of human monoblastic leukemia cell line by tumor necrosis factor-alpha. Thromb Res, 1989. 56(2): p. 201-11.
Tang, Y., et al., Mapping of angiogenic markers for targeting of vectors to tumor vascular endothelial cells. Cancer Gene Ther, 2007. 14(4): p. 346-53.
Tatsumi, K. and N. Mackman, Tissue Factor and Atherothrombosis. J Atheroscler Thromb, 2015. 22(6): p. 543-9.
Tezel TH, Bodek E, Sonmez K, Kaliappan S, Kaplan HJ, Hu Z and Garen A. Targeting tissue factor for immunotherapy of choroidal neovascularization by intravitreal delivery of factor VII-Fc chimeric antibody. Ocul Immunol Inflamm. 2007; 15(1):3-10.
Ueno, T., et al., Tissue factor expression in breast cancer tissues: its correlation with prognosis and plasma concentration. Br J Cancer, 2000. 83(2): p. 164-70.
Uno, K., et al., Tissue factor expression as a possible determinant of thromboembolism in ovarian cancer. Br J Cancer, 2007. 96(2): p. 290-5.
Vidal SJ, Rodriguez-Bravo V, Galsky M, Cordon-Cardo C and Domingo-Domenech J. Targeting cancer stem cells to suppress acquired chemotherapy resistance. Oncogene. 2014; 33(36):4451-4463.

(56) References Cited

OTHER PUBLICATIONS

Viles-Gonzalez, J.F. and J.J. Badimon, Atherothrombosis: the role of tissue factor. Int J Biochem Cell Biol, 2004. 36(1): p. 25-30.
Wada, H., Y. Wakita, and H. Shiku, Tissue factor expression in endothelial cells in health and disease. Blood Coagul Fibrinolysis, 1995. 6 Suppl 1: p. S26-31.
Wang, B., et al., Radiotherapy of human xenograft NSCLC tumors in nude mice with a 90Y-labeled anti-tissue factor antibody. Cancer Biother Radiopharm, 2005. 20(3): p. 300-9.
Waxman, E., et al., Tissue factor and its extracellular soluble domain: the relationship between intermolecular association with factor VIIa and enzymatic activity of the complex. Biochemistry, 1992. 31(16): p. 3998-4003.
Williams, R.O., M. Feldmann, and R.N. Maini, Anti-tumor necrosis factor ameliorates joint disease in murine collagen-induced arthritis. Proc Natl Acad Sci U S A, 1992. 89(20): p. 9784-8.
Zhang et al., Pathological expression of tissue factor confers promising antitumor response to a novel therapeutic antibody SC1 in triple negative breast cancer and pancreatic adenocarcinoma. Oncotarget 8, 59086-59102 (2017).
Zhang, Y., et al., Intravenous somatic gene transfer with antisense tissue factor restores blood flow by reducing tumor necrosis factor-induced tissue factor expression and fibrin deposition in mouse meth-A sarcoma. J Clin Invest, 1996. 97(10): p. 2213-24.
Zhang, Y.M., et al., Vascular origin of Kaposi's sarcoma. Expression of leukocyte adhesion molecule-1, thrombomodulin, and tissue factor. Am J Pathol, 1994. 144(1): p. 51-9.
Zhiwei Hu, Rulong Shen, Amanda Campbell, Elizabeth McMichael, Lianbo Yu, Bhuvaneswari Ramaswamy, Cheryl A. London, Tian Xu and William E. Carson III. Targeting Tissue Factor for Immunotherapy of Triple-Negative Breast Cancer using a Second-Generation ICON. Cancer Immunology Research, 2018, 671-684.
International Preliminary Report on Patentability issued for Application No. PCT/US2018/022443, dated Sep. 26, 2019.
Office Action issued for Japanese Application No. 2019-550815, dated Jan. 11, 2022.
Park, Hye In, Hyun Woung Yoon, and Sang Taek Jung. "The highly evolvable antibody Fc domain." Trends in biotechnology 34.11 (2016): 895-908.
Hu, Zhiwei, et al. "Targeting tissue factor as a novel therapeutic oncotarget for eradication of cancer stem cells isolated from tumor cell lines, tumor xenografts and patients of breast, lung and ovarian cancer." Oncotarget 8.1 (2017): 1481-1494.
Natsume, Akito, et al. "Engineered antibodies of IgG1/IgG3 mixed isotype with enhanced cytotoxic activities." Cancer Research 68.10 (2008): 3863-3872.
International Search Report and Written Opinion issued by the International Searching Authority (ISA/US) in PCT Application No. PCT/US2018/022443 dated Aug. 3, 2018. 14 pages.
Saxena, Abhishek, and Donghui Wu. "Advances in therapeutic Fc engineering-modulation of IgG-associated effector functions and serum half-life." Frontiers in immunology 7 (2016): 580.
Yasumoto, Atsushi, et al. "Overexpression of factor VII ameliorates bleeding diathesis of factor VIII-deficient mice with inhibitors." Thrombosis research 131.5 (2013): 444-449.
Extended Search Report issued in European patent application No. 18766917.1, dated Dec. 16, 2020.
Chinese National Intellectual Property Administration. Office Action issued in CN Application No. 201880018514.6 dated Feb. 28, 2023. 21 pages, including English translation.
Hu et al.; "Tissue factor-targeted immunotherapy of melanoma and triple negative breast cancer using a second generation ICON"; Journal of Immuno Therapy of Cancer 2015, 3(Suppl 2):P304; 2 pages; dated Nov. 8, 2015.
Communication pursuant to Article 94(3) issued in EP application No. 18766917.1-1112; dated Jun. 15, 2023; 5 pages.

\* cited by examiner b. SDS-PAGE
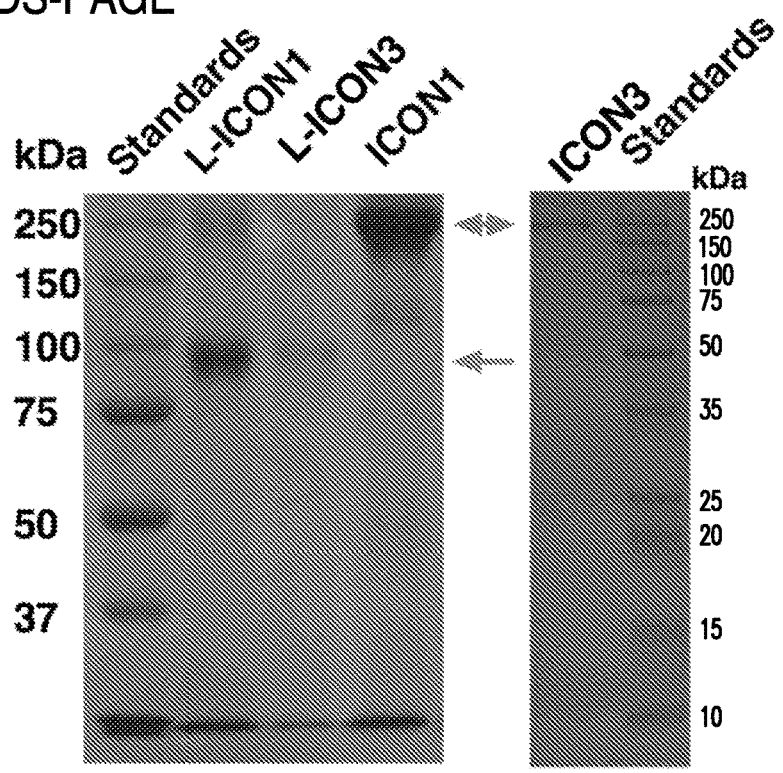
c. Fluorescent-WB
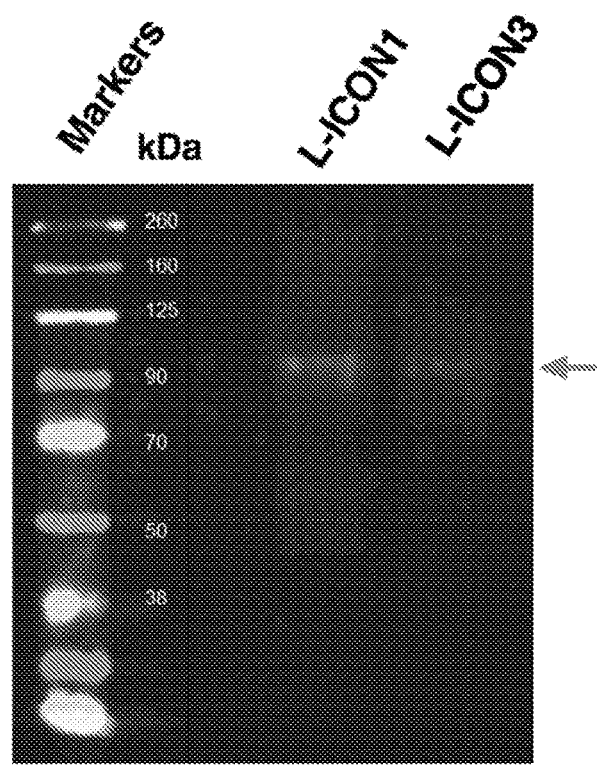
FIG. 1B-C

METHODS AND COMPOSITIONS RELATED TO A TISSUE FACTOR-TARGETING IGG3 IMMUNOCONJUGATES

CROSS-REFERENCE TO RELATED APPLICATIONS

This application is a national stage application filed under 35 U.S.C. § 371 of PCT/US2018/022443 filed Mar. 14, 2018, which claims benefit of U.S. Provisional Application No. 62/471,045, filed Mar. 14, 2017; U.S. Provisional Application No. 62/576,278, filed Oct. 24, 2017; and U.S. Provisional Application No. 62/623,269, filed Jan. 29, 2018, all three of which are hereby incorporated herein by reference in their entirety.

GOVERNMENT SUPPORT CLAUSE

This invention was made with government support under Grant No. UL1TR001070 awarded by National Center for Advancing Translational Sciences. The government has certain rights in the invention.

SEQUENCE LISTING

A Sequence Listing conforming to the rules of WIPO Standard ST.25 is hereby incorporated by reference. Said Sequence Listing has been filed as an electronic document via PatentCenter in ASCII formatted text. The electronic document, created on Aug. 2, 2023, is entitled "10336-305US1 ST25", and is 62,616 bytes in size.

BACKGROUND

Tissue factor ("TF") is a transmembrane glycoprotein that is the major initiator of the coagulation cascade. Under normal physiological conditions, active TF is not in contact with blood. During vascular injury, exposure to blood of sub-endothelial TF and collagen leads to activation of coagulation factors and platelets and subsequently to hemostatic plug formation. The inappropriate induction of TF expression in a variety of clinical settings can lead to life threatening thrombosis and/or contribute to pathological complications. TF exposure following plaque rupture is believed to be responsible for thrombotic occlusion leading to acute myocardial infarction and stroke. In these settings, proinflammatory signaling pathways activated by coagulation factors also contribute to edema formation and increased infarct size. Vascular injury associated with angioplasty leads to upregulation of TF on SMC's which is believed to induce cell signaling pathways associated with restenosis. TF overexpression in cancer and gram-negative sepsis leads to life threatening thrombosis and activation of inflammatory pathways.

TF is a modulator of pathological angiogenesis. In vivo studies revealed that TF is also a unique pathological angiogenic vascular endothelial cell (VEC)-surface receptor in vivo because of its selective expression on angiogenic VECs in vivo in tumor vasculature (Contrino et al. 1996; Folkman et al. 1996; Hu et al. 1999; Hu et al. 2001; Cheng et al. 2011; Duanmu et al. 2011), ocular (Bora et al. 2003) and endometriotic (Krikun et al. 2010) neovasculature from patients or animal models. Vascular endothelial growth factor (VEGF) plays a central role in angiogenesis-dependent cancer and non-malignant human diseases (Ferrara et al. 2002), such as macular degeneration (Klagsbrun et al. 1987), rheumatoid arthritis (Afuwape et al. 2002) and endometriosis (Fujimoto et al. 1999). Specifically, VEGF stimulates angiogenesis by binding to VEGR receptors on VECs in the pathological neovasculature (usually micro- or capillary vessels) in those angiogenesis-dependent diseases (Hu et al. Angiogenesis 2016). Using VEGF-induced in vitro angiogenic vascular endothelial models, it was shown that TF is an angiogenic-specific receptor and the target for Factor VII-targeted therapeutics, suggesting that TF-targeting agents can have therapeutic potential to treat cancer (solid cancer and leukemia), wet form of age-related macular degeneration (AMD), endometriosis and rheumatoid arthritis.

TF is a common yet specific biomarker and therapeutic target for cancer cells, cancer stem cells (CSC) (Hu et al. Oncotarget 2016) and tumor vascular endothelial cells in solid cancers. TF is highly expressed in these cancer cells, for example, 80%-100% in breast cancer, 50%-85% in triple negative breast cancer (Hu et al. Cancer Immunol Res 2018), 40%-80% in lung cancer and 84% in ovarian cancer. These three types of cancer are not only difficult to control, but also are major causes of mortality in the United States and worldwide and often develop CSC-based resistance to chemotherapy and radiation therapy (Vidal et al. 2014; Moncharmont et al. 2012; Koch et al. 2010). In addition to the cancer of breast, lung and ovary, TF is also expressed at high percentages in many other human solid cancers as well as in leukemias and sarcomas (Hu. Antibodies 2018), for instance, 95% in primary melanoma and 100% in metastatic melanoma, 53%-90% in pancreatic cancer, 57%-100% in colorectal cancer, 63%-100% in hepatocellular carcinoma, 60%-78% in primary and metastatic prostate cancer and 47%-75% in glioma. Very recently, it was shown that TF is expressed by cancer stem cells in breast, lung and ovarian cancer and TF-targeting agents can eradicate those TF-expressing cancer stem cells without drug resistance (Hu et al. Oncotarget 2016).

It has also been shown that TF is expressed by choroidal neovasculature (CNV), a model of AMD in experimental animals (Bora et al. 2003). It has also been shown that TF was expressed by angiogenic vascular endothelial cells in endometriotic lesions (Krikun et al. 2010).

What is needed are methods and compositions related to an immune-targeting agent that specifically targets TF-expressing angiogenic VEC and cancer cells, and shows stronger antibody-dependent cell-mediated cytotoxicity (ADCC) than other agents that target TF-expressing cells.

SUMMARY

Disclosed herein are compositions comprising an immunoconjugate protein, wherein said immunoconjugate protein comprises an Fc region of an IgG3 immunoglobulin conjugated to Factor VII. The Factor VII can be light chain or full length (with or without K341A). The composition can comprise Tissue Factor (TH). Factor VII light chain can comprise human and murine Factor VII. IgG3 can comprise a mutation at R45H. The immunoconjugate protein can comprise SEQ ID NO: 2, and can be encoded by SEQ ID NO: 1. The immunoconjugate protein can be encoded as a secreted molecule in an expression vector. The vector can be a replication-deficient adenoviral vector. The vector can be an adeno-associated expression vector. A photosynthesizer, such as a photodynamic dye, can be coupled to the immunoconjugate. The immunoconjugate protein can be encoded as a secreted molecule in an expression vector. These immunoconjugates are referred to herein as third-generation tissue factor-targeting ICONs, named L-ICON3 and ICON3, respectively. Also disclosed are methods and kits for using L-ICON3 and ICON3.

Further disclosed is a method for treating or preventing a disease in a subject in need thereof, the method comprising administering to the subject an effective amount of the composition disclosed herein. The disease can be associated with TF. The disease can comprise pathological neovasculature involving a vascularized tumor, thrombogenesis, rheumatoid arthritis, endometriosis, or macular degeneration. The disease can be associated with macrophages expressing TF. The disease can be a viral infection, such as Ebola or HIV. The disease can be atherosclerosis.

The compositions disclosed herein can be used to prevent or treat metastasis in cancer. Treatment can occur by the administration of the immunoconjugate proteins disclosed herein in a pharmaceutically acceptable carrier.

Also disclosed herein are compositions comprising an immunoconjugate protein, wherein said immunoconjugate protein comprises a hybrid Fc region of an IgG1 and an IgG3 immunoglobulin conjugated to Factor VII. The Factor VII can be light chain or full length (with or without K341A). The composition can comprise Tissue Factor (TH). Factor VII light chain can comprise human and murine Factor VII. IgG3 can comprise a mutation at R45H. The immunoconjugate protein can comprise SEQ ID NO: 2, and can be encoded by SEQ ID NO: 1. The immunoconjugate protein can be encoded as a secreted molecule in an expression vector. The vector can be a replication-deficient adenoviral vector. The vector can be an adeno-associated expression vector. A photosynthesizer, such as a photodynamic dye, can be coupled to the immunoconjugate. The immunoconjugate protein can be encoded as a secreted molecule in an expression vector. These immunoconjugates are referred to herein as fourth generation tissue factor-targeting ICONs, named L-ICON4 and ICON4, respectively.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

The accompanying figures, which are incorporated in and constitute a part of this specification, illustrate several aspects of the disclosure, and together with the description, serve to explain the principles of the disclosure.

FIG. 1A-C shows diagrams and characterization of third and fourth generations of tissue factor-targeting immunoconjugates (ICONs). 1A shows diagrams of first, second, third (L-ICON3 and ICON3) and fourth (L-ICON4 and ICON4) generations of TF-targeting immunoconjugates (ICONs). 1B shows molecular weights of ICON1, L-ICON1, L-ICON3 and ICON3. 1C shows fluorescent Western blotting of L-ICON1 and L-ICON3. Note: Loaded amount for L-ICON1 and ICON1 proteins was 3 µg/lane and the amount for L-ICON3 protein was about half of L-ICON1 and ICON1 (1.5 µg).

FIG. 4A shows L-ICON3 is more effective in mediating ADCC to kill human ovarian cancer cells than L-ICON1 in vitro. FIG. 4B shows CDC. Human IgG (hIgG) was used as isotype negative control.

FIG. 6A shows L-ICON3 protein can bind to murine triple-negative breast cancer (TNBC) 4T1 cells. FIG. 6B shows that L-ICON3 is more effective than L-ICON1 in vivo in an orthotopic mouse model of murine TNBC 4T1. FIG. 6C shows all mice survived after L-ICON1 and L-ICON3 treatment, whereas all control mice died on day 11 after initiation of intratumoral injection of adenoviral vectors. There were 5 mice in each group in FIG. 6B-6C.

FIG. 10A-10B shows L-ICON1 has no detectable pro-coagulation activity, whereas ICON has about 5-6% pro-coagulation activity of FVIIa (100%). FIG. 10 suggests that modification of ICON with non-coagulant light chain has completely depleted the pro-coagulation activity from L-ICON1 and L-ICON3.

DETAILED DESCRIPTION

Definitions

Figure 1A:
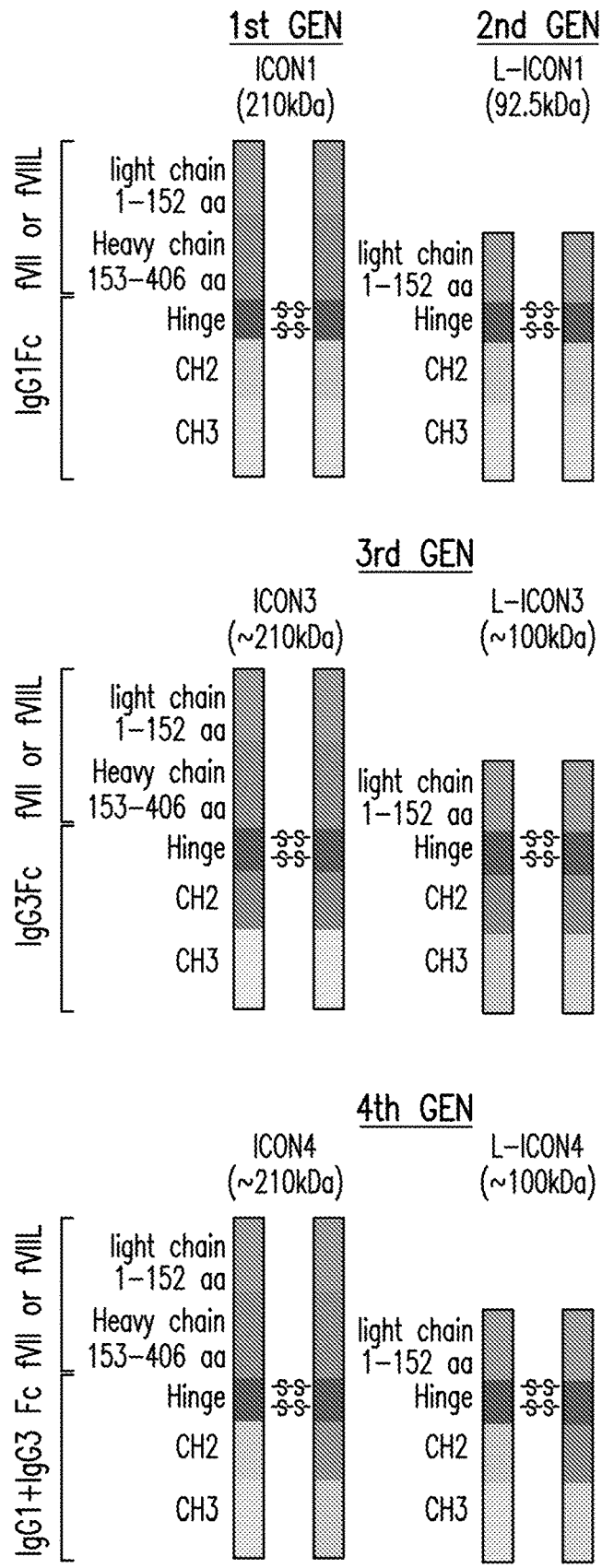

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of .+−0.20% or .+−0.10%, more preferably .+−0.5%, even more preferably .+−0.1%, and still more preferably .+−0.0.1% from the specified value, as such variations are appropriate to perform the disclosed methods.

A "prophylactic" treatment is a treatment administered to a subject who does not exhibit signs of a disease or exhibits only early signs for the purpose of decreasing the risk of developing pathology. The compounds of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective.

A "fragment" of a polypeptide refers to any portion of the polypeptide smaller than the full-length polypeptide or protein expression product. Fragments are, in one aspect, deletion analogs of the full-length polypeptide wherein one or more amino acid residues have been removed from the amino terminus and/or the carboxy terminus of the full-length polypeptide. Accordingly, "fragments" are a subset of deletion analogs described below.

An "analogue," "analog" or "derivative," which are used interchangeably, refers to a compound, e.g., a peptide or polypeptide, substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, to "alleviate" a disease means to reduce the frequency or severity of at least one sign or symptom of a disease or disorder.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, antisense RNA, small-hairpin RNA (shRNA), ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

As used herein, the term "diagnosis" refers to the determination of the presence of a disease or disorder. In some embodiments of the present invention, methods for making a diagnosis are provided which permit determination of the presence of a particular disease or disorder.

A "disease" is a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc. The therapies disclosed herein using the compositions disclosed herein can be used as stand-alone therapy or in combination with surgery, radiotherapy, chemotherapy, other forms of immunotherapy, including but not limited to immune checkpoint blockades, CAR-NK and -T cells, cytokines, natural killer cells, photodynamic therapy, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "cell" as used herein also refers to individual cells, cell lines, primary culture, or cultures derived from such cells unless specifically indicated. A "culture" refers to a composition comprising isolated cells of the same or a different type. A cell line is a culture of a particular type of cell that can be reproduced indefinitely, thus making the cell line "immortal." A cell culture can be a population of cells grown on a medium such as agar. A primary cell culture is a culture from a cell or taken directly from a living organism, which is not immortalized.

The term "biological sample" refers to a tissue (e.g., tissue biopsy), organ, cell (including a cell maintained in culture), cell lysate (or lysate fraction), biomolecule derived from a cell or cellular material (e.g. a polypeptide or nucleic acid), or body fluid from a subject. Non-limiting examples of body fluids include blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

General

A first generation agent that targets TF-expressing angiogenic vascular endothelial cells (VEC) and cancer cells has been previously reported. The first generation is referred to as an Immuno-Conjugate agent named ICON that consists of murine or human factor VII (1-406 aa, the natural ligand to tissue factor) with a mutation of K341A fused to the Fc region of IgG1 (FIG. 1A) (Hu et al. 1999, US Patent Application 2005/0214298, herein incorporated by reference in their entirety). The pro-coagulant effects of ICON-encoded zymogen factor VII have been significantly eliminated via targeted mutation of the lysine reside at position 341 (K341A) (Hu et al. 2001). ICON can be administered via intravenous injection of a recombinant protein or intra-lesional injection of an adenovirus vector. Intra-lesional ICON immunotherapy of experimental melanoma, prostate and head and neck tumors leads to marked tumor inhibition, and in some cases, complete eradication without affecting normal tissues (Hu et al. BMC Immunology 2010; Hu et al. PNAS 2000). Upon binding to TF-expressing cancer cells, ICON can mediate natural killer cell (NK) cell dependent antibody-dependent cell-mediated cytototoxicity (ADCC) and complement-dependent cytotoxicity (CDC) as its mechanism of action. For TF-targeted PDT, Hu et al. conjugated a monomeric fVII peptide with the photosensitizers (PS) verteporfin (VP) and Sn(IV) chlorin e6 (SnCe6) (referred to as fVII-VP and fVII-SnCe6, respectively) and showed that fVII-targeted PDT could selectively and effectively kill angiogenic vascular endothelial cells and cancer cells in vitro and in vivo in mouse models of human breast (Duanmu et al. 2011; Hu et al. BMC Cancer 2010; Hu et al. 2011) and lung cancer (Cheng et al. 2011).

Figure 7:
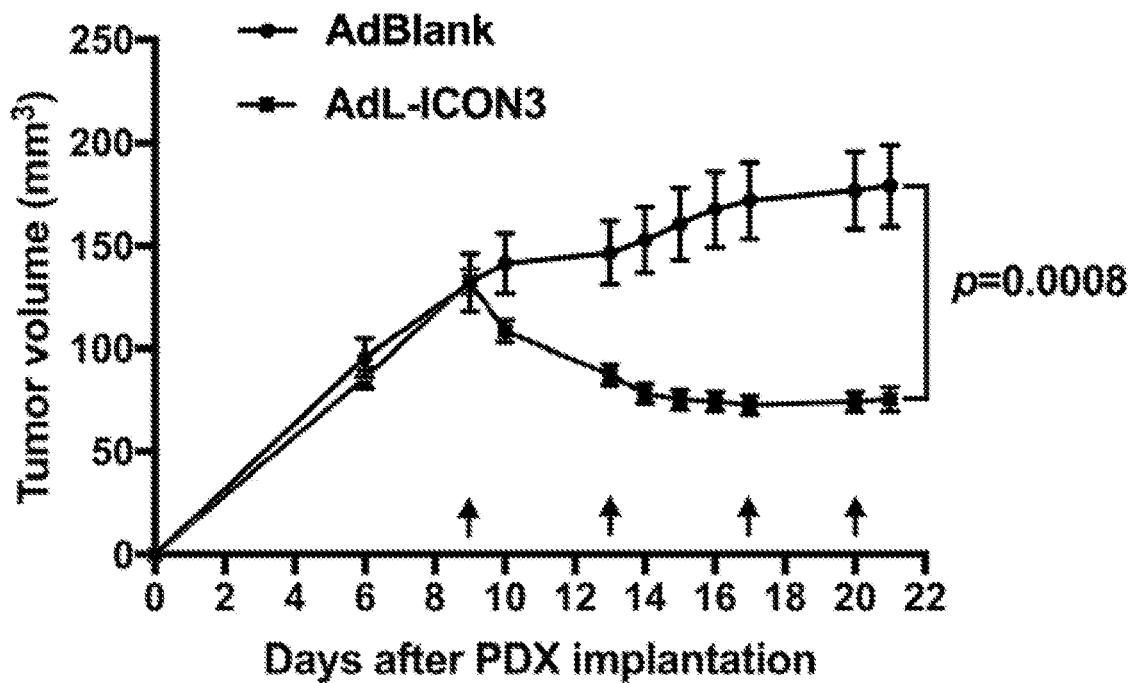
FIG. 7 shows L-ICON3 is effective for the treatment of patient's TNBC in an orthotopic patient-derived xenograft (PDX) mouse model in CB-17 SCID mice. The orthotopic TNBC PDX model was generated on day 0 by implanting TNBC PDX with BRCA-1 mutation from a donor NSG mouse (NOD SCID gamma) (Jackson Laboratory, JAX TM00089, breast tumor markers: TNBC ER−/PR−/HER2−, BRCA1 V757fs) into the fourth left mammary gland fat pad in 4 weeks-old, female CB-17 SCID (Taconic Farms). When tumor reaches a mean volume of 130 mm$^3$ (day 9), the mice were randomized into control and L-ICON3 groups (n=5 in each group) and were intratumorally (i.t.) injected with 1×10$^{10}$ Viral Particles (VP) of AdBlank (control vector) and AdL-ICON3 adenoviral vectors, respectively. Additional i.t. injections were done on days 13, 17 and 20. Therapeutic efficacy was determined by measuring tumor width (W) and length (L) with calipers in millimeters (mm) and calculating tumor volume (mm$^3$) using the formula $(W)^2 \times L/2$ (mm$^3$). Data are presented as Mean±SEM and analyzed by t-test for statistical significance using Prism software (GraphPad).
Figures 8A, 8B:
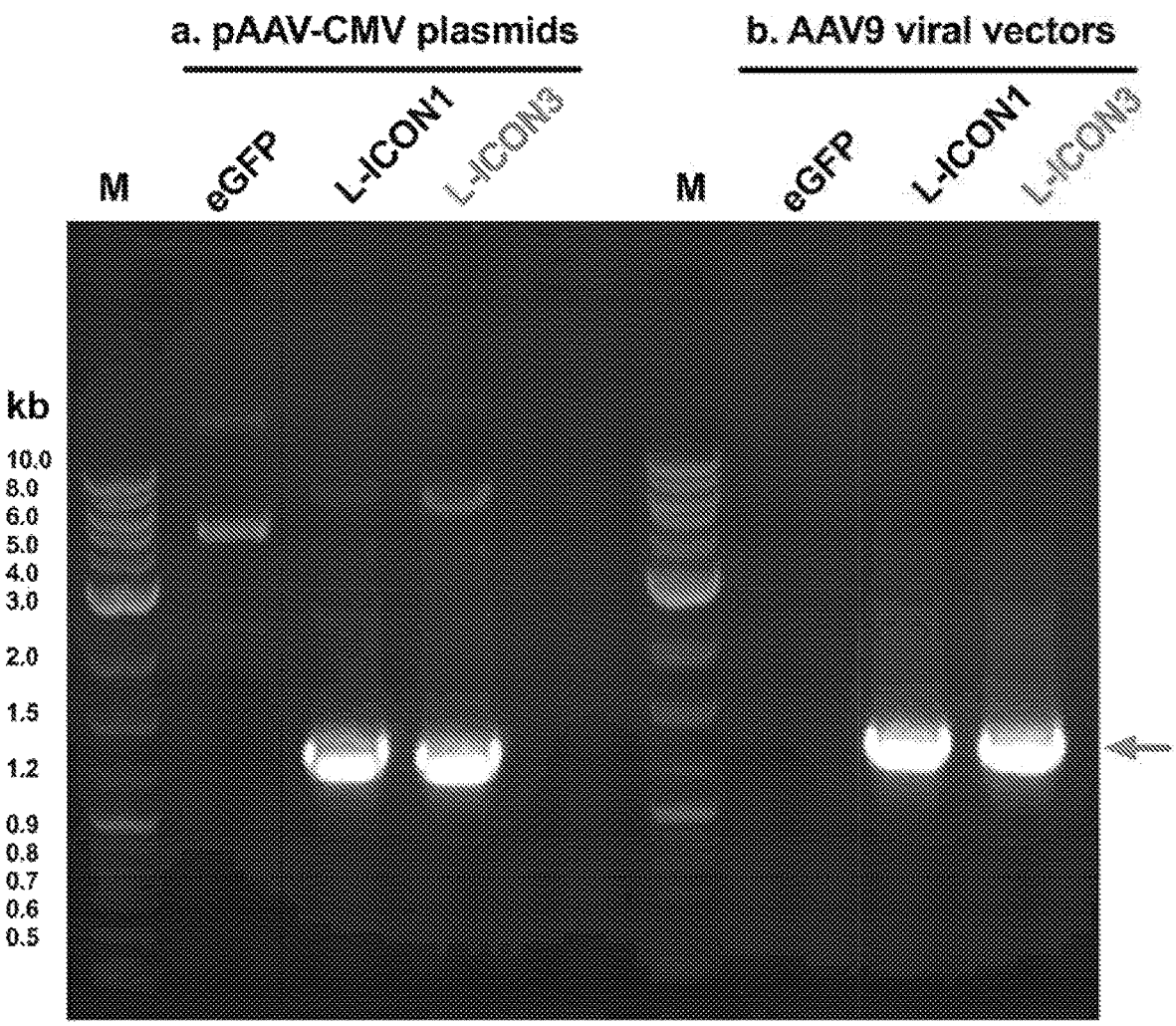
FIGS. 8A and B shows L-ICON3 insert cDNA is present with correct size in the plasmid DNA (pAAV-CMV) prior to making adeno-associated virus serotype 9 (AAV9) as well as in the intact AAV9 viral vectors (AAV9-L-ICON3) by PCR using primers specific for L-ICON1 and L-ICON3. M: DNA ladders in kilobases (Kb). eGFP: Enhanced green fluorescent protein as a negative control vector.
Figure 9:
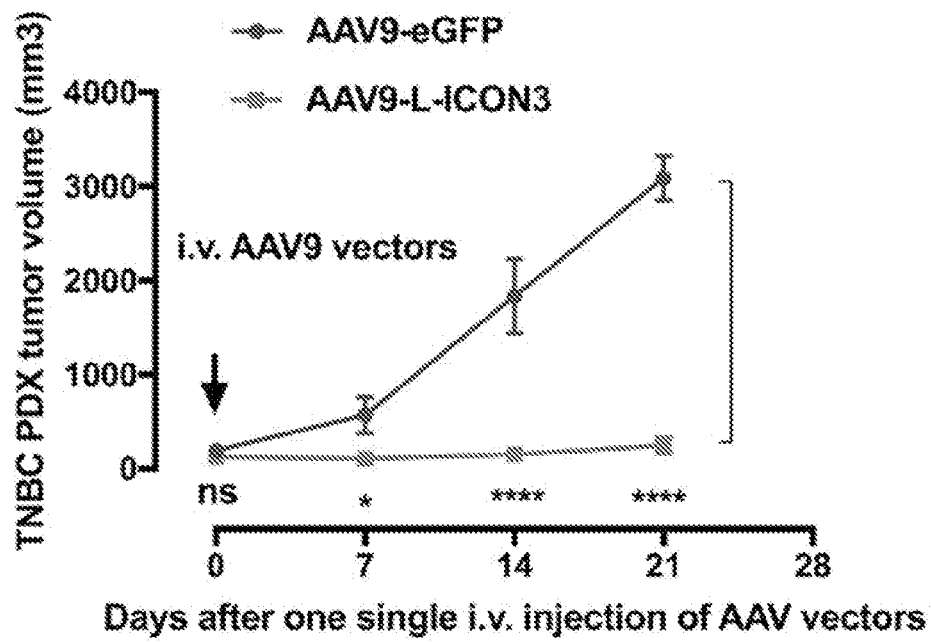
FIG. 9 shows L-ICON3 therapy via one single intravenous injection of AAV9-L-ICON3 (n=5) is effective for the treatment of patient's TNBC PDX in an orthotopic mouse model, as described in FIG. 7. AAV9-eGFP was a negative control vector (n=2).
Figure 10A:
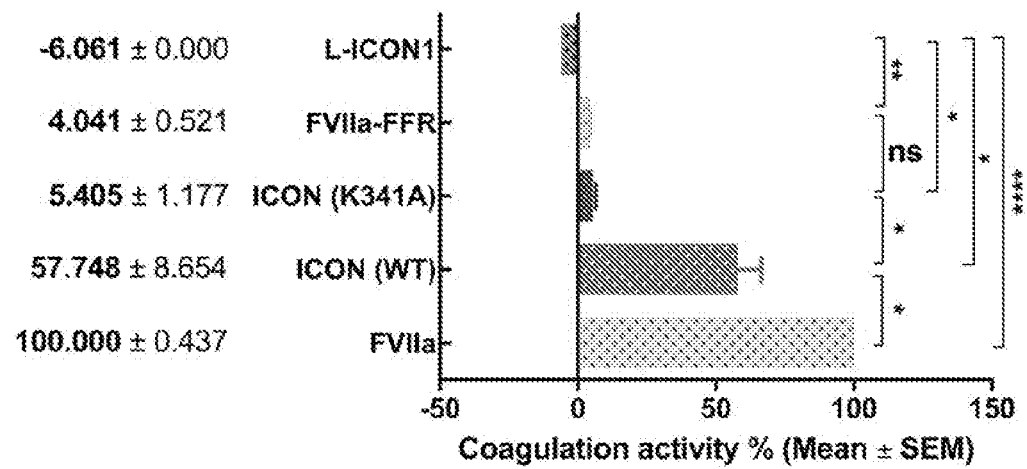
FIG. 10A-10B shows pro-coagulation activities of L-ICON1 and ICON determined by Factor VII Human Chromogenic Activity Assay. Active form of fVII (FVIIa) (American Diagnostica) as positive coagulation control; FVIIa-FFR: Active site inhibited FVIIa (American Diagnostica) as coagulation-inactive control. Their coagulation activities are also listed in Table 1. Representative data are presented as mean±SEM from two independent experiments.
Figure 10B:
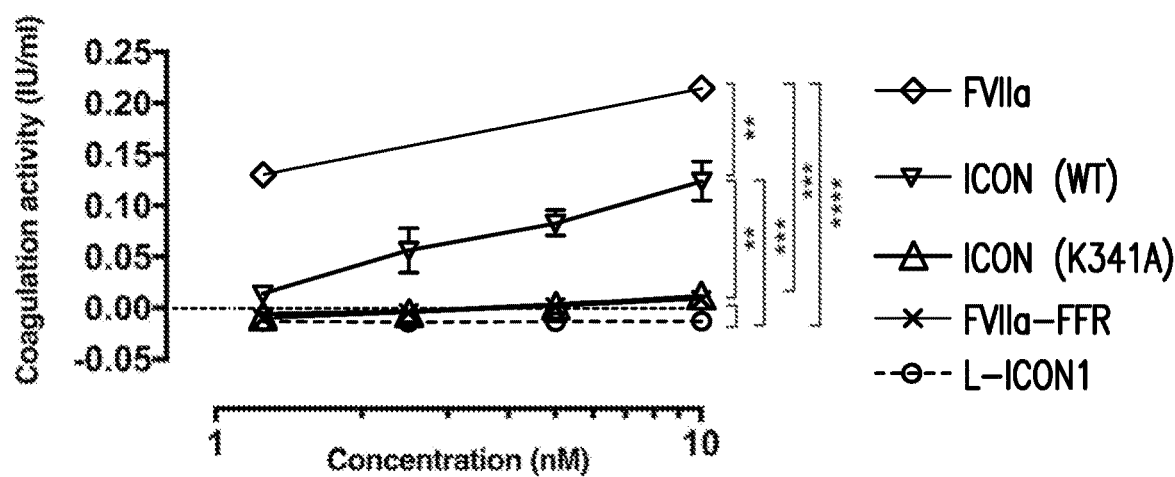
Figure 11:
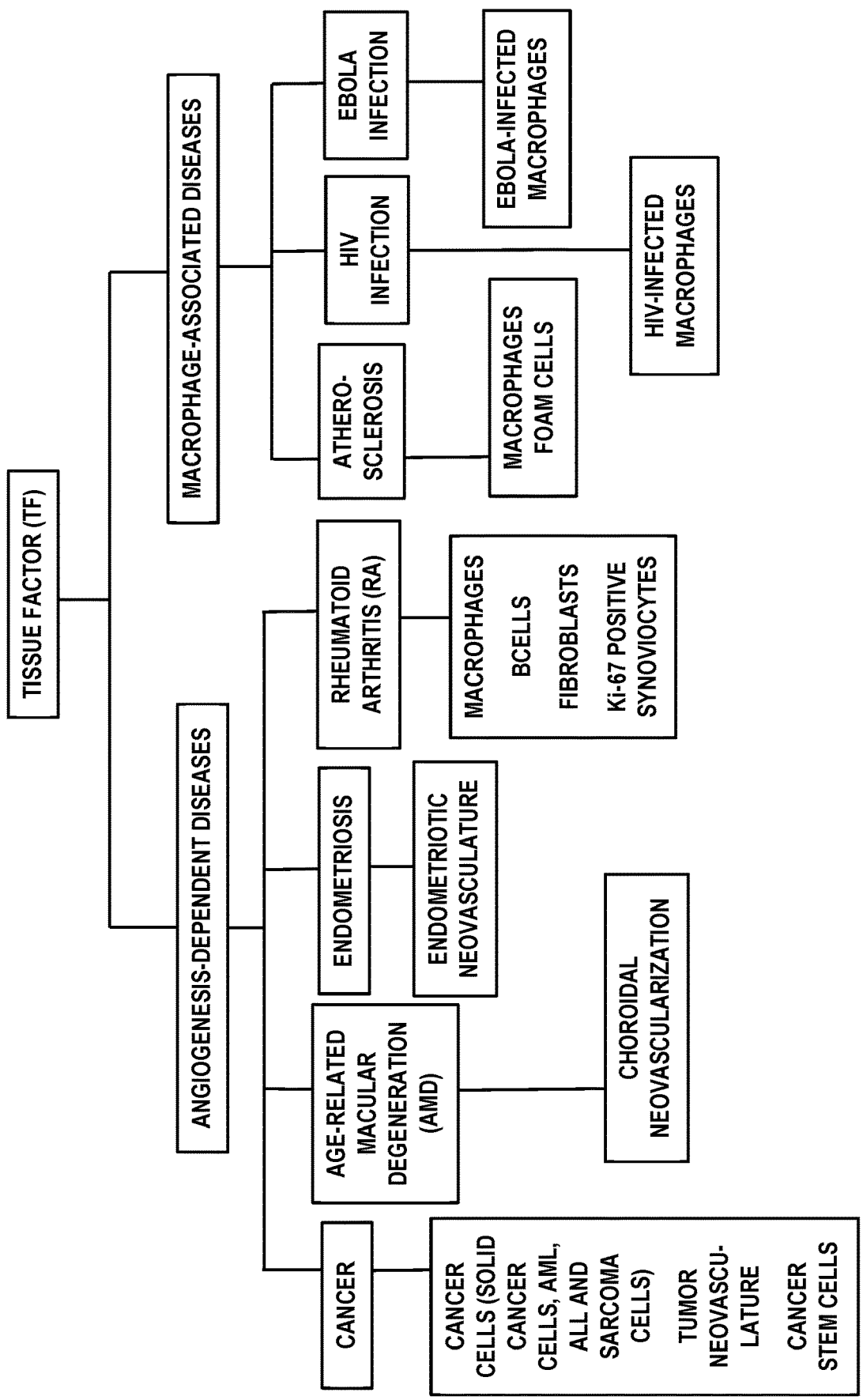
FIG. 11 is a flow chart examples of selective expression of tissue factor in angiogenesis-dependent human diseases as well as macrophage-associated human diseases.

ICON has a relatively large molecular weight (210 kDa), which can limit its ability to penetrate into tumor tissues. In order to make ICON smaller in molecular weight (MW) and safer (depletion of its coagulation activity) for immunotherapy, a second-generation ICON, referred to herein as L-ICON1 (GenBank accession no. KX760097), was designed, which consists of only the light chain (1-152 aa) of fVII fused to IgG1Fc (FIG. 1a). The molecular weight of L-ICON1 is about 100 kDa (for better penetration into tumor microenvironment), which is only two-thirds of the molecular weight of an IgG1 antibody and more than 50% reduction than ICON (FIG. 1b); L-ICON1 does not have any coagulation activity (safer in vivo) (FIG. 7 and Table 1), whereas the first generation ICON with a mutation at coagulation active site (K341A) still remains 5% coagulation activity of FVIIa (FIG. 7 and Table 1). L-ICON1 is more effective than ICON for treating triple negative breast cancer in an orthotopic mouse model.

Herein disclosed is a third generation TF-targeting ICON protein (ICON), referred to herein as L-ICON3 and ICON3, in which Factor VII (fVII) light chain or full length fVII with K341A is fused to an IgG3 Fc (FIG. 1a) by recombinant DNA technology. It is shown in FIG. 1 that the third generation L-ICON3 and the second generation L-ICON1 have similar binding activities to cells expressing Tissue Factor (TF), such as cancer cells, but L-ICON3 can initiate stronger ADCC cytotoxicity to cancer cells than second generation L-ICON1 in vitro.

Disclosed herein is the amino acid sequence of SEQ ID NO: 2, which represents L-ICON3. Also disclosed is SEQ ID NO: 1, which is a nucleic acid encoding L-ICON3.

Disclosed herein is the amino acid sequence of SEQ ID NO: 3, which represents ICON3. Also disclosed is SEQ ID NO: 4, which is a nucleic acid encoding ICON3.

Human IgG3 displays the strongest effector functions of all IgG subclasses but has a short half-life for unresolved reasons. IgG3 binds to IgG-salvage receptor (FcRn), but FcRn-mediated transport and rescue of IgG3 is inhibited in the presence of IgG1 due to intracellular competition between IgG1 and IgG3. This has been shown to occur because of a single amino acid difference at position 435, where IgG3 has an arginine instead of the histidine found in all other IgG subclasses. Therefore, to increase the half-life of L-ICON3 protein in vivo in blood circulation, an R435H mutation can be introduced to the IgG3 Fc domain of L-ICON3 by site-directed mutagenesis procedure. (Kim et al. 1999; Stapleton et al. 2011).

It is important to note that the binding of Factor VII light chain of L-ICON3 to tissue factor does not cause disseminated intravascular coagulation. L-ICON3 therefore does not initiate blood clotting (similar to that of fVII light chain in L-ICON1; see FIG. 7 and Table 1).

All third (L-ICON3 and ICON3) and fourth (L-ICON4 and ICON4) ICONs can be administered to a subject in need thereof. Administration may be local or systemic, depending upon the type of pathological condition involved in the therapy. Administration can be via any method known in the art such as, for example, intravenous, intramuscular, intratumoral, subcutaneous, intrasynovial, intraocular, intraplaque, or intradermal injection of the purified recombinant immunoconjugate protein or of a replication-deficient adenoviral vector, adeno-associated virus (AAV) or other viral vectors carrying a cDNA encoding a secreted form of the immunoconjugate.

TF-targeting ICONs can be used as a stand-alone therapy and in combination with surgery, radiotherapy, chemotherapy, other therapeutic antibodies, antibody-drug conjugates, immune checkpoint blockades, chimeric antigen receptor (CAR)-T and NK cells, dendritic cells, vaccines, oncolytic viruses, cytokines and/or depletion of immune suppressor cells like myeloid-derived suppressor cells (MDSC), regulatory T cells (Treg), tumor-associated macrophages (TAM), etc. The combination immunotherapy can target different molecules on some or all major tumor compartments, including but not limited to the cancer cells, tumor neovasculature, cancer stem cells, MDSC, Treg and TAM, or ideally, target the same molecule that is commonly expressed by these major tumor compartments.

Other routes of administration can be parenteral administration of fluids, and the like. The subject can be treated by intravenous or intratumoral injection, or injection at other sites, of one or more immunoconjugate proteins, or by intravenous or intratumoral injection, or injection at other sites, of one or more expression vectors carrying a cDNA encoding a secreted form of one or more types of immunoconjugate proteins. In some embodiments, the subject can be treated by intravenous or intratumoral injection of an effective amount of one or more replication-deficient adenoviral vectors, or one or more adeno-associated vectors carrying cDNA encoding a secreted form of one or more types of immunoconjugate proteins. Many typical embodiments involve intratumoral and/or intramuscular injections of effective amounts of a vector encoding a secreted form of an immunoconjugate.

The amount of L-ICON3 necessary to bring about the therapeutic treatment is not fixed per se, and necessarily is dependent on the concentration of ingredients in the composition administered in conjunction with a pharmaceutical carrier, adjunct compounds in the composition administered that enhance the immune system response more fully illustrated below, and the age, weight, and clinical condition of the patient to be treated. Preferred compositions deliver immunoconjugate(s) in effective amounts without producing unacceptable toxicity to the patient.

Pharmaceutical compositions or formulations of the invention may also include other carriers, adjuvants, stabilizers, preservatives, dispersing agents, and other agents conventional in the art having regard to the type of formulation in question.

As applied to cancer, the invention employs immunoconjugates having a targeting domain that specifically targets human tumor cells, CSCs or tumor vasculature endothelial cells, or all three tumor compartments, and an effector domain that activates a cytolytic immune response or cytotoxic effect against the targeted cells.

In cancer treatments, anti-tumor immunoconjugates are used for treating and preventing a variety of cancers (solid cancer, leukemia and lymphoma), particularly primary or metastatic solid tumors, including melanoma, renal, prostate, breast, ovarian, brain, neuroblastoma, head and neck, pancreatic, bladder, and lung cancer. The immunoconjugates may be employed to target the tumor vasculature, particularly vascular endothelial cells, CSCs and/or tumor cells. The tumor vasculature offers several advantages for immunotherapy, as follows. (i) Some of the vascular targets including tissue factor should be the same for all tumors. (ii) Immunoconjugates targeted to the vasculature do not have to infiltrate a tumor mass in order to reach their targets. (iii) Targeting the tumor vasculature should generate an amplified therapeutic response, because each blood vessel nourishes numerous tumor cells whose viability is dependent on the functional integrity of the vessel. (iv) The vasculature is unlikely to develop resistance to an immunoconjugate, because that would require modification of the entire endothelium layer lining a vessel. Unlike previously described anti-angiogenic methods that inhibit new vascular growth, L-ICON3 can elicit a cytolytic response to the neovasculature. It is noted that the compositions disclosed herein can specifically treat metastatic cancer, or can prevent cancer from metastasizing.

L-ICON3 can also be effective for treating patients with rheumatoid arthritis, the exudative ("wet") form of macular degeneration, endometriosis, viral infections, atherosclerosis, thrombogenesis, and other diseases associated with neovascularization.

In one embodiment, a photosensitizer or a drug can be coupled to L-ICON3 for TF-targeting photodynamic therapy (PDT) or antibody-drug conjugate (ADC) therapy. Photosensitizers that can be conjugated to the targeting molecule include photodynamic dyes. The dye should be capable of causing damage to the targeted tissue after exposure to the appropriate type of radiation, e.g., light of a certain wavelength, typically between about 630 nm and about 750 nm. Any of a number of available photodynamic dyes can be used, such as those described in U.S. Pat. Nos. 6,693,093 and 6,443,976, which include hematoporphyrins, including derivatives thereof such as dihematoporphyrin ethers and dimer and trimers of hematoporphyrins (examples of which are described in U.S. Pat. Nos. 4,968,715 and 5,190,966), and improvements thereon, examples of the latter being described in U.S. Pat. Nos. 5,028,621, 4,866,168, 4,649,151 and 5,438,071; aminolevulinic acids (precursors to hematoporphyrin) as sources of photodynamic compounds, as described and exemplified in U.S. Pat. No. 5,079,262; porphyrins, including boronated porphyrin, benzoporphyrin, and derivatives thereof, and as further exemplified by the green porphyrins described in U.S. Pat. Nos. 4,883,790, 4,920,143, 5,095,030 and 5,171,749; merocyanines; porphycenes; porfimer sodium; verteporfin (Vysudine™, CIBA Vision); Photofrin II™; PH-10™; chlorins, as exemplified by meso-tetra(hydroxyphenyl)-chlorin and bacteriochlorins, the latter exemplified in U.S. Pat. Nos. 5,171,741, 5,173,504; zinc phthalocyanine, as described in U.S. Pat. No. 5,166,197; purpurins, such as tin ethyl etiopurpurin (SnET2™, Miravant); pheophorbides, examples of which are described in U.S. Pat. Nos. 5,198,460, 5,002,962 and 5,093,349; and monoclonal antibody-dye conjugates of each of the foregoing, and, optionally; mixtures of any or all of the foregoing.

Although described above with reference specific to compounds, one can also utilize enantiomers, stereoisomers, metabolites, derivatives and salts of the active compounds. Methods for synthesis of these compounds are known to those skilled in the art. Examples of pharmaceutically acceptable salts include, but are not limited to, mineral or organic acid salts of basic residues such as amines, and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Conventional non-toxic salts include those derived from inorganic acids such as hydrochloric, hydrobromic, sulfuric, sulfamic, phosphoric and nitric acid; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, methanesulfonic, ethane disulfonic, oxalic and isethionic acids. The pharmaceutically acceptable salts can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed. (Mack Publishing Company, Easton, Pa., 1985, p. 1418).

A prodrug is a covalently bonded substance which releases the active parent drug in vivo. Prodrugs are prepared by modifying functional groups present in the compound in such a way that the modifications are cleaved, either in routine manipulation or in vivo, to yield the parent compound. Prodrugs include compounds wherein the hydroxy or amino group is bonded to any group that, when the prodrug is administered to a mammalian subject, cleaves to form a free hydroxyl or free amino, respectively. Examples of prodrugs include, but are not limited to, acetate, formate and benzoate derivatives of alcohol and amine functional groups.

It is further contemplated that additional modifications could be made to L-ICON3 as represented by SEQ ID NO: 2. For example, a modified L-ICON3 can be made that exhibits at least one functional activity that is comparable to the unmodified version, yet the modified protein or polypeptide possesses an additional advantage over the unmodified version, such as cheaper to production, eliciting fewer side effects, and/or having better or longer efficacy or bioavailability.

Modified L-ICON3 can possess deletions and/or substitutions of amino acids; thus, a protein with a deletion, a protein with a substitution, and a protein with a deletion and a substitution are modified proteins. In some embodiments these modified proteins may further include insertions or added amino acids, such as with fusion proteins or proteins with linkers, for example.

Substitutional or replacement variants typically contain the exchange of one amino acid for another at one or more sites within the polypeptide and may be designed to modulate one or more properties of the polypeptide, particularly its effector functions and/or bioavailability. Certain specific amino acid exchanges in chimeric polypeptides of the embodiments are detailed above. Further substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

In addition to a deletion or substitution, a modified polypeptide may possess an insertion of residues, which typically involves the addition of at least one residue in the polypeptide. This may include the insertion of a targeting polypeptide or simply a single residue. Terminal additions, called fusion proteins, are discussed below.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

EXAMPLES

Example 1: L-ICON3 and ICON3

As shown in FIG. 1a, the third generation (3rd GEN) ICONs, namely L-ICON3 and ICON3, are composed of fVII light chain (1-152aa) or full length (406 aa with K341A mutation) fused to human IgG3 Fc domain. The mRNA sequences of L-ICON3 (SEQ ID NO: 1) and ICON3 (SEQ ID NO: 3) have been deposited to GenBank (accession no. KY223609 and KY223610, respectively).

The Molecular Weights (MW) of L-ICON3 and ICON3

The monomer of L-ICON3 peptide contains 419 amino acid residues (SEQ ID NO: 2). The monomer L-ICON3 protein weighs 47 kilodaltons. The estimated molecular weight for dimeric L-ICON3 is 94 kDa. The actual molecular weight of L-ICON3 in SDS-PAGE is about 100 kDa (FIG. 1b). The Fc portion in L-ICON3 was further verified by Western blotting using anti-human IgG antibody for detection (FIG. 1c).

The monomer of ICON3 peptide contains 673 residues starting "MVSQALRLLC" (SEQ ID NO: 4). The estimated monomer ICON3 protein weighs 75 kDa.

The Methods of Affinity Purification of L-ICON3 and ICON3

Figure 2:
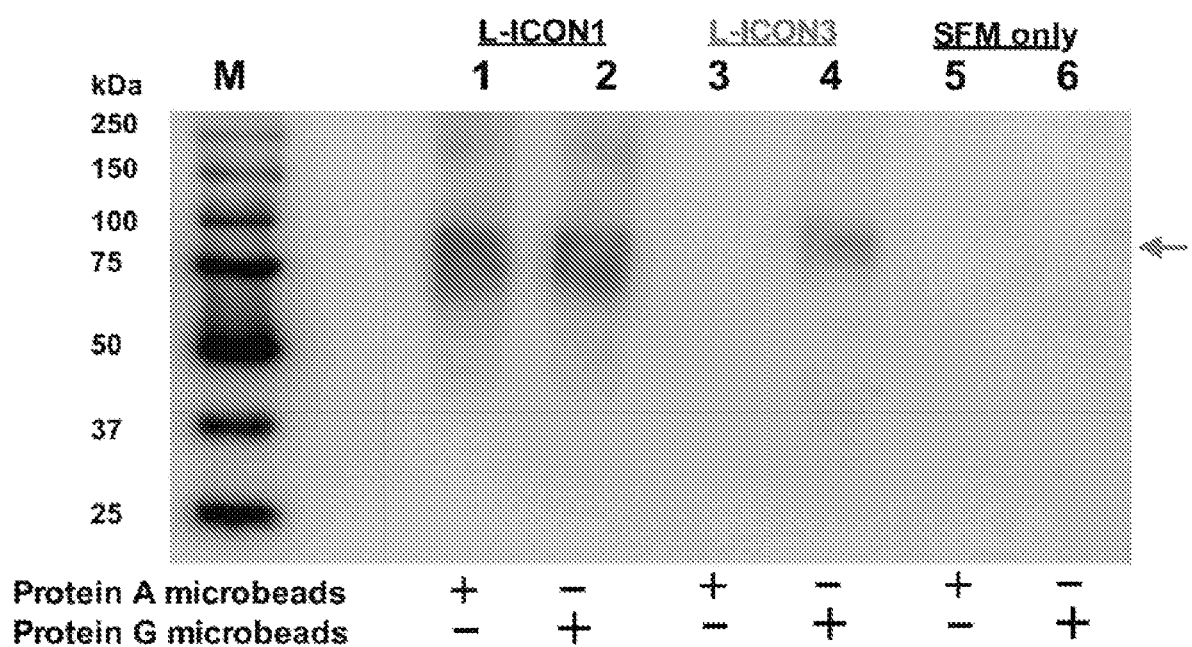
FIG. 2 shows the differences of affinity purification between recombinant L-ICON1 and L-ICON3 proteins. One ml of serum free medium (SFM4CHO) supplemented with 1 µg/ml Vitamin K1 (Sigma) from CHO producer cells for L-ICON1 or L-ICON3 was incubated with Protein A or Protein G magnetic microbeads (Bio-Rad) and the captured protein was eluted in 1×SDS loading buffer and was analyzed by SDS-PAGE followed by Western blotting using 1:10,000 diluted anti-human IgG HRP conjugate (Sigma) and ECL reagents (Peirce). Fresh serum free medium (SFM) without L-ICON protein was used as negative medium control.

To develop a method for affinity purification of L-ICON3 and ICON3, an immune-precipitation Western blotting (IP-WB) was performed. The results in FIG. 2 showed that L-ICON3 protein could only be purified by Protein G affinity column, whereas L-ICON1 could be purified by Protein A and Protein G affinity columns. Similarly, ICON3 can be purified by Protein G affinity column.

Binding Activity of L-ICON3 Protein to Human and Murine Cancer Cells

Figure 3A:
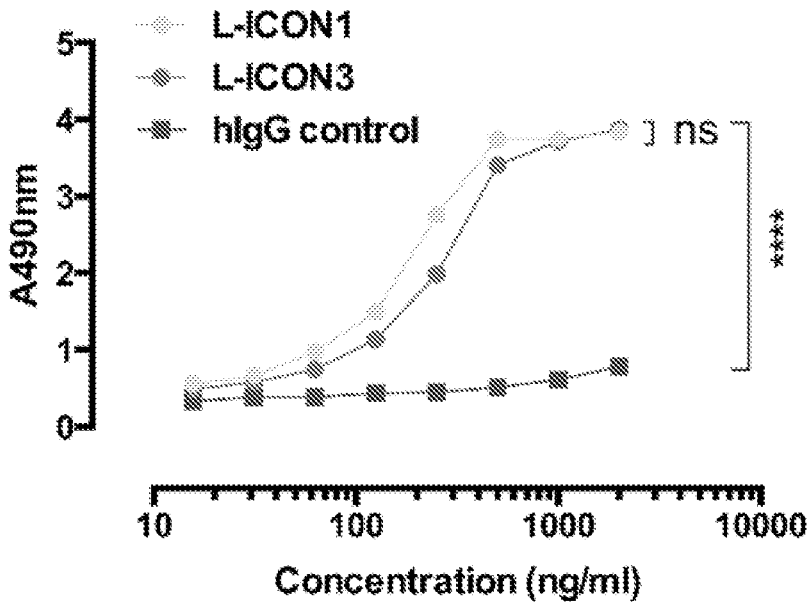
FIG. 3A-3F shows L-ICON3 protein can bind both murine and human cancer cells, which allows for the translation from animal studies into human clinical trials and suggests that L-ICON3 therapy has therapeutic potential to treat a variety of solid cancers. (ns: Not significant).
Figure 3B:
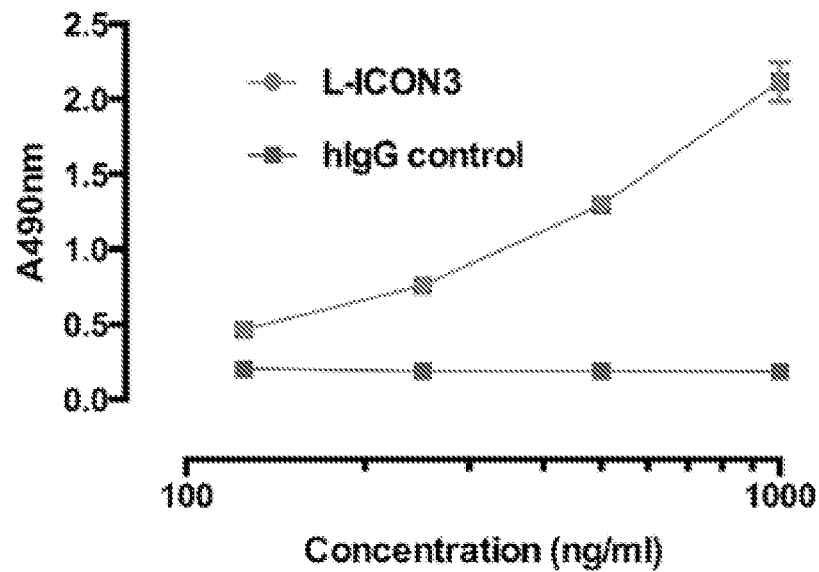
Figure 3C:
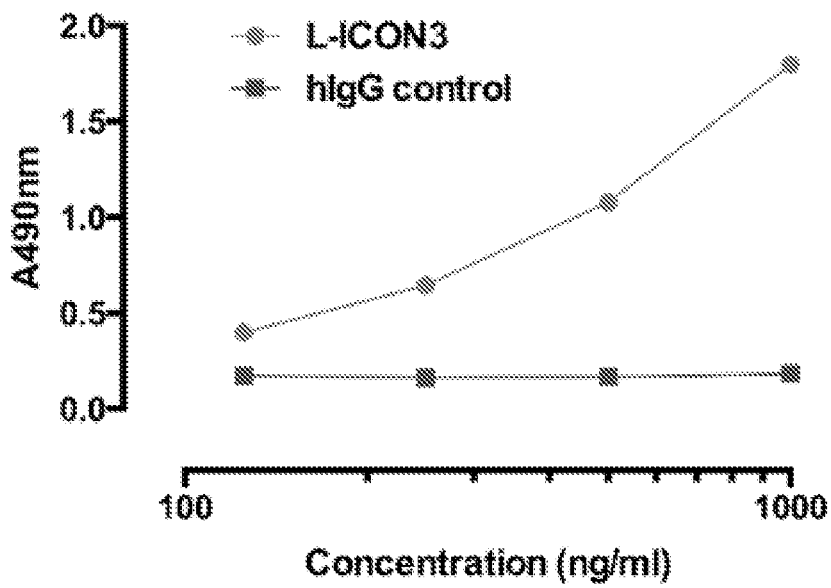
Figure 3D:
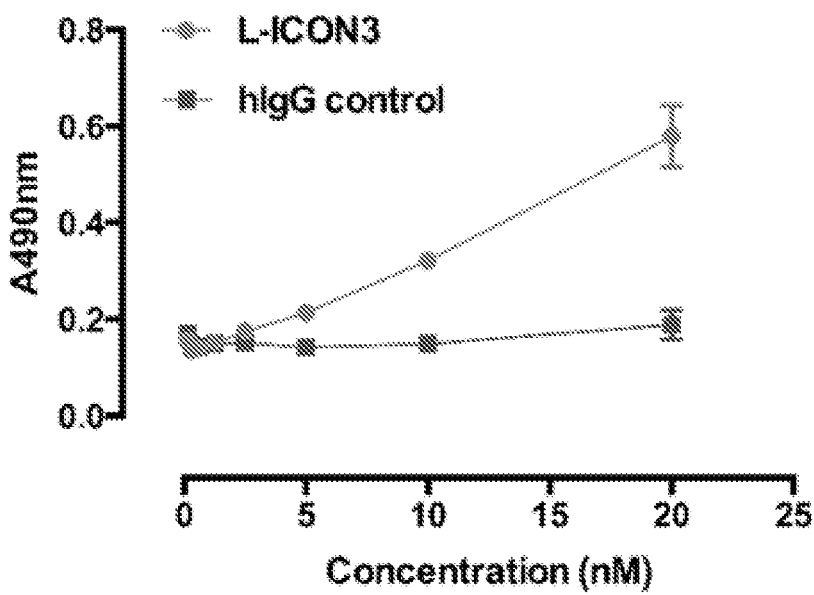
Figure 3E:
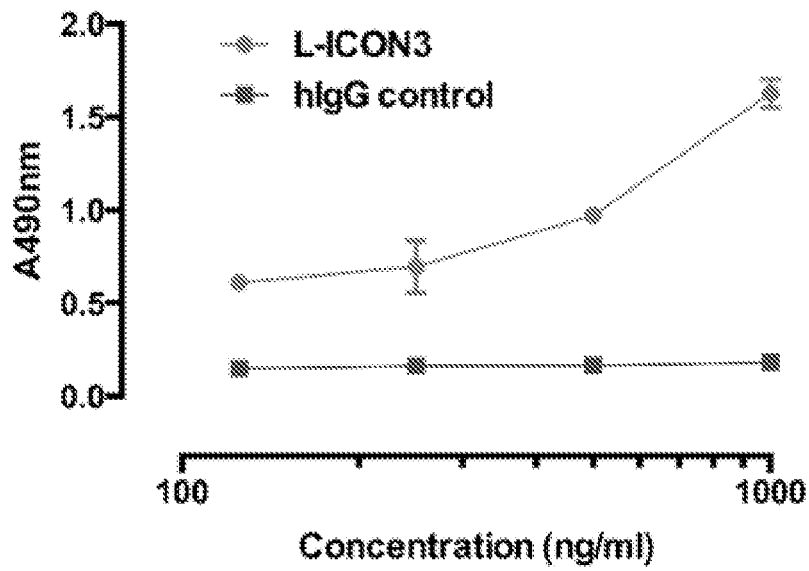
Figure 3F:
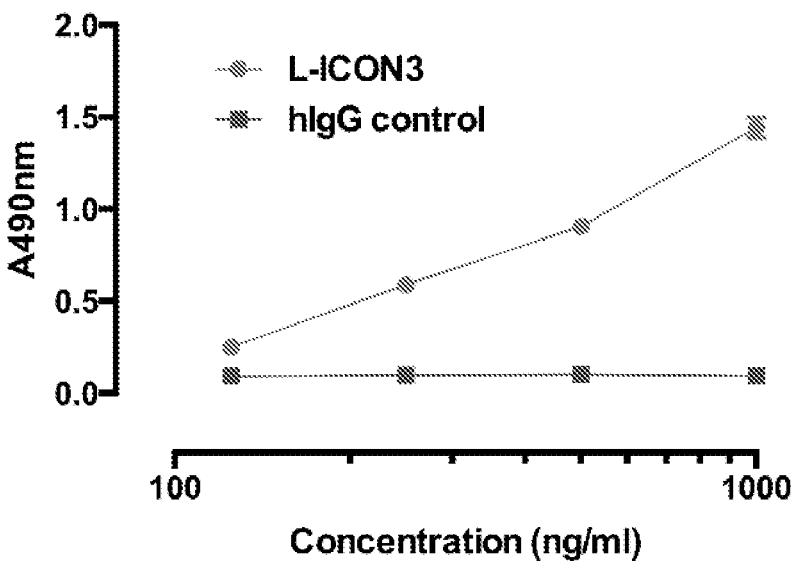

The binding activity of L-ICON3 was compared to that of L-ICON1 in cancer cell ELISA using a high TF expressing human triple-negative breast cancer line MDA-MB-231. The results in FIG. 3a showed that L-ICON3 and L-ICON1 could equally bind to MDA-MB-231 cells (ns, not significant). The cancer cell ELISA results further showed that L-ICON3 could bind human TNBC (MDA-MB-231 in FIGS. 3a and 3b), melanoma (SK-Mel-28 in FIG. 3c) and ovarian cancer (OVCARS in FIG. 3d) as well as two very aggressive murine cancer lines, including murine TNBC (4T1 in FIG. 3e) and melanoma (B16F10 in FIG. 30.

L-ICON3-Dependent ADCC and CDC Effects in Killing Cancer Cells

Figure 4A:
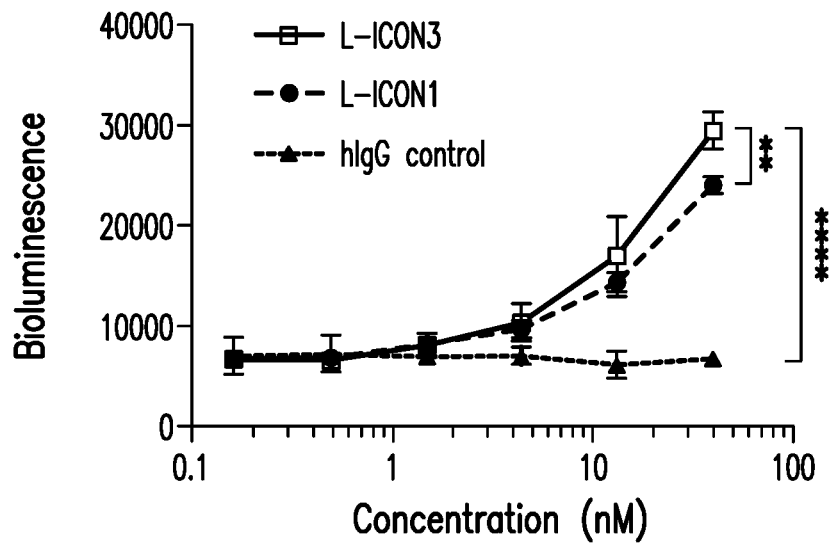
FIGS. 4A and 4B shows L-ICON3 can initiate ADCC and CDC (complement-dependent cytotoxicity) to kill target cancer cells.
Figure 4B:
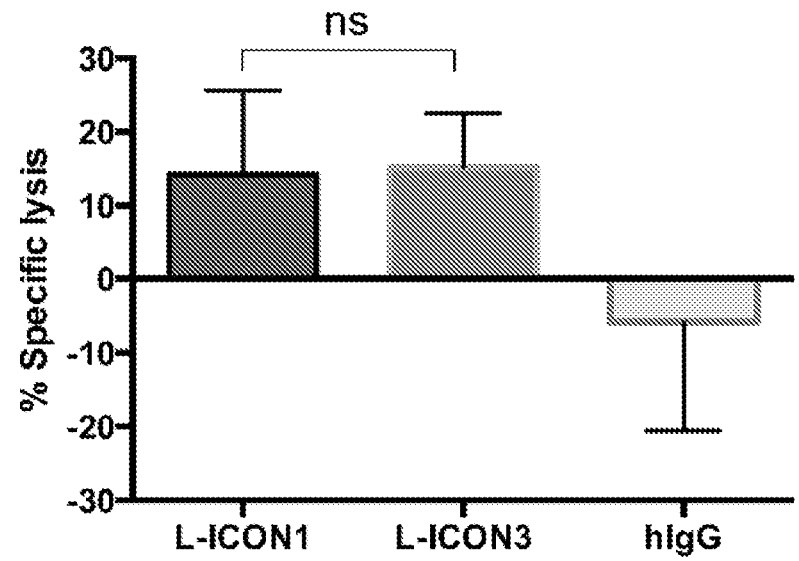

The results in FIG. 4a showed that L-ICON3 protein could initiate ADCC to kill target cancer cells (human ovarian cancer OVCARS cells). In fact, L-ICON3-dependent ADCC had stronger effect than 2nd GEN ICON (L-ICON1) did (FIG. 4a). The results in FIG. 4b showed that L-ICON3 can initiate complement-dependent cytotoxicity to kill target cancer cells (MDA-MB-231 cells) and the effect was similar to that of L-ICON1 (ns: not significant).

Example 2: Therapeutic Antibody-Like Immunoconjugates Against Tissue Factor with Potential to Treat Angiogenesis-Dependent Human Diseases as Well as Macrophage-Associated Human Diseases Tissue factor (TF) is a 47-kDa membrane-bound cell surface receptor (1-3). It is also known as thromboplastin, coagulation factor III or CD142. Under physiological condition, TF is not expressed by circulating peripheral blood lymphocytes (PBL) and quiescent vascular endothelial cells. TF expression is restricted to the cells that are not in direct contact with the blood, such as pericytes, fibroblasts and smooth muscle cells, which are localized in the sub-endothelial vessel wall and is sequestered from circulating coagulation factor VII (fVII). In these cells, the majority of TF is localized in intracellular pools (4). Upon disruption of vessel wall integrity, TF in pericytes and smooth muscle cells is released and can be bound by fVII, leaking from blood circulation, to initiate blood coagulation in order to stop bleeding (5, 6). Besides its role as the primary initiator of coagulation, TF is also a modulator of pathological angiogenesis (7-9).

Angiogenesis, the formation of new capillaries from pre-existing vessels, is involved in both physiological conditions (such as reproduction and tissue repair) as well as in more than 20 human diseases (10), including but not limited to cancer (10, 11), age-related macular degeneration (AMD), endometriosis and rheumatoid arthritis (RA) (12-14). In cancer, angiogenesis was identified as one of the "hallmarks of cancer" by Hanahan and Weinberg (15, 16) due to the recognition that this process is of crucial importance during the transition from benign hyperplastic nodules to malignant lesions (11). Identification of target molecules specific for angiogenic vascular endothelial cells, the inner layer of pathological neovasculature, is critical for discovery and development of neovascular-targeting therapy for these angiogenesis-dependent, common human diseases.

Tissue Factor in Pathological Neovasculature of Cancer, Age-Related Macular Degeneration and Endometriosis Vascular endothelial growth factor (VEGF) plays a central role in angiogenesis-dependent cancer and non-malignant human diseases (17), such as macular degeneration (18), rheumatoid arthritis (19) and endometriosis (20). Specifically, VEGF stimulates angiogenesis by binding to VEGR receptors on VECs in the pathological neovasculature (usually micro- or capillary vessels) in those angiogenesis-dependent diseases. It is previously known that VEGF can induce TF expression on human umbilical vein endothelial cells (HUVEC), a commonly used VEC model in angiogenesis studies. Noting that although VEGF receptors are relatively expressed at higher levels on tumor VECs, they are also expressed by normal VECs (21), indicating that VEGF receptors are not specific for neovascular endothelial cells. To better mimic pathological angiogenesis, an ideal angiogenic VEC model should be derived from micro- or capillary vessels. Using vascular endothelial growth factor-induced in vitro angiogenic vascular endothelial models, it was reported that, unlike VEGFRs, TF is an angiogenic-specific receptor and the target for factor VII (fVII)-targeted immunotherapy using fVII-IgG1Fc immunoconjugate (named ICON, discussed below) and photodynamic therapy using fVII-conjugated photosensitizers (22). In addition, TF is also a unique pathological angiogenic endothelial cell-surface receptor in vivo because of its selective expression on angiogenic VECs in vivo in tumor vasculature (7, 23-27), ocular (12) and endometriotic (14) neovasculature from animal models to patients.

Tissue Factor in Pathological Neovasculature of Cancer

TF expression on tumor vascular endothelial cells was first reported by Contrino et al. in 1996 in primary tumor tissues from 7 breast cancer patients (23). Importantly, they also reported that TF expression was not detected in normal vascular endothelial cells in adjacent breast tissues. Hu and Garen independently reported that TF was selectively expressed in tumor neovasculature of human melanoma xenografts in vitro and in vivo (24, 28). It was further showed that TF was specifically expressed on the tumor vascular endothelial cells in human lung (26) and chemoresistant breast (27) tumor xenografts, but was not expressed on resting vascular endothelial cells in brain, lungs and spleen of mice (26).

Tissue Factor in the Neovasculature of Age-Related Macular Degeneration

Age-related macular degeneration (AMD) is the leading cause of blindness in the elderly population (age 55 and older) in the developed countries as well as in the developing countries. Severe loss of central vision frequently occurs with the exudative (wet) form of AMD, as a result of the formation of a pathological choroidal neovasculature (CNV) that damages the macular region of the retina. In collaboration with the Kaplan laboratory during his tenure at the University of Louisville, Bora, Hu et al reported in 2003 that the endothelial cells of the CNV membrane selectively expressed TF in a pig model (12), whereas the normal retinal vascular endothelium did not express TF. The normal choroidal endothelium also did not express TF (12). In another study, Grossniklaus et al. immunostained for VEGF and TF expression in 10 surgically-excised subfoveal CNV specimens obtained from seven women and three men ranging in age from 27 to 84 years and in 10 eye bank eyes with subfoveal CNV from four women and six men ranging in age from 74 to 99 years. They found that VEGF was variably expressed in macrophages and strongly expressed in Retinal pigment epithelium (RPE), a major component of CNV both in post-mortem eyes and surgical specimens. VEGF was also expressed in fibroblasts and photoreceptors. TF was strongly expressed in macrophages, and variably expressed in RPE. There was stronger staining for VEGF and TF in inflammatory active versus inflammatory inactive surgically excised CNV (29).

Tissue Factor in the Neovasculature of Endometriosis

Endometriosis is a gynecological disorder characterized by the presence of endometrial tissue, the inner layer of uterus, outside of the uterus. Endometrial lesions are primarily located on the pelvic peritoneum and ovary, but can also be located in the pericardium, pleura, lung, and even the brain. The disease affects up to 10% of all reproductive-aged women and the prevalence rises to 20-50% in infertile women. Dr. Lockwood laboratory has extensively examined the expression of TF on in endometriosis (30-33). In normal endometrium, TF expression is limited to stromal cells of the secretory phase with far lower expression in glandular epithelium. In endometriosis, however, TF is greatly overexpressed in both glandular epithelium and stromal cells. Interestingly, the most intense TF immunostaining was observed on macrophages in endometriotic tissues. In 2010, in collaboration with Lockwood group Krikun, Hu et al. reported that the endothelial cells in ectopic endometriotic lesions highly expressed TF (14), whereas no TF was detected on gland cells, stromal cells, endothelial cells and vessel walls in eutopic proliferative endometrium from patients (14).

Tissue Factor Expression in Cancer

Tissue Factor Expression on the Cancer Cells of Solid Cancers, Leukemia and Sarcoma In addition to its expression on tumor neovasculature, TF is also highly expressed on the cancer cells in many types of solid cancers (34-36) and leukemia (AML and ALL) (36). For example, TF expression is detected on the cancer cells in 80%-100% of breast cancer patients, 40%-80% of lung cancer patients and 84% of ovarian cancer patients (36). Similar to the cancer of breast, lung and ovary, TF is also expressed at high percentages in many other human solid cancers (36, 37), for instance, 95% in primary melanoma and 100% in metastatic melanoma, 53%-90% in pancreatic cancer, 57%-100% in colorectal cancer, 63%-100% in hepatocellular carcinoma, 60%-78% in primary and metastatic prostate cancer and 47%-75% in glioma.

Leukemia is a malignant neoplasm of hematopoietic tissue originating in the bone marrow and infiltrating the peripheral blood and often also the spleen, liver, and lymph nodes. Acute leukemia, including AML and ALL are characterized by proliferation of immature cells or blasts. If untreated, death usually occurs within 6 months in most cases. ALL is the most common childhood malignancy and the second most common adult leukemia, and AML is the second most common childhood malignancy. It was reported that TF is expressed on the human leukemic HL-60 (38-42), Molt-4 (43), THP-1 (43) cell lines, and on leukemic cells from patients with AML (38, 44-48) and ALL (39, 49). TF is not expressed on the normal peripheral mononuclear cells unless stimulated by endotoxin or other cytokines (41), nor on myeloid precursor cells (45). TF was also detected in the plasma of patients with leukemia (39, 49) and in HL-60 culture medium (39).

In sarcoma, TF expression was also detected on mouse Meth-A sarcoma cells (50), rat osteosarcoma cells(51) and vascular origin of Kaposi's sarcoma (52). It remains to investigate if TF is expressed in human sarcoma.

Tissue Factor Expression on Cancer Stem Cells

Besides the cancer cells and tumor neovasculature, cancer stem cell (CSC) is also an important tumor compartment in tumor microenvironment. CSC contributes to tumor angiogenesis, resistance to multiple therapies (53, 54) and metastasis (53, 55, 56). Targeting CSC therapy can treat cancer at the root and may overcome the drug resistance, recurrence and metastasis. It has been shown that TF is also expressed on CD133+ and CD24−CD44+ cancer-initiating stem cells and TF can serve as a novel oncotarget for CSCs, isolated from human cancer cell lines (such as breast, lung, ovarian, head and neck cancer), tumor xenografts and breast cancer patients. Furthermore, TF-targeting immunotherapy agent ICON can eradicate CSCs without drug resistance (37).

Taken together, it appears that TF is a common yet selective therapeutic target in cancer for the cancer cells, tumor neovasculature and cancer stem cells and that TF-targeting therapies represent novel therapeutic approaches with ability to selectively and effectively target and eliminate these three major tumor compartments. These finding may explain the observations of ICON's remarkable effects without recurrence and drug resistance, i.e., complete eradication of well-established primary tumor (up to 600 mm$^3$) and metastases in mouse models of human and murine prostate, melanoma and head and neck cancer (25, 28, 57).

Tissue Factor in Rheumatoid Arthritis

Rheumatoid arthritis (RA) is a chronic, often progressive, systemic inflammatory condition of unknown cause. It is characterized by a mononuclear infiltration (T cells, B cells, plasma cells and macrophages) into the synovial tissue, and a symmetric, erosive arthritis of peripheral joints, but it may also cause systemic manifestations. Tumor necrosis factor α (TNFα) plays an important role in the pathogenesis of RA (58).

TF Expression in Arthritic Joints

Busso et al (59) immunohistochemically stained synovial tissue specimens from 10 RA patients and reported that TF expression was detected in fibroblasts, smooth muscle cells, and macrophages, but not in endothelial cells. Chen et al. (60) observed TF expression on Ki-67 positive synoviocytes, B cells and endothelial cells. The controversial results regarding TF expression on endothelial cells in RA could be due to the time point at which TF expression was evaluated. It has been shown that induction of TF by TNFα on endothelial cells (HMVEC and HUVEC) was transient with a peak at 4-6 hours after incubation with TNFα. Thus, it appears that upon stimulation of pro-inflammatory cytokines and growth factors, endothelial cells express TF in the early stage of RA (acute phase) and then endothelial TF expression may decrease or even disappear in later stages of RA (chronic phase). Therefore, TF is expressed by macrophages, B cells, Ki-67 positive synoviocytes and angiogenic VECs in RA.

Angiogenesis and Angiogenic Endothelial TF in RA.

RA is also associated with angiogenesis, which enables leukocyte transendothelial migration into the inflamed synovial tissue (10, 61-70). There are numerous angiogenic mediators, such as TNFα and VEGF, and endogenous inhibitors in the RA synovium with an imbalance yielding to increased capillary formation in arthritis. Specifically, vascular endothelial cells (VECs) are involved in a number of mechanisms underlying synovial inflammation (71). Angiogenic VECs are responsible for increased vascular permeability, leukocyte extravasation (a key feature of inflammation), and secretion of numerous inflammatory mediators during the initiation and progression of RA. And anti-angiogenesis has been tested for treatment of RA (61). Many pro-inflammatory cytokines and growth factors such as TNFα, IL-1 and VEGF are known stimuli for induction of TF on VECs (72). Thus angiogenic VECs can serve as a target for TF-targeting therapy of RA.

Macrophages in RA Expressing TF.

It is well documented that macrophages play several roles in RA initiation and progression. First, macrophages can serve as one of the antigen presenting cells to abnormally present self-antigen leading to activation of autoreactive T cells. Second, macrophages produce and secrete pro-inflammatory cytokines, chemokines, growth factors and enzymes, such as TNFα, IL-1, IL-6, IL-18, IL-15 and IL-32, to further activate other cells, contributing to disease progression. Third, macrophages stimulate synoviocytes to release enzymes, such as collagenases and proteases, which may lead to cartilage and bone damage. Targeting macrophage represents a novel therapeutic approach for the treatment of RA. It has been documented that TF is expressed by macrophages in rheumatoid synovium (59, 60). Importantly, TF is not normally expressed by unstimulated monocytes (73, 74), but TF can be induced on monocytes by inflammatory mediators including bacterial LPS (75), TNFα (76) and IL-1 (77).

Fibroblasts in RA Expressing TF.

It is documented that TF is expressed on human fibroblast lines (78, 79) and human embryonic fibroblasts (80). Synovial fibroblasts are involved in the pathogenesis of RA via secreting a wide range of cytokines, chemokines, growth factors and enzymes such as MMPs. Studies have shown that inhibiting the growth of synovial fibroblasts could reduce the severity of inflammatory arthritis (81). Thus, targeting fibroblast via binding to TF can lead to development of novel therapeutic agents for the treatment of RA.

B Cells in RA Expressing TF.

B cells are another type of infiltrating immune cells in arthritic joints in RA. B cells play an important role in the pathogenesis of RA, not only serving as the precursors of auto-antibody producing plasma cells, but also being involved in antigen presentation, T cell activation and cytokine production (82). Thus, B cell-directed therapy may provide therapeutic effect in the treatment of RA (83-85). A recent study showed that B cells in human RA express TF (60), whereas normal B cells do not express TF (86). The reason why RA-associated B cells express TF is still unknown. It could be due to induction by one or a mixture of inflammatory cytokines and chemokines. As evidence, a subpopulation (CD19+CD79b+CD38+CD40+CD5−) of normal human B cells, representing 30% of total B cells, expressed TF after induction by phorbol myristate acetate (PMA) (86, 87). Interestingly, T cells and NK cells do not express TF even after stimulation via LPS or PMA (86). It was observed that NK cell is the major effector cell to mediate ADCC effect of TF-targeting ICON immunotherapy in vitro and in vivo in an animal model of cancer (57). The finding of negative TF expression on NK cells is very important not only to better understand the efficacy, but also to ensure the safety of TF-targeting immunoconjugates in clinical trials.

Cytokines and Growth Factors in RA, Endometriosis and Tumor Microenvironment Contributing to Induction of TF and Angiogenesis (Hu. *Antibodies*. 2018 In press). Many cytokines and chemokines are present in rheumatoid synovium (88) and/or in the plasma of RA patients (89-91), including pro-inflammatory cytokines (e.g., IL-1, IL-6, TNF1996</Year> <RecNum>88</RecNum> <IFNn, GM-CSF, etc), anti-inflammatory cytokines (IL-10, IL-1Rα, TGFβ, IL-11, IL-13, etc), chemokines (e.g., IL-8, MIP-1L-8, MIP-1P-1P-110etc) and growth factors (e.g., VEGF, PDGF, FGF). Some of these stimuli can contribute to angiogenesis and increased vascular permeability of VECs (e.g., VEGF) (19) and/or to induction of TF on VECs (e.g., TNF</A(92) or on monocytes (LPS) (75), TNFN (76) and IL-1 (77). Some of them, for example, VEGF, a potent growth factor, play a central and common role in angiogenesis-dependent cancer and non-malignant human diseases (17), such as AMD (18), RA (19) and endometriosis (20).

Tissue Factor in Macrophage-Involved Human Diseases
Tissue Factor in Atherosclerosis Atherosclerosis is a progressive disease characterized by the accumulation of lipids in medium to large sized arteries, such as coronary arteries. During atherosclerosis, formation of atherosclerotic plaques in the vessel wall results in narrowing of the lumen of the artery. Atherosclerosis and subsequent atherothrombosis is the leading cause of death in the world. Atherosclerotic plaques are highly procoagulant largely due to the high levels of TF, which is expressed on macrophages and vascular smooth muscle cells in the plaques as well as on microvesicles (also known as microparticles or extracellular vesicles) and foam cell-derived debris within the necrotic core. Interestingly, over 90% microvesicles within plaques are CD14 positive (93), suggesting their origin of monocyte/macrophage. Several groups including Mackman's group have elegantly reviewed TF in atherombosis and atherosclerosis (94-99). Animal models of atherosclerosis have been developed in mice, rabbits, swine and non-human primates, of which mice and rabbits are the most commonly used models. Importantly, similar to the atherosclerosis in humans, high levels of TF are also present in atherosclerotic lesions in rabbit models and in the Apoe$^{-/-}$ mouse model (see the review by Tatsumi and Mackman) (95). The findings of TF expression in these animal models are very important. This is because it provides not only animal models mimicking the progression of atherosclerosis in humans for basic science research, but also provides animal models for testing TF-targeting therapeutic agents for the treatment of atherosclerosis in humans. In addition, patients with hyperlipidemia and type II familial hypercholesterolemia have elevated levels of TF-expressing monocytes and TF positive microvesicles. Importantly, TF is not normally expressed by unstimulated monocytes (73, 74), but TF can be induced on monocytes by inflammatory mediators including bacterial lipopolysaccharide (LPS, also known as endotoxin) (75), TNFα (76) and IL-1 (77).

Tissue Factor Expression on HIV-Infected Macrophages

Rapidly after the discovery of the human immunodeficiency virus-1 (HIV-1), it was found that HIV-1 has two types of major target cells in peripheral blood in vivo, namely T lymphocytes, which have been extensively studied, and macrophages(100, 101), which have been neglected but deserve to be extensively investigated based on the observations described below. While the viral replication cycle is usually rapid and cytopathic in T cells, infected macrophages survive for months in vitro and in vivo and accumulate large vacuoles containing infectious viral particles. As a result, HIV genes are actively expressed and viral particles are assembled in HIV-infected macrophages(100). Thus macrophages play a critical role in the pathogenesis of HIV infection for early stage viral transmission and dissemination within the host and more importantly, as a reservoir of virus persistence. In addition, macrophages in chronic HIV infection selectively express a cell membrane receptor tissue factor (TF)(102). However, TF is not normally expressed by unstimulated monocytes(73) and other quiescent blood cells and vascular endothelial cells in blood vessel walls(24, 25, 103-105). Elevated TF on macrophages contributes to increased risk of in vivo coagulation, i.e., arterial and venous thrombosis, a common adverse effect in HIV patients after highly active antiretroviral therapy (HAART)(102). In addition, the level of macrophage TF was correlated with the HIV level in plasma(102). TF expression could be induced on monocytes by bacterial lipopolysaccharide (LPS)(102), which is a bacterial product probably derived from the gastrointestinal tract and has high circulating levels in chronically HIV-infected individuals (106). Thus, HIV-infected macrophages are considered to be a reservoir for spreading virus and contribute to increased risk of intravascular thrombosis due to tissue factor expression.

Tissue Factor Expression in Ebola-Infected Macrophages

Ebola virus can cause acute mortality about 80% in outbreaks in humans and nearly 100% in monkey models, due to severe hemorrhagic fever. The mechanism underlining coagulation abnormalities in Ebola hemorrhagic fever is that Ebola virus can induce TF expression in primate monocytes and macrophages during viral replication (107). Blockage of fVIIa/TF by a recombinant nematode anticoagulant protein c2 (rNAPc2) reduced the level of TF activity and significantly increased the survival of treated non-human primates in a rhesus macaque model of Ebola hemorrhagic fever (108).

Tissue Factor is not Expressed by T and Natural Killer (NK) Cells

Interestingly, T cells and NK cells do not express TF even after stimulation via LPS or PMA (86). We previously observed that NK cell is the major effector cell to mediate antibody-dependent cell-mediated cytotoxicity (ADCC) effect of TF-targeting ICON immunotherapy in vitro and in vivo in an animal model of cancer (57). The finding of negative TF expression on NK cells is very important not only to better understand the efficacy, but also to ensure the safety of TF-targeting immunoconjugates in clinical trials. As discussed above, TF is not normally expressed by unstimulated monocytes (73, 74) and B cells (86), but TF can be induced on monocytes by inflammatory mediators including LPS (75), TNFα (76) and IL-1 (77) and on B cells by PMA (86, 87).

Targeting TF Antibodies and Antibody-Like Immunoconjugates in Preclinical Studies
Second and Third Generations of TF-Targeting Antibody-Like Immunoconjugates (L-ICONs for Lighter ICON)

To make L-ICON1 more effective, a third generation ICON was generated, named L-ICON3 (GenBank accession No. KY223609) and ICON3 (GenBank accession No. KY223610). L-ICON3 and ICON3 are composed of the fVII light chain (the first 152aa) or full length (with or without K341A) fused to an IgG3 Fc ($3^{rd}$ GEN, FIGS. 1a and 1b). It is well documented that IgG3 antibodies could initiate more effective ADCC and/or CDC effect than IgG1 antibodies. The 3rd GEN L-ICON3 and the 2nd GEN L-ICON1 have similar binding activities to cancer cells and L-ICON3 can actually initiate stronger ADCC cytotoxicity to cancer cells than 2nd GEN ICON (L-ICON1) in vitro. L-ICON3 is also more effective than L-ICON1 in animal models of cancer.

Fourth Generation of TF-Targeting Antibody-Like Immunoconjugates

To combine the benefits of IgG1 antibody (longer serum half-life) and IgG3 antibody (stronger ADCC and/or CDC), hybrid of IgG1 and IgG3 Fc is fused to the C-terminus of Factor VII light chain or Factor VII full length (with or without K341A), as fourth generation ICONs, named L-ICON4 and ICON4, respectively. It was previously shown that ADCC and CDC activities were enhanced in engineered antibodies of IgG1/IgG3 mixed isotype (109).

TF-Targeting Antibodies and Antibody-Drug Conjugates (ADC)

Several humanized monoclonal antibodies (TF-HuMab) and/or antibody-drug conjugates (TF-ADC) are being studied in preclinical and clinical studies (110, 111). A group in the Netherlands generated humanized IgG1 antibodies (tissue factor HuMab) against TF in humanized mice using purified peptide of extracellular domain of TF and TF-expressing NSO cells (110). Three of them, named TF-011, -098 and -111, could induce efficient inhibition of TF SVII-dependent intracellular signaling, ADCC and rapid receptor internalization, but had minimal impact on TF procoagulant activity in vitro. They conjugated those TF HuMab clones with cytotoxic agents MMAE or MMAF and showed that TF-011-MMAE (HuMax-TF-ADC) was the most potent ADC and the dominant mechanism of action in vivo was auristatin-mediated tumor cell killing. TF-011-MMAE induced complete tumor regression in patient-derived xenograft (PDX) models with variable levels of TF expression. Interestingly, the TF-targeting ADC was also effective in the PDX models with TF expression in 25% to 50% of their tumor cells. The reason for the efficacy of the ADC in low TF expressing tumor cell model is that the TF-targeting ADC might also target other TF-positive tumor compartments, such as tumor neovasculature and/or cancer stem cells, which could be individually targeted and eradicated by TF-targeting ICON in vitro (22, 37) and in vitro (24, 28). The results of ADC demonstrated independently that TF-targeting immunotherapy using ADC could have a therapeutic potential to treat multiple types of solid cancers, even with low levels of TF expression on their tumor cells.

The same group further compared the efficacy of TF-targeting ADC with those targeting other cancer cell receptors, such as EGFR and HER2 (112). They conjugated TF, EGFR and HER2-specific antibodies with duostatin-3, a toxin that induces potent cytotoxicity upon antibody-mediated internalization. They showed that TF-ADC was relatively potent in reducing tumor growth compared with EGFR- and HER2-ADCs in xenograft mouse models.

Conclusions

In summary, TF is selectively expressed on angiogenic vascular endothelial cells in the neovasculature of angiogenesis-dependent human diseases, notably solid cancer, AMD, endometriosis and RA. In cancer, TF is also overexpressed by the cancer cells, including solid cancer cells, AML and ALL leukemic cells and sarcoma cell, and cancer stem cells. In addition, TF is potentially by TAM and MDSC (Hu et al. unpublished data) in tumor microenvironment. In RA, TF is additionally expressed locally by macrophages, B cells, fibroblasts and Ki-67 positive synoviocytes in arthritic joints. In macrophage-involved human diseases, TF is abnormally expressed by monocyte-derived macrophages and foam cells in atherosclerosis and by HIV- and Ebola-infected macrophages. These TF-expressing cells (neovascular VECs, cancer cells, CSCs, macrophages/foam cells, fibroblasts, B cells) are all involved in disease progression, whereas normal VECs, monocytes, T and NK cells do not express TF. Thus, targeting TF represents novel therapeutic approaches with the ability to broadly treat these clinical significant diseases.

As discussed above, there are two approaches for making therapeutic antibodies against TF. One approach was to fuse fVII, the natural ligand for TF, to an IgG1 or IgG3 Fc and the other approach was to make human antibodies. fVII-containing antibody-like immunoconjugates (ICON and L-ICONs) have advantages over anti-TF humanized antibodies and antibody-drug conjugates (ADCs), for higher affinity to TF and no need of humanization. The ICON and L-ICON molecules are designed to bind to TF by using its natural ligand fVII, either full length peptide with pro-coagulation active site-mutated (K341A) or light chain peptide with complete depletion of pro-coagulation activity, respectively, with far higher affinity and specificity than can be achieved with an anti-TF antibody. ICON and L-ICON have several important advantages as compared to anti-TF Ab and TF-ADC: (i) The dissociation constant (Kd) for fVII binding to TF is up to $10^{-12}$ M (113), in contrast to anti-TF antibodies that have a Kd in the range of $10^{-8}$ to $10^{-9}$ M for TF (114). (ii) ICON and L-ICON are produced by recombinant DNA technology, allowing these TF-targeting protein agents to be made from human sources for clinical trials without the need of the humanization process that is required for monoclonal antibodies (110). (iii) Due to the fact that ADC is being made by covalently conjugating potent drugs to antibodies, most of ADCs exist as heterogeneous mixtures and require sophisticated site-specific conjugation technologies (115). Moreover, these antibodies against TF in ADCs serve more like a targeting molecule to deliver cytotoxic agents into cancer cells via internalization upon antibody/antigen binding, rather than therapeutic antibodies via ADCC and CDC. The ADC approach is similar to that of fVII-targeted photodynamic therapy (36), in which fVII serves as a targeting molecular to selectively deliver photosensitizers into TF-expressing cancer cells (26, 27, 104, 105), tumor VECs (22, 26, 27, 104, 105) and CSCs (22) via internalization (reaching peak internalization at 30 minutes post fVII binding to TF) (104).

Figure 5A:
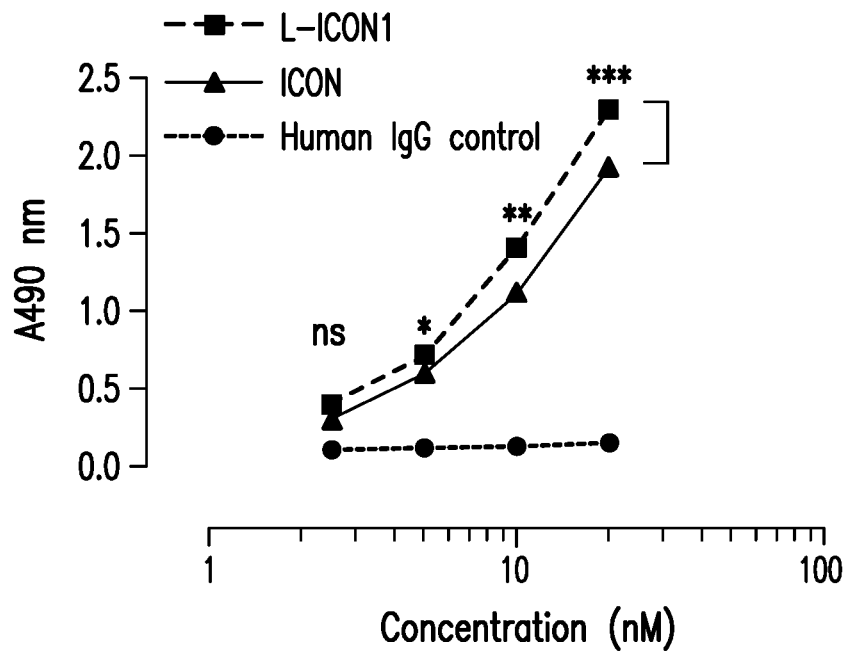
FIG. 5A-B shows that L-ICON1 has stronger binding than ICON to cancer cells (MDA-MB-231) in vitro and is more effective for the treatment of human cancer (MDA-MB-231) in vivo in an orthotopic mouse model in CB-17 SCID mice. Adenoviral vectors encoding ICON, L-ICON1 or without encoding an insert as control (AdBlank) were administered by weekly intratumoral injection (arrows). There were 5 mice in each group in FIG. 5B.
Figure 5B:
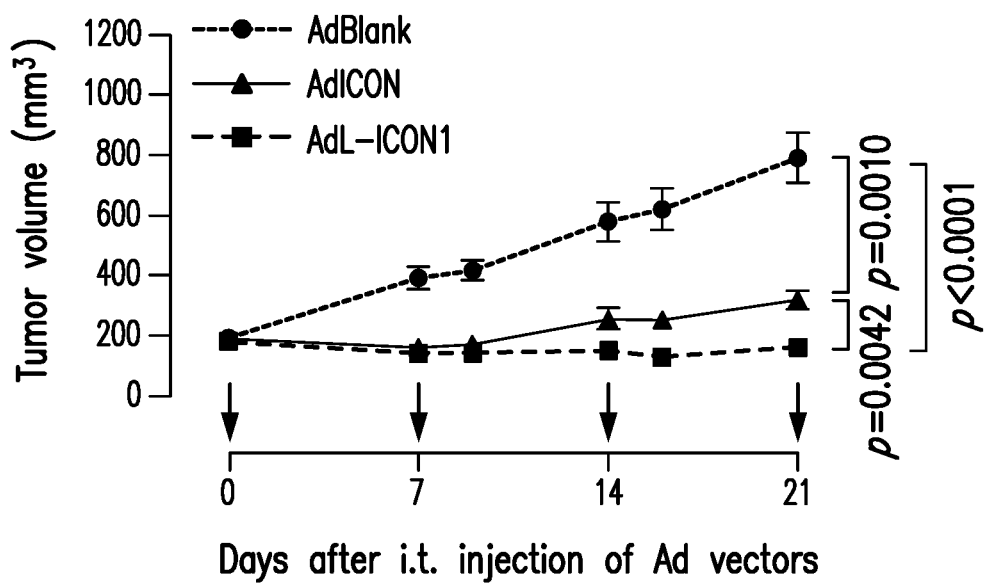
Figure 6A:
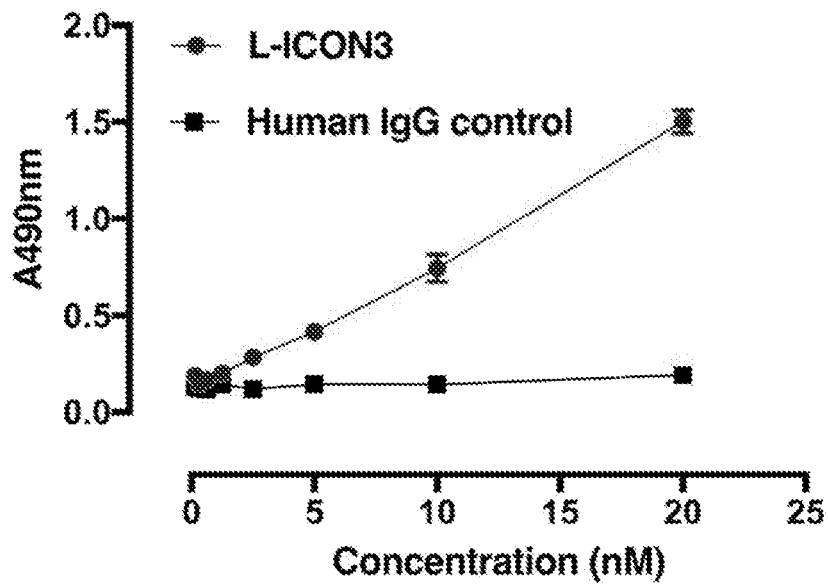
FIG. 6A-6C shows L-ICON3 is more effective than L-ICON1 in vivo in an orthotopic mouse model of murine TNBC.
Figure 6B:
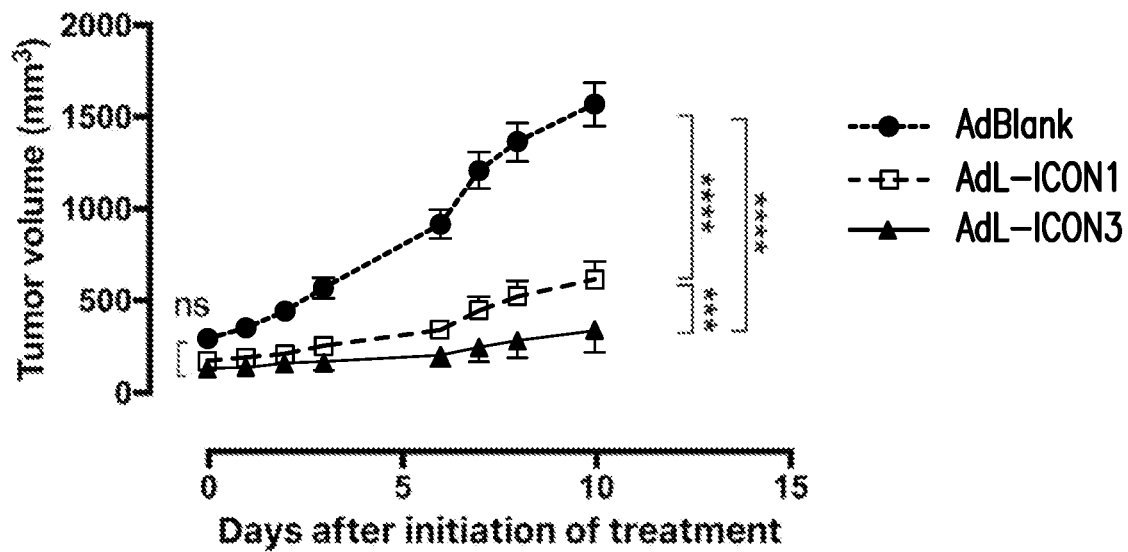
Figure 6C:
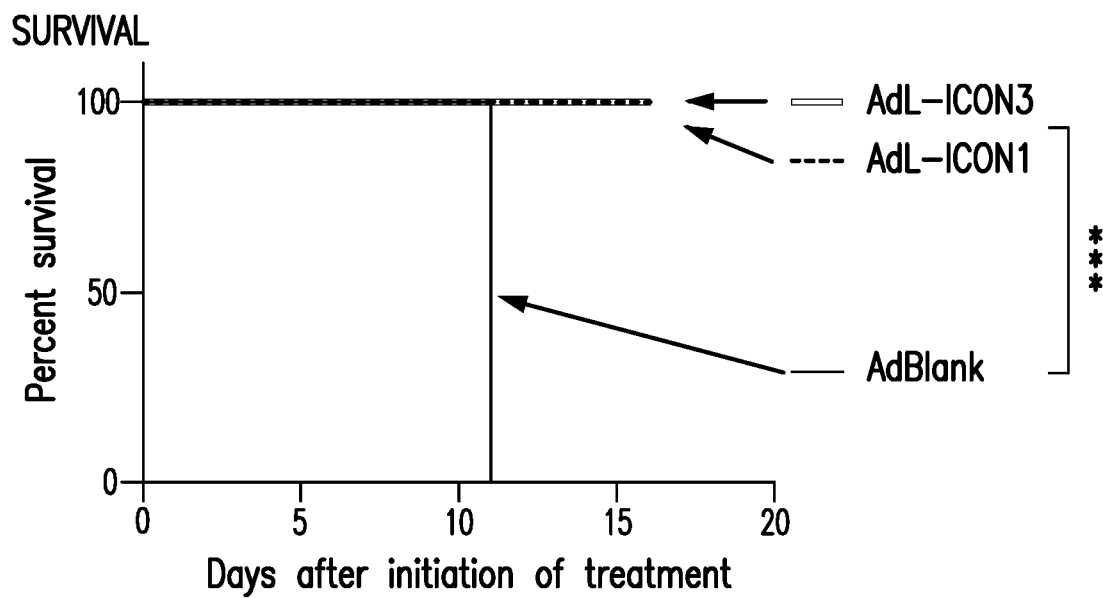

Among three generation TF-targeting ICONs, data shows that the 2nd GEN L-ICON1 is more effective than the 1st GEN ICON (FIG. 5) and that the 3rd GEN L-ICON3 is more effective than the 2nd GEN L-ICON1 in vitro in mediating ADCC to cancer cells (FIG. 4a) and in treating murine breast cancer 4T1 (FIG. 6b), an animal stage IV human breast cancer, in vivo in an orthotopic mouse model. An ideal feature for any TF-targeting antibody-like immunoconjugates or antibodies is that they just bind TF but do not have pro-coagulation activity so that they will not cause disseminated intravascular coagulation disorders in these human diseases. In this regard, L-ICON3 is ideal since it's pro-coagulation activity has been completely depleted.

References for Example 2

1. J. H. Morrissey, H. Fakhrai, T. S. Edgington, Molecular cloning of the cDNA for tissue factor, the cellular receptor for the initiation of the coagulation protease cascade. Cell 50, 129-135 (1987).
2. E. K. Spicer et al., Isolation of cDNA clones coding for human tissue factor: primary structure of the protein and cDNA. Proceedings of the National Academy of Sciences of the United States of America 84, 5148-5152 (1987).
3. W. H. Konigsberg, Y. Nemerson, Molecular cloning of the cDNA for human tissue factor. Cell 52, 639-640 (1988).
4. A. D. Schecter et al., Tissue factor expression in human arterial smooth muscle cells. TF is present in three cellular pools after growth factor stimulation. J Clin Invest 100, 2276-2285 (1997).
5. Y. Nemerson, Tissue factor and the initiation of blood coagulation. Advances in experimental medicine and biology 214, 83-94 (1987).

6. Y. Nemerson, Tissue factor and hemostasis. Blood 71, 1-8 (1988).
7. J. Folkman, Tumor angiogenesis and tissue factor. Nature medicine 2, 167-168 (1996).
8. C. Lopez-Pedrera, N. Barbarroja, G. Dorado, E. Siendones, F. Velasco, Tissue factor as an effector of angiogenesis and tumor progression in hematological malignancies. Leukemia 20, 1331-1340 (2006).
9. J. Rak, C. Milsom, L. May, P. Klement, J. Yu, Tissue factor in cancer and angiogenesis: the molecular link between genetic tumor progression, tumor neovascularization, and cancer coagulopathy. Seminars in thrombosis and hemostasis 32, 54-70 (2006).
10. J. Folkman, Angiogenesis in cancer, vascular, rheumatoid and other disease. Nature medicine 1, 27-31 (1995).
11. J. Folkman, Tumor angiogenesis: therapeutic implications. The New England journal of medicine 285, 1182-1186 (1971).
12. P. S. Bora et al., Immunotherapy for choroidal neovascularization in a laser-induced mouse model simulating exudative (wet) macular degeneration. Proceedings of the National Academy of Sciences of the United States of America 100, 2679-2684 (2003).
13. T. H. Tezel et al., Targeting tissue factor for immunotherapy of choroidal neovascularization by intravitreal delivery of factor VII-Fc chimeric antibody. Ocul Immunol Inflamm 15, 3-10 (2007).
14. G. Krikun et al., The immunoconjugate "icon" targets aberrantly expressed endothelial tissue factor causing regression of endometriosis. Am J Pathol 176, 1050-1056 (2010).
15. D. Hanahan, R. A. Weinberg, The hallmarks of cancer. Cell 100, 57-70 (2000).
16. D. Hanahan, R. A. Weinberg, Hallmarks of cancer: the next generation. Cell 144, 646-674 (2011).
17. N. Ferrara, VEGF and the quest for tumour angiogenesis factors. Nature reviews. Cancer 2, 795-803 (2002).
18. M. Klagsbrun, R. Sullivan, S. Smith, R. Rybka, Y. E. Shing, Purification of endothelial cell growth factors by heparin affinity chromatography. Methods in enzymology 147, 95-105 (1987).
19. A. O. Afuwape, S. Kiriakidis, E. M. Paleolog, The role of the angiogenic molecule VEGF in the pathogenesis of rheumatoid arthritis. Histology and histopathology 17, 961-972 (2002).
20. J. Fujimoto, H. Sakaguchi, R. Hirose, H. Wen, T. Tamaya, Angiogenesis in endometriosis and angiogenic factors. Gynecologic and obstetric investigation 48 Suppl 1, 14-20 (1999).
21. Z. Hu et al., Assessing the carcinogenic potential of low-dose exposures to chemical mixtures in the environment: focus on the cancer hallmark of tumor angiogenesis. Carcinogenesis 36 Suppl 1, S184-202 (2015).
22. Z. Hu, J. Cheng, J. Xu, W. Ruf, C. J. Lockwood, Tissue factor is an angiogenic-specific receptor for factor VII-targeted immunotherapy and photodynamic therapy. Angiogenesis 20, 85-96 (2017).
23. J. Contrino, G. Hair, D. L. Kreutzer, F. R. Rickles, In situ detection of tissue factor in vascular endothelial cells: correlation with the malignant phenotype of human breast disease. Nature medicine 2, 209-215 (1996).
24. Z. Hu, Y. Sun, A. Garen, Targeting tumor vasculature endothelial cells and tumor cells for immunotherapy of human melanoma in a mouse xenograft model. Proceedings of the National Academy of Sciences of the United States of America 96, 8161-8166 (1999).
25. Z. Hu, A. Garen, Targeting tissue factor on tumor vascular endothelial cells and tumor cells for immunotherapy in mouse models of prostatic cancer. Proceedings of the National Academy of Sciences of the United States of America 98, 12180-12185 (2001).
26. J. Cheng et al., Effective treatment of human lung cancer by targeting tissue factor with a factor VII-targeted photodynamic therapy. Current cancer drug targets 11, 1069-1081 (2011).
27. J. Duanmu, J. Cheng, J. Xu, C. J. Booth, Z. Hu, Effective treatment of chemoresistant breast cancer in vitro and in vivo by a factor VII-targeted photodynamic therapy. British journal of cancer 104, 1401-1409 (2011).
28. Z. Hu, A. Garen, Intratumoral injection of adenoviral vectors encoding tumor-targeted immunoconjugates for cancer immunotherapy. Proceedings of the National Academy of Sciences of the United States of America 97, 9221-9225 (2000).
29. H. E. Grossniklaus et al., Macrophage and retinal pigment epithelium expression of angiogenic cytokines in choroidal neovascularization. Mol Vis 8, 119-126 (2002).
30. G. Krikun, F. Schatz, H. Taylor, C. J. Lockwood, Endometriosis and tissue factor. Ann NY Acad Sci 1127, 101-105 (2008).
31. C. J. Lockwood et al., The role of tissue factor in regulating endometrial haemostasis: implications for progestin-only contraception. Hum Reprod 15 Suppl 3, 144-151 (2000).
32. F. Schatz, G. Krikun, R. Caze, M. Rahman, C. J. Lockwood, Progestin-regulated expression of tissue factor in decidual cells: implications in endometrial hemostasis, menstruation and angiogenesis. Steroids 68, 849-860 (2003).
33. G. Krikun, Endometriosis, angiogenesis and tissue factor. Scientifica (Cairo) 2012, 306830 (2012).
34. J. Contrino, G. A. Hair, M. A. Schmeizl, F. R. Rickles, D. L. Kreutzer, In situ characterization of antigenic and functional tissue factor expression in human tumors utilizing monoclonal antibodies and recombinant factor VIIa as probes. Am J Pathol 145, 1315-1322 (1994).
35. N. S. Callander, N. Varki, L. V. Rao, Immunohistochemical identification of tissue factor in solid tumors. Cancer 70, 1194-1201 (1992).
36. Z. Hu, Factor VII-Targeted Photodynamic Therapy for Breast Cancer and Its Therapeutic Potential for Other Solid Cancers and Leukemia, Breast Cancer—Current and Alternative Therapeutic Modalities, Esra Gunduz and Mehmet Gunduz (Ed.), ISBN: 978-953-307-776-5, InTech, Available from: http://www.intechopen.com/articles/show/title/factor-vii-targeted-photodynamic-therapy-for-breast-cancer-and-its-therapeutic-potential-for-other-s. E. Gunduz, Gunduz, M., Ed., Breast Cancer—Current and Alternative Therapeutic Modalities (InTech, 2011), pp. 175-196.
37. Z. Hu et al., Targeting tissue factor as a novel therapeutic oncotarget for eradication of cancer stem cells isolated from tumor cell lines, tumor xenografts and patients of breast, lung and ovarian cancer. Oncotarget 8, 1481-1494 (2017).
38. H. Tanaka et al., Studies on leukemic cell tissue factor. Thromb Res 53, 535-549 (1989).
39. T. Kubota, K. Andoh, H. Sadakata, H. Tanaka, N. Kobayashi, Tissue factor released from leukemic cells. Thromb Haemost 65, 59-63 (1991).
40. J. C. Freeburn, W. S. Gilmore, J. J. Strain, The effect of cytokines on tissue factor expression in HL-60 and U937 cell lines. Biochem Soc Trans 23, 286S (1995).

41. F. R. Rickles, G. A. Hair, R. A. Zeff, E. Lee, R. D. Bona, Tissue factor expression in human leukocytes and tumor cells. Thromb Haemost 74, 391-395 (1995).
42. G. A. Hair et al., Tissue factor expression in human leukemic cells. Leuk Res 20, 1-11 (1996).
43. M. Tanaka, Induction of tissue factor-like activity of human monoblastic leukemia cell line by tumor necrosis factor-alpha. Thromb Res 56, 201-211 (1989).
44. K. Andoh et al., Tissue factor activity in leukemia cells. Special reference to disseminated intravascular coagulation. Cancer 59, 748-754 (1987).
45. K. A. Bauer et al., Tissue factor gene expression in acute myeloblastic leukemia. Thromb Res 56, 425-430 (1989).
46. M. Tanaka, T. Kishi, Induction of tissue factor by interleukin-2 in acute myelogenous leukemia (AML) cells. Growth Factors 4, 1-8 (1990).
47. M. Tanaka, H. Yamanishi, The expression of tissue factor antigen and activity on the surface of leukemic cells. Leuk Res 17, 103-111 (1993).
48. T. Nakasaki et al., Elevated tissue factor levels in leukemic cell homogenate. Clin Appl Thromb Hemost 6, 14-17 (2000).
49. T. Nakasaki et al., Decreased tissue factor and tissue-plasminogen activator antigen in relapsed acute promyelocytic leukemia. Am J Hematol 64, 145-150 (2000).
50. Y. Zhang et al., Intravenous somatic gene transfer with antisense tissue factor restores blood flow by reducing tumor necrosis factor-induced tissue factor expression and fibrin deposition in mouse meth-A sarcoma. J Clin Invest 97, 2213-2224 (1996).
51. J. G. Bledsoe, S. M. Slack, Tissue factor expression by rat osteosarcoma cells adherent to tissue culture polystyrene and selected orthopedic biomaterials. J Biomater Sci Polym Ed 9, 1305-1312 (1998).
52. Y. M. Zhang et al., Vascular origin of Kaposi's sarcoma. Expression of leukocyte adhesion molecule-1, thrombomodulin, and tissue factor. Am J Pathol 144, 51-59 (1994).
53. T. M. Phillips, W. H. McBride, F. Pajonk, The response of CD24(-/low)/CD44+ breast cancer-initiating cells to radiation. Journal of the National Cancer Institute 98, 1777-1785 (2006).
54. G. Ferrandina, M. Petrillo, G. Bonanno, G. Scambia, Targeting CD133 antigen in cancer. Expert Opin Ther Targets 13, 823-837 (2009).
55. C. Sheridan et al., CD44+/CD24− breast cancer cells exhibit enhanced invasive properties: an early step necessary for metastasis. Breast Cancer Res 8, R59 (2006).
56. V. Adorno-Cruz et al., Cancer stem cells: targeting the roots of cancer, seeds of metastasis, and sources of therapy resistance. Cancer research 75, 924-929 (2015).
57. Z. Hu, J. Li, Natural killer cells are crucial for the efficacy of Icon (factor VII/human IgG1 Fc) immunotherapy in human tongue cancer. BMC immunology 11, 49 (2010).
58. R. O. Williams, M. Feldmann, R. N. Maini, Anti-tumor necrosis factor ameliorates joint disease in murine collagen-induced arthritis. Proceedings of the National Academy of Sciences of the United States of America 89, 9784-9788 (1992).
59. N. Busso, C. Morard, R. Salvi, V. Peclat, A. So, Role of the tissue factor pathway in synovial inflammation. Arthritis Rheum 48, 651-659 (2003).
60. L. Chen et al., Tissue factor expression in rheumatoid synovium: a potential role in pannus invasion of rheumatoid arthritis. Acta histochemica, (2013).
61. Z. Szekanecz, A. E. Koch, Angiogenesis and its targeting in rheumatoid arthritis. Vascul Pharmacol 51, 1-7 (2009).
62. P. R. Colville-Nash, D. L. Scott, Angiogenesis and rheumatoid arthritis: pathogenic and therapeutic implications. Ann Rheum Dis 51, 919-925 (1992).
63. E. M. Paleolog, R. A. Fava, Angiogenesis in rheumatoid arthritis: implications for future therapeutic strategies. Springer Semin Immunopathol 20, 73-94 (1998).
64. Z. Szekanecz, G. Szegedi, A. E. Koch, Angiogenesis in rheumatoid arthritis: pathogenic and clinical significance. J Investig Med 46, 27-41 (1998).
65. D. G. Stupack, C. M. Storgard, D. A. Cheresh, A role for angiogenesis in rheumatoid arthritis. Braz J Med Biol Res 32, 573-581 (1999).
66. E. M. Paleolog, Angiogenesis in rheumatoid arthritis. Arthritis Res 4 Suppl 3, S81-90 (2002).
67. Z. Szekanecz, L. Gaspar, A. E. Koch, Angiogenesis in rheumatoid arthritis. Front Biosci 10, 1739-1753 (2005).
68. N. Maruotti, F. P. Cantatore, E. Crivellato, A. Vacca, D. Ribatti, Angiogenesis in rheumatoid arthritis. Histology and histopathology 21, 557-566 (2006).
69. Z. Szekanecz, T. Besenyei, G. Paragh, A. E. Koch, Angiogenesis in rheumatoid arthritis. Autoimmunity 42, 563-573 (2009).
70. A. Marrelli et al., Angiogenesis in rheumatoid arthritis: A disease specific process or a common response to chronic inflammation? Autoimmun Rev, (2011).
71. Z. Szekanecz, A. E. Koch, Endothelial cells in inflammation and angiogenesis. Current drug targets. Inflammation and allergy 4, 319-323 (2005).
72. H. Wada, Y. Wakita, H. Shiku, Tissue factor expression in endothelial cells in health and disease. Blood coagulation & fibrinolysis: an international journal in haemostasis and thrombosis 6 Suppl 1, S26-31 (1995).
73. B. Osterud, E. Bjorklid, The production and availability of tissue thromboplastin in cellular populations of whole blood exposed to various concentrations of endotoxin. An assay for detection of endotoxin. Scand J Haematol 29, 175-184 (1982).
74. J. C. Lewis et al., Tissue factor expression during coculture of endothelial cells and monocytes. Experimental and molecular pathology 62, 207-218 (1995).
75. T. Luther, C. Flossel, V. Hietschhold, R. Koslowski, M. Muller, Flow cytometric analysis of tissue factor (TF) expression on stimulated monocytes—comparison to procoagulant activity of mononuclear blood cells. Blut 61, 375-378 (1990).
76. J. M. Herbert, P. Savi, M. C. Laplace, A. Lale, IL-4 inhibits LPS-, IL-1 beta- and TNF alpha-induced expression of tissue factor in endothelial cells and monocytes. FEBS letters 310, 31-33 (1992).
77. J. M. Herbert et al., Malformin-A1 inhibits the binding of interleukin-1 beta (IL1 beta) and suppresses the expression of tissue factor in human endothelial cells and monocytes. Biochemical pharmacology 48, 1211-1217 (1994).
78. E. Camerer, A. B. Kolsto, H. Prydz, Cell biology of tissue factor, the principal initiator of blood coagulation. Thromb Res 81, 1-41 (1996).
79. U. R. Pendurthi, D. Alok, L. V. Rao, Binding of factor VIIa to tissue factor induces alterations in gene expression in human fibroblast cells: up-regulation of poly(A) polymerase. Proceedings of the National Academy of Sciences of the United States of America 94, 12598-12603 (1997).

80. E. F. Grabowski, D. B. Zuckerman, Y. Nemerson, The functional expression of tissue factor by fibroblasts and endothelial cells under flow conditions. Blood 81, 3265-3270 (1993).
81. M. Juarez, A. Filer, C. D. Buckley, Fibroblasts as therapeutic targets in rheumatoid arthritis and cancer. Swiss medical weekly 142, w13529 (2012).
82. T. Dorner, G. R. Burmester, The role of B cells in rheumatoid arthritis: mechanisms and therapeutic targets. Current opinion in rheumatology 15, 246-252 (2003).
83. T. Dorner, P. E. Lipsky, B-cell targeting: a novel approach to immune intervention today and tomorrow. Expert opinion on biological therapy 7, 1287-1299 (2007).
84. T. Dorner et al., Current status on B-cell depletion therapy in autoimmune diseases other than rheumatoid arthritis. Autoimmun Rev 9, 82-89 (2009).
85. T. Dorner, N. Kinnman, P. P. Tak, Targeting B cells in immune-mediated inflammatory disease: a comprehensive review of mechanisms of action and identification of biomarkers. Pharmacology & therapeutics 125, 464-475 (2010).
86. H. Mechiche, P. Cornillet-Lefebvre, P. Nguyen, A subpopulation of human B lymphocytes can express a functional Tissue Factor in response to phorbol myristate acetate. Thromb Haemost 94, 146-154 (2005).
87. H. Mechiche, P. Nguyen, IL-4 modulates tissue factor expression by human B lymphocytes in response to phorbol myristate acetate. Thromb Haemost 97, 158-159 (2007).
88. R. Badolato, J. J. Oppenheim, Role of cytokines, acute-phase proteins, and chemokines in the progression of rheumatoid arthritis. Semin Arthritis Rheum 26, 526-538 (1996).
89. Z. Szekanecz, A. Pakozdi, A. Szentpetery, T. Besenyei, A. E. Koch, Chemokines and angiogenesis in rheumatoid arthritis. Front Biosci (Elite Ed) 1, 44-51 (2009).
90. K. D. Deane et al., The number of elevated cytokines and chemokines in preclinical seropositive rheumatoid arthritis predicts time to diagnosis in an age-dependent manner. Arthritis Rheum 62, 3161-3172 (2010).
91. H. Kokkonen et al., Up-regulation of cytokines and chemokines predates the onset of rheumatoid arthritis. Arthritis Rheum 62, 383-391 (2010).
92. J. Friedl et al., Induction of permeability across endothelial cell monolayers by tumor necrosis factor (TNF) occurs via a tissue factor-dependent mechanism: relationship between the procoagulant and permeability effects of TNF. Blood 100, 1334-1339 (2002).
93. M. Mayr et al., Proteomics, metabolomics, and immunomics on microparticles derived from human atherosclerotic plaques. Circ Cardiovasc Genet 2, 379-388 (2009).
94. M. Camera et al., The Role of Tissue Factor in Atherothrombosis and Coronary Artery Disease: Insights into Platelet Tissue Factor. Seminars in thrombosis and hemostasis 41, 737-746 (2015).
95. K. Tatsumi, N. Mackman, Tissue Factor and Atherothrombosis. J Atheroscler Thromb 22, 543-549 (2015).
96. D. Saha, S. S, E. G. Sergeeva, Z. I. Ionova, A. V. Gorbach, Tissue factor and atherothrombosis. Curr Pharm Des 21, 1152-1157 (2015).
97. A. P. Owens, 3rd, N. Mackman, Role of tissue factor in atherothrombosis. Curr Atheroscler Rep 14, 394-401 (2012).
98. P. Meerarani, P. R. Moreno, G. Cimmino, J. J. Badimon, Atherothrombosis: role of tissue factor; link between diabetes, obesity and inflammation. Indian J Exp Biol 45, 103-110 (2007).
99. J. F. Viles-Gonzalez, J. J. Badimon, Atherothrombosis: the role of tissue factor. Int J Biochem Cell Biol 36, 25-30 (2004).
100. P. Benaroch, E. Billard, R. Gaudin, M. Schindler, M. Jouve, HIV-1 assembly in macrophages. Retrovirology 7, 29 (2010).
101. Z. F. Rosenberg, A. S. Fauci, Immunopathogenesis of HIV infection. FASEB J 5, 2382-2390 (1991).
102. N. T. Funderburg et al., Increased tissue factor expression on circulating monocytes in chronic HIV infection: relationship to in vivo coagulation and immune activation. Blood 115, 161-167 (2010).
103. Y. Tang et al., Mapping of angiogenic markers for targeting of vectors to tumor vascular endothelial cells. Cancer Gene Ther 14, 346-353 (2007).
104. Z. Hu, B. Rao, S. Chen, J. Duanmu, Selective and effective killing of angiogenic vascular endothelial cells and cancer cells by targeting tissue factor using a factor VII-targeted photodynamic therapy for breast cancer. Breast Cancer Res Treat, (2010).
105. Z. Hu, B. Rao, S. Chen, J. Duanmu, Targeting tissue factor on tumour cells and angiogenic vascular endothelial cells by factor VII-targeted verteporfin photodynamic therapy for breast cancer in vitro and in vivo in mice. BMC Cancer 10, 235 (2010).
106. J. M. Brenchley et al., Microbial translocation is a cause of systemic immune activation in chronic HIV infection. Nature medicine 12, 1365-1371 (2006).
107. T. W. Geisbert et al., Mechanisms underlying coagulation abnormalities in ebola hemorrhagic fever: overexpression of tissue factor in primate monocytes/macrophages is a key event. J Infect Dis 188, 1618-1629 (2003).
108. T. W. Geisbert et al., Treatment of Ebola virus infection with a recombinant inhibitor of factor VIIa/tissue factor: a study in rhesus monkeys. Lancet 362, 1953-1958 (2003).
109. A. Natsume et al., Engineered antibodies of IgG1/IgG3 mixed isotype with enhanced cytotoxic activities. Cancer research 68, 3863-3872 (2008).
110. E. C. Breij et al., An antibody-drug conjugate that targets tissue factor exhibits potent therapeutic activity against a broad range of solid tumors. Cancer research 74, 1214-1226 (2014).
111. X. Zhang et al., Pathological expression of tissue factor confers promising antitumor response to a novel therapeutic antibody SC1 in triple negative breast cancer and pancreatic adenocarcinoma. Oncotarget 8, 59086-59102 (2017).
112. B. E. de Goeij et al., High turnover of tissue factor enables efficient intracellular delivery of antibody-drug conjugates. Mol Cancer Ther 14, 1130-1140 (2015).
113. E. Waxman et al., Tissue factor and its extracellular soluble domain: the relationship between intermolecular association with factor VIIa and enzymatic activity of the complex. Biochemistry 31, 3998-4003 (1992).
114. L. Presta et al., Generation of a humanized, high affinity anti-tissue factor antibody for use as a novel antithrombotic therapeutic. Thromb Haemost 85, 379-389 (2001).
115. V. Chudasama, A. Maruani, S. Caddick, Recent advances in the construction of antibody-drug conjugates. Nat Chem 8, 114-119 (2016).
116. Zhiwei Hu*, Rulong Shen, Amanda Campbell, Elizabeth McMichael, Lianbo Yu, Bhuvaneswari Ramaswamy, Cheryl A. London, Tian Xu and William E. Carson III. Targeting Tissue Factor for Immunotherapy of Triple-Negative Breast Cancer using a Second-Generation ICON. Cancer Immunology Research. Accepted Mar. 7, 2018.

117. Hu et al. Therapeutic antibody-like immunoconjugates against tissue factor with the potential to treat angiogenesis-dependent as well as macrophage-associated human diseases. Antibodies. 2018, 7(1), 8; doi:10.3390/antib7010008.

Example 3: Fourth Generation ICONs

1. L-ICON4: Combination of L-ICON1 and L-ICON3

As discussed above, there are three L-ICON1 proteins, named L-ICON1 (SEQ ID NO: 14), L-ICON1(WT) (SEQ ID NO: 16) and L-ICON1 (E333A) (SEQ ID NO: 18). Their cDNA sequences have been deposited to GenBank with accession numbers KX760097, KX760098 and KX760099, respectively.

There are also two L-ICON3 proteins, named L-ICON3 (WT) (SEQ ID NO: 2) or L-ICON3, (GenBank accession no. KY223609) and L-ICON3 (R435H) (SEQ ID NO: 6).

L-ICON4 can be derived from combination of each of three L-ICON1 proteins with each of two L-ICON3 proteins. These are listed in Table 2.

2. ICON4: Combination of ICON1 and ICON3

There are also two ICON1 proteins, named ICON1 (WT) (SEQ ID NO: 10) and ICON1 (E333A) (SEQ ID NO: 12). The IgG1 Fc sequence in these new ICON1 proteins is different from the original ICON sequence (human ICON GenBank AF272774). The major difference in these new ICON1 is that they have a 6-amino acid residue shorter hinge region as compared to the original ICON (or called ICON1, AF272774).

There are two ICON3 proteins, named ICON3(WT) (GenBank accession no. KY223610) (SEQ ID NO: 4) and ICON3(R435H) (SEQ ID NO: 8).

Therefore, ICON4 can be derived from combination of each of two L-ICON1 with each of two ICON3 (Table 3).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

SEQUENCES

```
SEQ ID NO: 1: Human factor VII light chain-human IgG3 Fc (L-ICON3) mRNA,
complete coding sequence (GenBank accession no. KY223609).
       1  aagcttgaat tcgccaccat ggtctcccag gccctcaggc tcctctgcct tctgcttggg
      61  cttcagggct gcctggctgc agtcttcgta acccaggagg aagcccacgg cgtcctgcac
     121  cggcgccggc gcgccaacgc gttcctggag gagctgcggc cgggctccct ggagagggag
     181  tgcaaggagg agcagtgctc cttcgaggag gcccgggaga tcttcaagga cgcggagagg
     241  acgaagctgt tctggatttc ttacagtgat ggtgaccagt gtgcctcaag tccatgccag
     301  aatgggggct cctgcaagga ccagctccag tcctatatct gcttctgcct ccctgccttc
     361  gagggccgga actgtgagac gcacaaggat gaccagctga tctgtgtgaa cgagaacggc
     421  ggctgtgagc agtactgcag tgaccacacg ggcaccaagc gctcctgtcg gtgccacgag
     481  gggtactctc tgctggcaga cggggtgtcc tgcacaccca cagttgaata tccatgtgga
     541  aaaatcccta ttctagaaaa aagaaatgcc agcaagcccc aagggcgagg atccgacaca
     601  cctccccgt gcccaaggtg cccagcacct gaactcctgg gaggaccgtc agtcttcctc
     661  ttccccccaa acccaagga tacccttatg atttcccgga ccctgaggt cacgtgcgtg
     721  gtggtggacg tgagccacga agaccccgag gtccagttca gtggtacgt ggacggcgtg
     781  gaggtgcata atgccaagac aaagccgcgg gaggagcagt acaacagcac gttccgtgtg
     841  gtcagcgtcc tcaccgtcct gcaccaggac tggctgaacg gcaaggagta caagtgcaag
     901  gtctccaaca aagccctccc agcccccatc gagaaaacca tctccaaaac caaaggacag
     961  ccccgagaac cacaggtgta cacctgccc ccatcccggg aggagatgac caagaaccag
    1021  gtcagcctga cctgcctggt caaaggcttc tacccagcg acatcgccgt ggagtgggag
    1081  agcagcgggc agccggagaa caactacaac accacgcctc ccatgctgga ctccgacggc
    1141  tccttcttcc tctacagcaa gctcaccgtg gacaagagca ggtggcagca ggggaacatc
    1201  ttctcatgct ccgtgatgca tgaggctctg cacaaccgct tcacgcagaa gagcctctcc
    1261  ctgtctccgg gtaaatgagc ggccgc
```

-continued (HindIII-EcoRI-Kozak-ATG-hfVIIL-BamtlI-hIgG3Fc-Stop-NotI)

SEQ ID NO: 2: Monomer of L-ICON3 peptide

MVSQALRLLCLLLGLQGCLAAVFVTQEEAHGVLHRRRRANAFLEELRPGSLERECKEEQCSFEEAREIFK

DAERTKLFWISYSDGDQCASSPCQNGGSCKDQLQSYICFCLPAFEGRNCETHKDDQLICVNENGGCEQYC

SDHTGTKRSCRCHEGYSLLADGVSCTPTVEYPCGKIPILEKRNASKPQGRGSDTPPPCPRCPAPELLGGP

SVFLFPPKPKDTLMISRTPEVTCVVVDVSHEDPEVQFKWYVDGVEVHNAKTKPREEQYNSTFRVVSVLTV

LHQDWLNGKEYKCKVSNKALPAPIEKTISKTKGQPREPQVYTLPPSREEMTKNQVSLTCLVKGFYPSDIA

VEWESSGQPENNYNTTPPMLDSDGSFFLYSKLTVDKSRWQQGNIFSCSVMHEALHNRFTQKSLSLSPGK

SEQ ID NO: 3: Human factor VII (K341A)-human IgG3 Fc (ICON3) mRNA,
complete coding sequence (GenBank accession no. KY223610).

```
   1 aagctttgca gagatttcat catggtctcc caggccctca ggctcctctg ccttctgctt
  61 gggcttcagg gctgcctggc tgcagtcttc gtaacccagg aggaagccca cggcgtcctg
 121 caccggcgcc ggcgcgccaa cgcgttcctg gaggagctgc ggccgggctc cctggagagg
 181 gagtgcaagg aggagcagtg ctccttcgag gagcccggg agatcttcaa ggacgcggag
 241 aggacgaagc tgttctggat ttcttacagt gatggtgacc agtgtgcctc aagtccatgc
 301 cagaatgggg gctcctgcaa ggaccagctc cagtcctata tctgcttctg cctccctgcc
 361 ttcgagggcc ggaactgtga gacgcacaag gatgaccagc tgatctgtgt gaacgagaac
 421 ggcggctgtg agcagtactg cagtgaccac acgggcacca gcgctcctg tcggtgccac
 481 gagggtact ctctgctggc agacggggtg tcctgcacac ccacagttga atatccatgt
 541 ggaaaaatac ctattctaga aaaaagaaat gccagcaagc ccaaggggcg aattgtgggg
 601 ggcaaggtgt gccccaaagg ggagtgtcca tggcaggtcc tgttgttggt gaatggagct
 661 cagttgtgtg gggggaccct gatcaacacc atctgggtgg tctccgcggc ccactgtttc
 721 gacaaaatca gaactggag gaacctgatc gcggtgctcg gggagcacga cctcagcgag
 781 cacgacgggg atgagcagag ccggcgggtg gcgcaggtca tcatcccag cacgtacgtc
 841 ccgggcacca ccaaccacga catcgcgctg ctccgcctgc accagcccgt ggtcctcact
 901 gaccatgtgg tgcccctctg cctgccgaa cggacgttct ctgagaggac gctggccttc
 961 gtgcgcttct cattggtcag cggctggggc cagctgctgg accgtggcgc acggcccctg
1021 gagctcatgg tcctcaacgt gccccggctg atgacccagg actgcctgca gcagtcacgg
1081 aaggtgggag actccccaaa tatcacggag tacatgttct gtgccggcta ctcggatggc
1141 agcaaggact cctgcgcggg ggacagtgga ggcccacatg ccacccacta ccggggcacg
1201 tggtacctga cgggcatcgt cagctggggc cagggctgcg caaccgtggg ccactttggg
1261 gtgtacacca gggtctccca gtacatcgag tggctgcaaa agctcatgcg ctcagagcca
1321 cgcccaggag tcctcctgcg agccccattt cccggatccg acacacctcc ccgtgccca
1381 aggtgcccag cacctgaact cctgggagga ccgtcagtct tcctcttccc cccaaaaccc
1441 aaggatacc ttatgatttc ccggacccct gaggtcacgt gcgtggtggt ggacgtgagc
1501 cacgaagacc ccgaggtcca gttcaagtgg tacgtggacg gcgtggaggt gcataatgcc
1561 aagacaaagc cgcgggagga gcagtacaac agcacgttcc gtgtggtcag cgtcctcacc
1621 gtcctgcacc aggactggct gaacggcaag gagtacaagt gcaaggtctc caacaaagcc
1681 ctcccagccc ccatcgagaa aaccatctcc aaaaccaaag acagccccg agaaccacag
1741 gtgtacaccc tgcccccatc ccgggaggag atgaccaaga accaggtcag cctgacctgc
1801 ctggtcaaag gcttctaccc cagcgacatc gccgtggagt gggagagcag cgggcagccg
1861 gagaacaact acaacaccac gcctcccatg ctggactccg acggctcctt cttcctctac
```

-continued

```
1921 agcaagctca ccgtggacaa gagcaggtgg cagcagggga acatcttctc atgctccgtg 1981 atgcatgagg ctctgcacaa ccgcttcacg cagaagagcc tctccctgtc tccgggtaaa 2041 tgagcggccg c
```

SEQ ID NO: 4: Monomer of ICON3 peptide
MVSQALRLLCLLLGLQGCLAAVFVTQEEAHGVLHRRRRANAFLEELRPGSLERECKEEQCSFEEAREIFK

DAERTKLFWISYSDGDQCASSPCQNGGSCKDQLQSYICFCLPAFEGRNCETHKDDQLICVNENGGCEQYC

SDHTGTKRSCRCHEGYSLLADGVSCTPTVEYPCGKIPILEKRNASKPQGRIVGGKVCPKGECPWQVLLLV

NGAQLCGGTLINTIWVVSAAHCFDKIKNWRNLIAVLGEHDLSEHDGDEQSRRVAQVIIPSTYVPGTTNHD

IALLRLHQPVVLTDHVVPLCLPERTFSERTLAFVRFSLVSGWGQLLDRGATALELMVLNVPRLMTQDCLQ

QSRKVGDSPNITEYMFCAGYSDGSKDSCAGDSGGPHATHYRGTWYLTGIVSWGQGCATVGHFGVYTRVSQ

YIEWLQKLMRSEPRPGVLLRAPFPGSDTPPPCPRCPAPELLGGPSVFLFPPKPKDTLMISRTPEVTCVVV

DVSHEDPEVQFKWYVDGVEVHNAKTKPREEQYNSTFRVVSVLTVLHQDWLNGKEYKCKVSNKALPAPIEK

TISKTKGQPREPQVYTLPPSREEMTKNQVSLTCLVKGFYPSDIAVEWESSGQPENNYNTTPPMLDSDGSF

FLYSKLTVDKSRWQQGNIFSCSVMHEALHNRFTQKSLSLSPGK

SEQ ID NO: 5: L-ICON3 (R435H)
AAGCTTGAATTCGCCACCATGGTCTCCCAGGCCCTCAGGCTCCTCTGCCTTCTGCTTG

GGCTTCAGGGCTGCCTGGCTGCAGTCTTCGTAACCCAGGAGGAAGCCCACGGCGTC

CTGCACCGGCGCCGGCGCGCCAACGCGTTCCTGGAGGAGCTGCGGCCGGGCTCCCT

GGAGAGGGAGTGCAAGGAGGAGCAGTGCTCCTTCGAGGAGGCCCGGGAGATCTTCA

AGGACGCGGAGAGGACGAAGCTGTTCTGGATTTCTTACAGTGATGGTGACCAGTGT

GCCTCAAGTCCATGCCAGAATGGGGGCTCCTGCAAGGACCAGCTCCAGTCCTATATC

TGCTTCTGCCTCCCTGCCTTCGAGGGCCGGAACTGTGAGACGCACAAGGATGACCAG

CTGATCTGTGTGAACGAGAACGGCGGCTGTGAGCAGTACTGCAGTGACCACACGGG

CACCAAGCGCTCCTGTCGGTGCCACGAGGGGTACTCTCTGCTGGCAGACGGGGTGTC

CTGCACACCCACAGTTGAATATCCATGTGGAAAAATACCTATTCTAGAAAAAAGAA

ATGCCAGCAAGCCCCAAGGGCGAGGATCCGACACACCTCCCCCGTGCCCAAGGTGC

CCAGCACCTGAACTCCTGGGAGGACCGTCAGTCTTCCTCTTCCCCCCAAAACCCAAG

GATACCCTTATGATTTCCCGGACCCCTGAGGTCACGTGCGTGGTGGTGGACGTGAGC

CACGAAGACCCCGAGGTCCAGTTCAAGTGGTACGTGGACGGCGTGGAGGTGCATAA

TGCCAAGACAAAGCCGCGGGAGGAGCAGTACAACAGCACGTTCCGTGTGGTCAGCG

TCCTCACCGTCCTGCACCAGGACTGGCTGAACGGCAAGGAGTACAAGTGCAAGGTC

TCCAACAAAGCCCTCCCAGCCCCCATCGAGAAAACCATCTCCAAAACCAAAGGACA

GCCCCGAGAACCACAGGTGTACACCCTGCCCCCATCCCGGGAGGAGATGACCAAGA

ACCAGGTCAGCCTGACCTGCCTGGTCAAAGGCTTCTACCCCAGCGACATCGCCGTGG

AGTGGGAGAGCAGCGGGCAGCCGGAGAACAACTACAACACCACGCCTCCCATGCTG

GACTCCGACGGCTCCTTCTTCCTCTACAGCAAGCTCACCGTGGACAAGAGCAGGTGG

CAGCAGGGGAACATCTTCTCATGCTCCGTGATGCATGAGGCTCTGCACAACCACTTC

ACACAGAAGAGCCTCTCCCTGTCTCCGGGTAAATGAGCGGCCGC

SEQ ID NO: 6 MONOMER OF L-ICON3 (R435H)
MVSQALRLLCLLLGLQGCLAAVFVTQEEAHGVLHRRRRANAFLEELRPGSLERECKEE

QCSFEEAREIFKDAERTKLFWISYSDGDQCASSPCQNGGSCKDQLQSYICFCLPAFEGRN

CETHKDDQLICVNENGGCEQYCSDHTGTKRSCRCHEGYSLLADGVSCTPTVEYPCGKIP

ILEKRNASKPQGRGSDTPPPCPRCPAPELLGGPSVFLFPPKPKDTLMISRTPEVTCVVVDV

SHEDPEVQFKWYVDGVEVHNAKTKPREEQYNSTFRVVSVLTVLHQDWLNGKEYKCKV

SNKALPAPIEKTISKTKGQPREPQVYTLPPSREEMTKNQVSLTCLVKGFYPSDIAVEWESS

GQPENNYNTTPPMLDSDGSFFLYSKLTVDKSRWQQGNIFSCSVMHEALHNRFTQ

KSLSLSPGK

SEQ ID NO: 7: ICON3 (R435H)
AAGCTTTGCAGAGATTTCATCATGGTCTCCCAGGCCCTCAGGCTCCTCTGCCTTCTGC

TTGGGCTTCAGGGCTGCCTGGCTGCAGTCTTCGTAACCCAGGAGGAAGCCCACGGC

GTCCTGCACCGGCGCCGGCGCGCCAACGCGTTCCTGGAGGAGCTGCGGCCGGGCTC

CCTGGAGAGGGAGTGCAAGGAGGAGCAGTGCTCCTTCGAGGAGGCCCGGGAGATCT

TCAAGGACGCGGAGAGGACGAAGCTGTTCTGGATTTCTTACAGTGATGGTGACCAG

TGTGCCTCAAGTCCATGCCAGAATGGGGGCTCCTGCAAGGACCAGCTCCAGTCCTAT

ATCTGCTTCTGCCTCCCTGCCTTCGAGGGCCGGAACTGTGAGACGCACAAGGATGAC

CAGCTGATCTGTGTGAACGAGAACGGCGGCTGTGAGCAGTACTGCAGTGACCACAC

GGGCACCAAGCGCTCCTGTCGGTGCCACGAGGGGTACTCTCTGCTGGCAGACGGGG

TGTCCTGCACACCCACAGTTGAATATCCATGTGGAAAAATACCTATTCTAGAAAAAA

GAAATGCCAGCAAGCCCCAAGGGCGAATTGTGGGGGGCAAGGTGTGCCCCAAAGG

GGAGTGTCCATGGCAGGTCCTGTTGTTGGTGAATGGAGCTCAGTTGTGTGGGGGGAC

CCTGATCAACACCATCTGGGTGGTCTCCGCGGCCCACTGTTTCGACAAAATCAAGAA

CTGGAGGAACCTGATCGCGGTGCTCGGGGAGCACGACCTCAGCGAGCACGACGGGG

ATGAGCAGAGCCGGCGGGTGGCGCAGGTCATCATCCCCAGCACGTACGTCCCGGGC

ACCACCAACCACGACATCGCGCTGCTCCGCCTGCACCAGCCCGTGGTCCTCACTGAC

CATGTGGTGCCCCTCTGCCTGCCCGAACGGACGTTCTCTGAGAGGACGCTGGCCTTC

GTGCGCTTCTCATTGGTCAGCGGCTGGGGCCAGCTGCTGGACCGTGGCGCCACGGCC

CTGGAGCTCATGGTCCTCAACGTGCCCCGGCTGATGACCCAGGACTGCCTGCAGCAG

TCACGGAAGGTGGGAGACTCCCCAAATATCACGGAGTACATGTTCTGTGCCGGCTA

CTCGGATGGCAGCAAGGACTCCTGCGCGGGGGACAGTGGAGGCCCACATGCCACCC

ACTACCGGGGCACGTGGTACCTGACGGGCATCGTCAGCTGGGGCCAGGGCTGCGCA

ACCGTGGGCCACTTTGGGGTGTACACCAGGGTCTCCCAGTACATCGAGTGGCTGCAA

AAGCTCATGCGCTCAGAGCCACGCCCAGGAGTCCTCCTGCGAGCCCCATTTCCCGGA

TCCGACACACCTCCCCCGTGCCCAAGGTGCCCAGCACCTGAACTCCTGGGAGGACC

GTCAGTCTTCCTCTTCCCCCCAAAACCCAAGGATACCCTTATGATTTCCCGGACCCCT

GAGGTCACGTGCGTGGTGGTGGACGTGAGCCACGAAGACCCCGAGGTCCAGTTCAA

GTGGTACGTGGACGGCGTGGAGGTGCATAATGCCAAGACAAAGCCGCGGGAGGAG

CAGTACAACAGCACGTTCCGTGTGGTCAGCGTCCTCACCGTCCTGCACCAGGACTGG

CTGAACGGCAAGGAGTACAAGTGCAAGGTCTCCAACAAAGCCCTCCCAGCCCCCAT

CGAGAAAACCATCTCCAAAACCAAAGGACAGCCCCGAGAACCACAGGTGTACACCC

TGCCCCCATCCCGGGAGGAGATGACCAAGAACCAGGTCAGCCTGACCTGCCTGGTC

AAAGGCTTCTACCCCAGCGACATCGCCGTGGAGTGGGAGAGCAGCGGGCAGCCGGA

GAACAACTACAACACCACGCCTCCCATGCTGGACTCCGACGGCTCCTTCTTCCTCTA

CAGCAAGCTCACCGTGGACAAGAGCAGGTGGCAGCAGGGGAACATCTTCTCATGCT

-continued
```
CCGTGATGCATGAGGCTCTGCACAACCGCTTCACACAGAAGAGCCTCTCCCTGTCTC

CGGGTAAATGAGCGGCCGC
```

SEQ ID NO: 8: MONOMER OF ICON3 (R435H)
```
MVSQALRLLC LLLGLQGCLA AVFVTQEEAH GVLHRRRRAN AFLEELRPGS

LERECKEEQC SFEEAREIFK DAERTKLFWI SYSDGDQCAS SPCQNGGSCK

DQLQSYICFC LPAFEGRNCE THKDDQLICV NENGGCEQYC SDHTGTKRSC

RCHEGYSLLA DGVSCTPTVE YPCGKIPILE KRNASKPQGR IVGGKVCPKG

ECPWQVLLLV NGAQLCGGTL INTIWVVSAA HCFDKIKNWR NLIAVLGEHD

LSEHDGDEQS RRVAQVIIPS TYVPGTTNHD IALLRLHQPV VLTDHVVPLC

LPERTFSERT LAFVRFSLVS GWGQLLDRGA TALELMVLNV PRLMTQDCLQ

QSRKVGDSPN ITEYMFCAGY SDGSKDSCAG DSGGPHATHY RGTWYLTGIV

SWGQGCATVG HFGVYTRVSQ YIEWLQKLMR SEPRPGVLLR APFPGSDTPP

PCPRCPAPEL LGGPSVFLFP PKPKDTLMIS RTPEVTCVVV DVSHEDPEVQ

FKWYVDGVEV HNAKTKPREE QYNSTFRVVS VLTVLHQDWL NGKEYKCKVS

NKALPAPIEK TISKTKGQPR EPQVYTLPPS REEMTKNQVS LTCLVKGFYP

SDIAVEWESS GQPENNYNTT PPMLDSDGSF FLYSKLTVDK SRWQQGNIFS

CSVMHEALHN RFTQKSLSLS PGK
```

SEQ ID NO. 9: ICON1 (WT):
```
AAGCTTTGCAGAGATTTCATCATGGTCTCCCAGGCCCTCAGGCTCCTCTGCCTTCTG

CTTGGGCTTCAGGGCTGCCTGGCTGCAGTCTTCGTAACCCAGGAGGAAGCCCACGGC

GTCCTGCACCGGCGCCGGCGCGCCAACGCGTTCCTGGAGGAGCTGCGGCCGGGCTC

CCTGGAGAGGGAGTGCAAGGAGGAGCAGTGCTCCTTCGAGGAGGCCCGGGAGATCT

TCAAGGACGCGGAGAGGACGAAGCTGTTCTGGATTTCTTACAGTGATGGTGACCAG

TGTGCCTCAAGTCCATGCCAGAATGGGGGCTCCTGCAAGGACCAGCTCCAGTCCTAT

ATCTGCTTCTGCCTCCCTGCCTTCGAGGGCCGGAACTGTGAGACGCACAAGGATGAC

CAGCTGATCTGTGTGAACGAGAACGGCGGCTGTGAGCAGTACTGCAGTGACCACAC

GGGCACCAAGCGCTCCTGTCGGTGCCACGAGGGGTACTCTCTGCTGGCAGACGGGG

TGTCCTGCACACCCACAGTTGAATATCCATGTGGAAAAATACCTATTCTAGAAAAAA

GAAATGCCAGCAAGCCCCAAGGGCGAATTGTGGGGGGCAAGGTGTGCCCCAAAGG

GGAGTGTCCATGGCAGGTCCTGTTGTTGGTGAATGGAGCTCAGTTGTGTGGGGGGAC

CCTGATCAACACCATCTGGGTGGTCTCCGCGGCCCACTGTTTCGACAAAATCAAGAA

CTGGAGGAACCTGATCGCGGTGCTCGGGGAGCACGACCTCAGCGAGCACGACGGGG

ATGAGCAGAGCCGGCGGGTGGCGCAGGTCATCATCCCCAGCACGTACGTCCCGGGC

ACCACCAACCACGACATCGCGCTGCTCCGCCTGCACCAGCCCGTGGTCCTCACTGAC

CATGTGGTGCCCCTCTGCCTGCCCGAACGGACGTTCTCTGAGAGGACGCTGGCCTTC

GTGCGCTTCTCATTGGTCAGCGGCTGGGGCCAGCTGCTGGACCGTGGCGCCACGGCC

CTGGAGCTCATGGTCCTCAACGTGCCCCGGCTGATGACCCAGGACTGCCTGCAGCAG

TCACGGAAGGTGGGAGACTCCCCAAATATCACGGAGTACATGTTCTGTGCCGGCTA

CTCGGATGGCAGCAAGGACTCCTGCGCGGGGGACAGTGGAGGCCCACATGCCACCC

ACTACCGGGGCACGTGGTACCTGACGGGCATCGTCAGCTGGGGCCAGGGCTGCGCA

ACCGTGGGCCACTTTGGGGTGTACACCAGGGTCTCCCAGTACATCGAGTGGCTGCAA

AAGCTCATGCGCTCAGAGCCACGCCCAGGAGTCCTCCTGCGAGCCCCATTTCCCGGA
```

```
TCCGACAAAACTCACACATGCCCACCGTGCCCAGCACCTGAACTCCTGGGGGGACC

GTCAGTCTTCCTCTTCCCCCCAAAACCCAAGGACACCCTCATGATCTCCCGGACCCC

TGAGGTCACATGCGTGGTGGTGGACGTGAGCCACGAAGACCCTGAGGTCAAGTTCA

ACTGGTACGTGGACGGCGTGGAGGTGCATAATGCCAAGACAAAGCCGCGGGAGGA

GCAGTACAACAGCACGTACCGTGTGGTCAGCGTCCTCACCGTCCTGCACCAGGACTG

GCTGAATGGCAAGGAGTACAAGTGCAAGGTCTCCAACAAAGCCCTCCCAGCCCCCA

TCGAGAAACCATCTCCAAAGCCAAAGGGCAGCCCCGAGAACCACAGGTGTACGCC

CTGCCCCCATCCCGGGATGAGCTGACCAAGAACCAGGTCAGCCTGACCTGCCTGGTC

AAAGGCTTCTATCCCAGCGACATCGCCGTGGAGTGGGAGAGCAATGGGCAGCCGGA

GAACAACTACAAGACCACGCCTCCCGTGCTGGACTCCGACGGCTCCTTCTTCCTCTA

CAGCAAGCTCACCGTGGACAAGAGCAGGTGGCAGCAGGGGAACGTCTTCTCATGCT

CCGTGATGCATGAGGCTCTGCACAACCACTACACGCAGAAGAGCCTCTCCCTGTCTC

CGGGTAAATGATAAGCGGCCGC

SEQ ID NO: 10: MONOMER OF ICON1 (WT):
MVSQALRLLCLLLGLQGCLAAVFVTQEEAHGVLHRRRRANAFLEELRPGSLERECKEE

QCSFEEAREIFKDAERTKLFWISYSDGDQCASSPCQNGGSCKDQLQSYICFCLPAFEGRN

CETHKDDQLICVNENGGCEQYCSDHTGTKRSCRCHEGYSLLADGVSCTPTVEYPCGKIP

ILEKRNASKPQGRIVGGKVCPKGECPWQVULVNGAQLCGGTLINTIWVVSAAHCFDKI

KNWRNLIAVLGEHDLSEHDGDEQSRRVAQVIIPSTYVPGTTNHDIALLRLHQPVVLTDH

VVPLCLPERTFSERTLAFVRFSLVSGWGQLLDRGATALELMVLNVPRLMTQDCLQQSR

KVGDSPNITEYMFCAGYSDGSKDSCAGDSGGPHATHYRGTWYLTGIVSWGQGCATVG

HFGVYTRVSQYIEWLQKLMRSEPRPGVLLRAPFPGSDKTHTCPPCPAPELLGGPSVFLFP

PKPKDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYALPPSRDELTKN

QVSLTCLVKGFYPSDIAVEWESNGQPENNYKTTPPVLDSDGSFFLYSKLTVDKSRWQQG

NVFSCSVMHEALHNHYTQKSLSLSPGK

SEQ ID NO. 11: ICON1 (E333A)
AAGCTTTGCAGAGATTTCATCATGGTCTCCCAGGCCCTCAGGCTCCTCTGCCTTCTG

CTTGGGCTTCAGGGCTGCCTGGCTGCAGTCTTCGTAACCCAGGAGGAAGCCCACGGC

GTCCTGCACCGGCGCCGGCGCGCCAACGCGTTCCTGGAGGAGCTGCGGCCGGGCTC

CCTGGAGAGGGAGTGCAAGGAGGAGCAGTGCTCCTTCGAGGAGGCCCGGGAGATCT

TCAAGGACGCGGAGAGGACGAAGCTGTTCTGGATTTCTTACAGTGATGGTGACCAG

TGTGCCTCAAGTCCATGCCAGAATGGGGGCTCCTGCAAGGACCAGCTCCAGTCCTAT

ATCTGCTTCTGCCTCCCTGCCTTCGAGGGCCGGAACTGTGAGACGCACAAGGATGAC

CAGCTGATCTGTGTGAACGAGAACGGCGGCTGTGAGCAGTACTGCAGTGACCACAC

GGGCACCAAGCGCTCCTGTCGGTGCCACGAGGGGTACTCTCTGCTGGCAGACGGGG

TGTCCTGCACACCCACAGTTGAATATCCATGTGGAAAATACCTATTCTAGAAAAAA

GAAATGCCAGCAAGCCCCAAGGGCGAATTGTGGGGGGCAAGGTGTGCCCCAAAGG

GGAGTGTCCATGGCAGGTCCTGTTGTTGGTGAATGGAGCTCAGTTGTGTGGGGGAC

CCTGATCAACACCATCTGGGTGGTCTCCGCGCCCACTGTTTCGACAAAATCAAGAA

CTGGAGGAACCTGATCGCGGTGCTCGGGGAGCACGACCTCAGCGAGCACGACGGGG
```

-continued
ATGAGCAGAGCCGGCGGGTGGCGCAGGTCATCATCCCCAGCACGTACGTCCCGGGC

ACCACCAACCACGACATCGCGCTGCTCCGCCTGCACCAGCCCGTGGTCCTCACTGAC

CATGTGGTGCCCCTCTGCCTGCCCGAACGGACGTTCTCTGAGAGGACGCTGGCCTTC

GTGCGCTTCTCATTGGTCAGCGGCTGGGGCCAGCTGCTGGACCGTGGCGCCACGGCC

CTGGAGCTCATGGTCCTCAACGTGCCCCGGCTGATGACCCAGGACTGCCTGCAGCAG

TCACGGAAGGTGGGAGACTCCCCAAATATCACGGAGTACATGTTCTGTGCCGGCTA

CTCGGATGGCAGCAAGGACTCCTGCGCGGGGGACAGTGGAGGCCCACATGCCACCC

ACTACCGGGGCACGTGGTACCTGACGGGCATCGTCAGCTGGGGCCAGGGCTGCGCA

ACCGTGGGCCACTTTGGGGTGTACACCAGGGTCTCCCAGTACATCGAGTGGCTGCAA

AAGCTCATGCGCTCAGAGCCACGCCCAGGAGTCCTCCTGCGAGCCCCATTTCCCGGA

TCCGACAAAACTCACACATGCCCACCGTGCCCAGCACCTGAACTCCTGGGGGGACC

GTCAGTCTTCCTCTTCCCCCCAAAACCCAAGGACACCCTCATGATCTCCCGGACCCC

TGAGGTCACATGCGTGGTGGTGGACGTGAGCCACGAAGACCCTGAGGTCAAGTTCA

ACTGGTACGTGGACGGCGTGGAGGTGCATAATGCCAAGACAAAGCCGCGGGAGGA

GCAGTACAACAGCACGTACCGTGTGGTCAGCGTCCTCACCGTCCTGCACCAGGACTG

GCTGAATGGCAAGGAGTACAAGTGCAAGGTCTCCAACAAAGCCCTCCCAGCCCCCA

TCGCGAAAACCATCTCCAAAGCCAAAGGGCAGCCCCGAGAACCACAGGTGTACACC

CTGCCCCCATCCCGGGAGGAGATGACCAAGAACCAGGTCAGCCTGACCTGCCTGGT

CAAAGGCTTCTATCCCAGCGACATCGCCGTGGAGTGGGAGAGCAATGGGCAGCCGG

AGAACAACTACAAGACCACGCCTCCCGTGCTGGACTCCGACGGCTCCTTCTTCCTCT

ACAGCAAGCTCACCGTGGACAAGAGCAGGTGGCAGCAGGGGAACGTCTTCTCATGC

TCCGTGATGCATGAGGCTCTGCACAACCACTACACGCAGAAGAGCCTCTCCCTGTCT

CCGGGTAAATGATAAGCGGCCGC

SEQ ID NO: 12: MONOMER OF ICON1 (E333A)
MVSQALRLLCLLLGLQGCLAAVFVTQEEAHGVLHRRRRANAFLEELRPGSLERECKEE

QCSFEEAREIFKDAERTKLFWISYSDGDQCASSPCQNGGSCKDQLQSYICFCLPAFEGRN

CETHKDDQLICVNENGGCEQYCSDHTGTKRSCRCHEGYSLLADGVSCTPTVEYPCGKIP

ILEKRNASKPQGRIVGGKVCPKGECPWQVLLLVNGAQLCGGTLINTIWVVSAAHCFDKI

KNWRNLIAVLGEHDLSEHDGDEQSRRVAQVIIPSTYVPGTTNHDIALLRLHQPVVLTDH

VVPLCLPERTFSERTLAFVRFSLVSGWGQLLDRGATALELMVLNVPRLMTQDCLQQSR

KVGDSPNITEYMFCAGYSDGSKDSCAGDSGGPHATHYRGTWYLTGIVSWGQGCATVG

HFGVYTRVSQYIEWLQKLMRSEPRPGVLLRAPFPGSDKTHTCPPCPAPELLGGPSVFLFP

PKPKDTLMISRTPEVTCVVVDVSHEDPEVKFNWYVDGVEVHNAKTKPREEQYNSTYRV

VSVLTVLHQDWLNGKEYKCKVSNKALPAPIAKTISKAKGQPREPQVYTLPPSREEMTKN

QVSLTCLVKGFYPSDIAVEWESNGQPENNYKTTPPVLDSDGSFFLYSKLTVDKSRWQQG

NVFSCSVMHEALHNHYTQKSLSLS PGK

SEQ ID NO. 13: L-ICON1 (GenBank KX760097)
AAGCTTGAATTCGCCACCATGGTCTCCCAGGCCCTCAGGCTCCTCTGCCTTCTGCTTG

GCTTCAGGGCTGCCTGGCTGCAGTCTTCGTAACCCAGGAGGAAGCCCACGGCGTC

CTGCACCGGCGCCGGCGCGCCAACGCGTTCCTGGAGGAGCTGCGGCCGGGCTCCCT

GGAGAGGGAGTGCAAGGAGGAGCAGTGCTCCTTCGAGGAGGCCCGGGAGATCTTCA

AGGACGCGGAGAGGACGAAGCTGTTCTGGATTTCTTACAGTGATGGTGACCAGTGT

```
GCCTCAAGTCCATGCCAGAATGGGGGCTCCTGCAAGGACCAGCTCCAGTCCTATATC

TGCTTCTGCCTCCCTGCCTTCGAGGGCCGGAACTGTGAGACGCACAAGGATGACCAG

CTGATCTGTGTGAACGAGAACGGCGGCTGTGAGCAGTACTGCAGTGACCACACGGG

CACCAAGCGCTCCTGTCGGTGCCACGAGGGGTACTCTCTGCTGGCAGACGGGGTGTC

CTGCACACCCACAGTTGAATATCCATGTGGAAAAATACCTATTCTAGAAAAAAGAA

ATGCCAGCAAGCCCCAAGGGCGAGGATCCGCAGAGCCCAAATCTTGTGACAAAACT

CACACATGCCCACCGTGCCCAGCACCTGAACTCCTGGGGGACCGTCAGTCTTCCTC

TTCCCCCCAAAACCCAAGGACACCCTCATGATCTCCCGGACCCCTGAGGTCACATGC

GTGGTGGTGGACGTGAGCCACGAAGACCCTGAGGTCAAGTTCAACTGGTACGTGGA

CGGCGTGGAGGTGCATAATGCCAAGACAAAGCCGCGGGAGGAGCAGTACAACAGC

ACGTACCGTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAAAACCAT

CTCCAAAGCCAAAGGGCAGCCCCGAGAACCACAGGTGTACACCCTGCCCCCATCCC

GGGATGAGCTGACCAAGAACCAGGTCAGCCTGACCTGCCTGGTCAAAGGCTTCTAT

CCCAGCGACATCGCCGTGGAGTGGGAGAGCAATGGGCAGCCGGAGAACAACTACA

AGACCACGCCTCCCGTGCTGGACTCCGACGGCTCCTTCTTCCTCTACAGCAAGCTCA

CCGTGGACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGGTAAATG

ATAAGCGGCCGC

SEQ ID NO: 14: MONOMER OF L-ICON1
MVSQALRLLCLLLGLQGCLAAVFVTQEEAHGVLHRRRRANAFLEELRPGSLERECKEE

QCSFEEAREIFKDAERTKLFWISYSDGDQCASSPCQNGGSCKDQLQSYICFCLPAFEGRN

CETHKDDQLICVNENGGCEQVCSDHTGTKRSCRCHEGYSLLADGVSCTPTVEYPCGKIP

ILEKRNASKPQGRGSAEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCSVMHEALHN

HYTQKSLSLSPGK

SEQ ID NO. 15: L-ICON1(WT) (GenBank KX760098)
AAGCTTGAATTCGCCACCATGGTCTCCCAGGCCCTCAGGCTCCTCTGCCTTCTGCTTG

GGCTTCAGGGCTGCCTGGCTGCAGTCTTCGTAACCCAGGAGGAAGCCCACGGCGTC

CTGCACCGGCGCCGGCGCGCCAACGCGTTCCTGGAGGAGCTGCGGCCGGGCTCCCT

GGAGAGGGAGTGCAAGGAGGAGCAGTGCTCCTTCGAGGAGGCCCGGGAGATCTTCA

AGGACGCGGAGAGGACGAAGCTGTTCTGGATTTCTTACAGTGATGGTGACCAGTGT

GCCTCAAGTCCATGCCAGAATGGGGGCTCCTGCAAGGACCAGCTCCAGTCCTATATC

TGCTTCTGCCTCCCTGCCTTCGAGGGCCGGAACTGTGAGACGCACAAGGATGACCAG

CTGATCTGTGTGAACGAGAACGGCGGCTGTGAGCAGTACTGCAGTGACCACACGGG

CACCAAGCGCTCCTGTCGGTGCCACGAGGGGTACTCTCTGCTGGCAGACGGGGTGTC

CTGCACACCCACAGTTGAATATCCATGTGGAAAAATACCTATTCTAGAAAAAAGAA

ATGCCAGCAAGCCCCAAGGGCGAGGATCCGACAAAACTCACACATGCCCACCGTGC

CCAGCACCTGAACTCCTGGGGGACCGTCAGTCTTCCTCTTCCCCCCAAAACCCAAG
```

-continued

```
GACACCCTCATGATCTCCCGGACCCCTGAGGTCACATGCGTGGTGGTGGACGTGAGC

CACGAAGACCCTGAGGTCAAGTTCAACTGGTACGTGGACGGCGTGGAGGTGCATAA

TGCCAAGACAAAGCCGCGGGAGGAGCAGTACAACAGCACGTACCGTGTGGTCAGCG

TCCTCACCGTCCTGCACCAGGACTGGCTGAATGGCAAGGAGTACAAGTGCAAGGTC

TCCAACAAAGCCCTCCCAGCCCCCATCGAGAAAACCATCTCCAAAGCCAAAGGGCA

GCCCCGAGAACCACAGGTGTACGCCCTGCCCCCATCCCGGGATGAGCTGACCAAGA

ACCAGGTCAGCCTGACCTGCCTGGTCAAAGGCTTCTATCCCAGCGACATCGCCGTGG

AGTGGGAGAGCAATGGGCAGCCGGAGAACAACTACAAGACCACGCCTCCCGTGCTG

GACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTAC

ACGCAGAAGAGCCTCTCCCTGTCTCCGGGTAAATGATAAGCGGCCGC
```

SEQ ID NO: 16: MONOMER OF L-ICON1(WT)
MVSQALRLLCLLLGLQGCLAAVFVTQEEAHGVLHRRRRANAFLEELRPGSLERECKEE

QCSFEEAREIFKDAERTKLFWISYSDGDQCASSPCQNGGSCKDQLQSYICFCLPAFEGRN

CETHKDDQLICVNENGGCEQYCSDHTGTKRSCRCHEGYSLLADGVSCTPTVEYPCGKIP

ILEKRNASKPQGRGSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLNGKEYKC

KVSNKALPAPIEKTISKAKGQPREPQVYALPPSRDELTKNQVSLTCLVKGFYPSDIAVEW

ESNGQPENNYKTTPPVLDSDGSFFLYSKLTVDKSRWQQGNVFSCSVMHEALHNHYTQ

KSLSLSPGK

SEQ ID NO. 17: L-ICON1 (E333A) (GenBank KX760099)
```
AAGCTTGGATTCGCCACCATGGTCTCCCAGGCCCTCAGGCTCCTCTGCCTTCTGCTTG

GGCTTCAGGGCTGCCTGGCTGCAGTCTTCGTAACCCAGGAGGAAGCCCACGGCGTC

CTGCACCGGCGCCGGCGCGCCAACGCGTTCCTGGAGGAGCTGCGGCCGGGCTCCCT

GGAGAGGGAGTGCAAGGAGGAGCAGTGCTCCTTCGAGGAGGCCCGGGAGATCTTCA

AGGACGCGGAGAGGACGAAGCTGTTCTGGATTTCTTACAGTGATGGTGACCAGTGT

GCCTCAAGTCCATGCCAGAATGGGGGCTCCTGCAAGGACCAGCTCCAGTCCTATATC

TGCTTCTGCCTCCCTGCCTTCGAGGGCCGGAACTGTGAGACGCACAAGGATGACCAG

CTGATCTGTGTGAACGAGAACGGCGGCTGTGAGCAGTACTGCAGTGACCACACGGG

CACCAAGCGCTCCTGTCGGTGCCACGAGGGGTACTCTCTGCTGGCAGACGGGGTGTC

CTGCACACCCACAGTTGAATATCCATGTGGAAAAATACCTATTCTAGAAAAAAGAA

ATGCCAGCAAGCCCCAAGGGCGAGGATCCGACAAAACTCACACATGCCCACCGTGC

CCAGCACCTGAACTCCTGGGGGACCGTCAGTCTTCCTCTTCCCCCCAAAACCCAAG

GACACCCTCATGATCTCCCGGACCCCTGAGGTCACATGCGTGGTGGTGGACGTGAGC

CACGAAGACCCTGAGGTCAAGTTCAACTGGTACGTGGACGGCGTGGAGGTGCATAA

TGCCAAGACAAAGCCGCGGGAGGAGCAGTACAACAGCACGTACCGTGTGGTCAGCG

TCCTCACCGTCCTGCACCAGGACTGGCTGAATGGCAAGGAGTACAAGTGCAAGGTC
```

```
-continued
TCCAACAAAGCCCTCCCAGCCCCCATCGCGAAAACCATCTCCAAAGCCAAAGGGCA

GCCCCGAGAACCACAGGTGTACACCCTGCCCCCATCCCGGGAGGAGATGACCAAGA

ACCAGGTCAGCCTGACCTGCCTGGTCAAAGGCTTCTATCCCAGCGACATCGCCGTGG

AGTGGGAGAGCAATGGGCAGCCGGAGAACAACTACAAGACCACGCCTCCCGTGCTG

GACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTAC

ACGCAGAAGAGCCTCTCCCTGTCTCCGGGTAAATGATAAGCGGCCGC

SEQ ID NO: 18: MONOMER OF L-ICON1(E333A)
MVSQALRLLCLLLGLQGCLAAVFVTQEEAHGVLHRRRRANAFLEELRPGSLERECKEE

QCSFEEAREIFKDAERTKLFWISYSDGDQCASSPCQNGGSCKDQLQSYICFCLPAFEGRN

CETHKDDQLICVNENGGCEQYCSDHTGTKRSCRCHEGYSLLAGVSCTPTVEYPCGKIPIL

EKRNASKPQGRGSDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGKEYKCKV

SNKALPAPIAKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQ

KSLSLSPGK
```

TABLES

TABLE 1

Coagulation activities (IU/ml, mean ± SD) of L-ICON1, ICON(WT) and ICON(K341A)

| Concentration (nM) | L-ICON1 | ICON (K341A) | ICON (WT) | FVIIa-FFR | FVIIa |
|---|---|---|---|---|---|
| 10.00 (Coagulation activity)* | −0.013 ± 0.000 (−6.061 ± 0.000%) | 0.012 ± 0.003 (5.405 ± 1.177%) | 0.124 ± 0.019 (57.748 ± 8.654%) | 0.009 ± 0.001 (4.041 ± 0.521%) | 0.215 ± 0.001 (100.00 ± 0.437%)* |
| 5.00 | −0.013 ± 0.001 | 0.003 ± 0.002 | 0.083 ± 0.012 | 0.001 ± 0.001 | N/A |
| 2.50 | −0.014 ± 0.000 | −0.004 ± 0.003 | 0.056 ± 0.022 | −0.005 ± 0.001 | N/A |
| 1.25 | −0.013 ± 0.001 | −0.007 ± 0.001 | 0.014 ± 0.007 | −0.009 ± 0.000 | 0.131 ± 0.006** |

*For comparison with L-ICON1 and ICONs, the coagulation activity of 10 nM FVIIa is designated as 100%.
**The concentration of FVIIa was 1.00 nM, while other proteins were diluted to 1.25 nM.

TABLE 2

The fourth generation tissue factor-targeting ICONs with factor VII light chain as targeting domain (L-ICON4)

| L-ICON4 Subtypes | One peptide chain from L-ICON1 (Genbank accession no.) | One peptide chain from L-ICON3 (Genbank accession no.) |
|---|---|---|
| L-ICON4-1 | L-ICON1 (KX760097): SEQ ID NO: 14 | L-ICON3(WT) (KY223609): SEQ ID NO: 2 |
| L-ICON4-2 | L-ICON1 (KX760097): SEQ ID NO: 14 | L-ICON3(R435): SEQ ID NO: 6 |
| L-ICON4-3 | L-ICON1(WT) (KX760098): SEQ ID NO: 16 | L-ICON3(WT) (KY223609): SEQ ID NO: 2 |
| L-ICON4-4 | L-ICON1(WT) (KX760098): SEQ ID NO: 16 | L-ICON3(R435): SEQ ID NO: 6 |
| L-ICON4-5 | L-ICON1(E333A) (KX760099): SEQ ID NO: 18 | L-ICON3(WT) (KY223609): SEQ ID NO: 2 |
| L-ICON4-6 | L-ICON1(E333A) (KX760099): SEQ ID NO: 18 | SEQ ID NO: 6 |

TABLE 3

The fourth generation tissue factor-targeting ICONs with factor VII K341A as targeting domain (ICON4)

| ICON4 Subtypes | One peptide chain from ICON1 | One peptide chain from ICON3 (Genbank accession no.) |
|---|---|---|
| ICON4-1 | ICON1(WT) SEQ ID NO: 10 | ICON3(WT) (KY223610) SEQ ID NO: 4 |
| ICON4-2 | ICON1(WT) SEQ ID NO: 10 | ICON3(435) (KY223610) SEQ ID NO: 8 |
| ICON4-3 | ICON1(E333A) SEQ ID NO: 12 | ICON3(WT) (KY223610) SEQ ID NO: 4 |
| ICON4-4 | ICON1(E333A) SEQ ID NO: 12 | ICON3(435) (KY223610) SEQ ID NO: 8 |

REFERENCES

1. Morrissey J H, Fakhrai H and Edgington T S. Molecular cloning of the cDNA for tissue factor, the cellular receptor for the initiation of the coagulation protease cascade. Cell. 1987; 50(1):129-135.

2. Spicer E K, Horton R, Bloem L, Bach R, Williams K R, Guha A, Kraus J, Lin T C, Nemerson Y and Konigsberg W H. Isolation of cDNA clones coding for human tissue factor: primary structure of the protein and cDNA. Proceedings of the National Academy of Sciences of the United States of America. 1987; 84(15):5148-5152.
3. Konigsberg W H and Nemerson Y. Molecular cloning of the cDNA for human tissue factor. Cell. 1988; 52(5):639-640.
4. Nemerson Y. Tissue factor and the initiation of blood coagulation. Advances in experimental medicine and biology. 1987; 214:83-94.
5. Nemerson Y. Tissue factor and hemostasis. Blood. 1988; 71(1):1-8.
6. Contrino J, Hair G, Kreutzer D L and Rickles F R. In situ detection of tissue factor in vascular endothelial cells: correlation with the malignant phenotype of human breast disease. Nature medicine. 1996; 2(2):209-215.
7. Folkman J. Tumor angiogenesis and tissue factor. Nature medicine. 1996; 2(2): 167-168.
8. Hu Z, Sun Y and Garen A. Targeting tumor vasculature endothelial cells and tumor cells for immunotherapy of human melanoma in a mouse xenograft model. Proceedings of the National Academy of Sciences of the United States of America. 1999; 96(14):8161-8166.
9. Hu Z and Garen A. Targeting tissue factor on tumor vascular endothelial cells and tumor cells for immunotherapy in mouse models of prostatic cancer. Proceedings of the National Academy of Sciences of the United States of America. 2001; 98(21):12180-12185.
10. Cheng J, Xu J, Duanmu J, Zhou H, Booth C J and Hu Z. Effective treatment of human lung cancer by targeting tissue factor with a factor VH-targeted photodynamic therapy. Current cancer drug targets. 2011; 11(9):1069-1081.
11. Duanmu J, Cheng J, Xu J, Booth C J and Hu Z. Effective treatment of chemoresistant breast cancer in vitro and in vivo by a factor VII-targeted photodynamic therapy. British journal of cancer. 2011; 104(9):1401-1409.
12. Bora P S, Hu Z, Tezel T H, Sohn J H, Kang S G, Cruz J M, Bora N S, Garen A and Kaplan H J. Immunotherapy for choroidal neovascularization in a laser-induced mouse model simulating exudative (wet) macular degeneration. Proceedings of the National Academy of Sciences of the United States of America. 2003; 100(5):2679-2684.
13. Krikun G, Hu Z, Osteen K, Bruner-Tran K L, Schatz F, Taylor H S, Toti P, Arcuri F, Konigsberg W, Garen A, Booth C J and Lockwood C J. The immunoconjugate "icon" targets aberrantly expressed endothelial tissue factor causing regression of endometriosis. The American journal of pathology. 2010; 176(2):1050-1056.
14. Ferrara N. VEGF and the quest for tumour angiogenesis factors. Nature reviews Cancer. 2002; 2(10):795-803.
15. Klagsbrun M, Sullivan R, Smith S, Rybka R and Shing Y E. Purification of endothelial cell growth factors by heparin affinity chromatography. Methods in enzymology. 1987; 147:95-105.
16. Afuwape A O, Kiriakidis S and Paleolog E M. The role of the angiogenic molecule VEGF in the pathogenesis of rheumatoid arthritis. Histology and histopathology. 2002; 17(3): 961-972.
17. Fujimoto J, Sakaguchi H, Hirose R, Wen H and Tamaya T. Angiogenesis in endometriosis and angiogenic factors. Gynecologic and obstetric investigation. 1999; 48 Suppl 1:14-20.
18. Hu Z, Cheng J, Xu J, Ruf W and Lockwood C J. Tissue factor is an angiogenic-specific receptor for factor VII-targeted immunotherapy and photodynamic therapy. Angiogenesis. 2016.
19. Hu Z, Xu J, Cheng J, McMichael E, Yu L and Carson Iii W E. Targeting tissue factor as a novel therapeutic oncotarget for eradication of cancer stem cells isolated from tumor cell lines, tumor xenografts and patients of breast, lung and ovarian cancer. Oncotarget. 2016.
20. Vidal S J, Rodriguez-Bravo V, Galsky M, Cordon-Cardo C and Domingo-Domenech J. Targeting cancer stem cells to suppress acquired chemotherapy resistance. Oncogene. 2014; 33(36):4451-4463.
21. Moncharmont C, Levy A, Gilormini M, Bertrand G, Chargari C, Alphonse G, Ardail D, Rodriguez-Lafrasse C and Magne N. Targeting a cornerstone of radiation resistance: cancer stem cell. Cancer letters. 2012; 322(2):139-147.
22. Koch U, Krause M and Baumann M. Cancer stem cells at the crossroads of current cancer therapy failures—radiation oncology perspective. Seminars in cancer biology. 2010; 20(2):116-124.
23. Tezel T H, Bodek E, Sonmez K, Kaliappan S, Kaplan H J, Hu Z and Garen A. Targeting tissue factor for immunotherapy of choroidal neovascularization by intravitreal delivery of factor VII-Fc chimeric antibody. Ocul Immunol Inflamm. 2007; 15(1):3-10.
24. Hu Z and Garen A. Intratumoral injection of adenoviral vectors encoding tumor-targeted immunoconjugates for cancer immunotherapy. Proceedings of the National Academy of Sciences of the United States of America. 2000; 97(16):9221-9225.
25. Hu Z and Li J. Natural killer cells are crucial for the efficacy of Icon (factor VII/human IgG1 Fc) immunotherapy in human tongue cancer. BMC immunology. 2010; 11:49.
26. Hu Z, Rao B, Chen S and Duanmu J. Targeting tissue factor on tumour cells and angiogenic vascular endothelial cells by factor VII-targeted verteporfin photodynamic therapy for breast cancer in vitro and in vivo in mice. BMC cancer. 2010; 10:235.
27. Hu Z, Rao B, Chen S and Duanmu J. Selective and effective killing of angiogenic vascular endothelial cells and cancer cells by targeting tissue factor using a factor VII-targeted photodynamic therapy for breast cancer. Breast cancer research and treatment. 2011; 126(3):589-600.
28. Kim, J. K. et al. Mapping the site on human IgG for binding of the MHC class I-related receptor, FcRn. European journal of immunology 29, 2819-2825, doi:10.1002/(SICI)1521-4141(199909)29:09< 2819::AID-IMMU2819> 3.0.CO; 2-6 (1999).
28. Stapleton, N. M. et al. Competition for FcRn-mediated transport gives rise to short half-life of human IgG3 and offers therapeutic potential. Nature communications 2, 599, doi:10.1038/ncomms1608 (2011).

What is claimed is:

1. A composition comprising an immunoconjugate protein, wherein said immunoconjugate protein comprises a dimer comprising:
an Fc region of an IgG3 immunoglobulin conjugated to a Factor VII light chain and an Fc region of an IgG3 immunoglobulin conjugated to a Factor VII light chain, or
an Fc region of an IgG3 immunoglobulin conjugated to a Factor VII light chain and an Fc region of an IgG1 immunoglobulin conjugated to a Factor VII light chain,
wherein the Factor VII light chain does not comprise Factor VII heavy chain.

2. The composition of claim 1, wherein the immunoconjugate protein comprises a dimer comprising an Fc region of an IgG3 immunoglobulin conjugated to a Factor VII light chain and an Fc region of an IgG3 immunoglobulin conjugated to a Factor VII light chain, wherein the Factor VII light chain does not comprise Factor VII heavy chain.

3. The composition of claim 1, wherein the immunoconjugate protein comprises a dimer comprising an Fc region of an IgG3 immunoglobulin conjugated to a Factor VII light chain and an Fc region of an IgG1 immunoglobulin conjugated to a Factor VII light chain, wherein the Factor VII light chain does not comprise Factor VII heavy chain.

4. The composition of claim 1, wherein the Factor VII light chain comprises human or murine Factor VII.

5. The composition of claim 1, wherein the Fc region of the IgG3 immunoglobulin comprises a R435H mutation.

6. The composition of claim 1, wherein the Fc region of an IgG3 immunoglobulin conjugated to a Factor VII light chain comprises the amino acid sequence of SEQ ID NO: 2 or SEQ ID NO: 6.

7. The composition of claim 1, wherein the Fc region of an IgG1 immunoglobulin conjugated to a Factor VII light chain comprises the amino acid sequence of SEQ ID NO: 14, SEQ ID NO: 16, or SEQ ID NO: 18.

8. The composition of claim 1, wherein comprising:
the Fc region of the IgG3 immunoglobulin conjugated to the Factor VII light chain the amino acid sequence of SEQ ID NO: 2 and the Fc region of the IgG1 immunoglobulin conjugated to the Factor VII light chain comprises the amino acid sequence of SEQ ID NO: 14,
the Fc region of the IgG3 immunoglobulin conjugated to the Factor VII light chain amino acid sequence of SEQ ID NO: 2 and the Fc region of the IgG1 immunoglobulin conjugated to the Factor VII light chain comprises the amino acid sequence of SEQ ID NO: 16,
the Fc region of the IgG3 immunoglobulin conjugated to the Factor VII light chain comprises the amino acid sequence of SEQ ID NO: 2 and the Fc region of the IgG1 immunoglobulin conjugated to the Factor VII light chain comprises the amino acid sequence of SEQ ID NO: 18,
the Fc region of the IgG3 immunoglobulin conjugated to the Factor VII light chain-comprises the amino acid sequence of SEQ ID NO: 6 and the Fc region of the IgG1 immunoglobulin conjugated to the Factor VII light chain comprises the amino acid sequence of SEQ ID NO: 16, or
the Fc region of the IgG3 immunoglobulin conjugated to the Factor VII light chain-comprises the amino acid sequence of SEQ ID NO: 6 and the Fc region of the IgG1 immunoglobulin conjugated to the Factor VII light chain comprises the amino acid sequence of SEQ ID NO: 18.

9. A pharmaceutical composition comprising the composition of claim 1 and a pharmaceutically acceptable carrier.

10. A composition comprising the composition of claim 1 coupled to a photosensitizer.

11. The composition of claim 10, wherein the photosensitizer comprises a photodynamic dye.

* * * * *

SEQUENCE LISTING

<160> NUMBER OF SEQ ID NOS: 18

<210> SEQ ID NO 1
<211> LENGTH: 1285
<212> TYPE: DNA

<213> ORGANISM: Artificial Sequence
<220> FEATURE:
<223> OTHER INFORMATION: Synthetic Construct

<400> SEQUENCE: 1

```
aagcttgaat tcgccaccat ggtctcccag gccctcaggc tcctctgcct tctgcttggg      60
cttcagggct gcctggctgc agtcttcgta acccaggagg aagcccacgg cgtcctgcac     120
ggcgccggcg cgccaacgcg ttcctggagg agctgcggcc gggctccctg agagggagt     180
gcaaggagga gcagtgctcc ttcgaggagg cccgggagat cttcaaggac gcggagagga     240
cgaaagctgtt ctggatttct tacagtgatg gtgaccagtg tgcctcaagt ccatgccaga     300
atgggggctc ctgcaaggac cagctccagt cctatatctg cttctgcctc cctgccttcg     360
agggccggaa ctgtgagacg cacaaggatg accagctgat ctgtgtgaac gagaacggcg     420
gctgtgagca gtactgcagt gaccacacgg gcaccaagcg ctcctgtcgg tgccacgagg     480
ggtactctct gctggcagac ggggtgtcct gcacacccac agttgaatat ccatgtggaa     540
aaatacctat tctagaaaaa agaaatgcca gcaagcccca agggcgagga tccgacacac     600
ctccccccgtg cccaaggtgc ccagcacctg aactcctggg aggaccgtca gtcttcctct     660
tccccccaaa acccaaggat acccttatga tttcccggac ccctgaggtc acgtgcgtgg     720
tggtggacgt gagccacgaa gaccccgagg tccagttcaa gtggtacgtg gacggcgtgg     780
aggtgcataa tgccaagaca aagccgcggg aggagcagta caacagcacg ttccgtgtgg     840
tcagcgtcct caccgtcctg caccaggact ggctgaacgg caaggagtac aagtgcaagg     900
tctccaacaa agccctccca gccccatcg agaaaaccat ctccaaaacc aaaggacagc     960
cccgagaacc acaggtgtac accctgcccc catcccggga ggagatgacc aagaaccagg    1020
tcagcctgac ctgcctggtc aaaggcttct accccagcga catcgccgtg gagtgggaga    1080
gcagcgggca gccggagaac aactacaaca ccacgcctcc catgctggac tccgacggct    1140
ccttcttcct ctacagcaag ctcaccgtgg acaagagcag gtggcagcag gggaacatct    1200
tctcatgctc cgtgatgcat gaggctctgc acaaccgctt cacgcagaag agcctctccc    1260
tgtctccggg taaatgagcg gccgc                                          1285
```

<210> SEQ ID NO 2
<211> LENGTH: 419
<212> TYPE: PRT
<213> ORGANISM: Artificial Sequence
<220> FEATURE:
<223> OTHER INFORMATION: Synthetic Construct

<400> SEQUENCE: 2

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
                20                  25                  30

Leu His Arg Arg Arg Arg Ala Asn Ala Phe Leu Glu Glu Leu Arg Pro
            35                  40                  45

Gly Ser Leu Glu Arg Glu Cys Lys Glu Glu Gln Cys Ser Phe Glu Glu
        50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
```

| | | | | 100 | | | | 105 | | | | 110 | | |
|---|---|---|---|---|---|---|---|---|---|---|---|---|---|---|

Ala Phe Glu Gly Arg Asn Cys Glu Thr His Lys Asp Asp Gln Leu Ile
      115                    120                    125

Cys Val Asn Glu Asn Gly Gly Cys Glu Gln Tyr Cys Ser Asp His Thr
130                      135                    140

Gly Thr Lys Arg Ser Cys Arg Cys His Glu Gly Tyr Ser Leu Leu Ala
145                      150                    155                    160

Asp Gly Val Ser Cys Thr Pro Thr Val Glu Tyr Pro Cys Gly Lys Ile
                  165                    170                    175

Pro Ile Leu Glu Lys Arg Asn Ala Ser Lys Pro Gln Gly Arg Gly Ser
      180                    185                    190

Asp Thr Pro Pro Pro Cys Pro Arg Cys Pro Ala Pro Glu Leu Leu Gly
      195                    200                    205

Gly Pro Ser Val Phe Leu Phe Pro Pro Lys Pro Lys Asp Thr Leu Met
      210                    215                    220

Ile Ser Arg Thr Pro Glu Val Thr Cys Val Val Val Asp Val Ser His
225                      230                    235                    240

Glu Asp Pro Glu Val Gln Phe Lys Trp Tyr Val Asp Gly Val Glu Val
                  245                    250                    255

His Asn Ala Lys Thr Lys Pro Arg Glu Glu Gln Tyr Asn Ser Thr Phe
      260                    265                    270

Arg Val Val Ser Val Leu Thr Val Leu His Gln Asp Trp Leu Asn Gly
      275                    280                    285

Lys Glu Tyr Lys Cys Lys Val Ser Asn Lys Ala Leu Pro Ala Pro Ile
      290                    295                    300

Glu Lys Thr Ile Ser Lys Thr Lys Gly Gln Pro Arg Glu Pro Gln Val
305                      310                    315                    320

Tyr Thr Leu Pro Pro Ser Arg Glu Glu Met Thr Lys Asn Gln Val Ser
                  325                    330                    335

Leu Thr Cys Leu Val Lys Gly Phe Tyr Pro Ser Asp Ile Ala Val Glu
              340                    345                    350

Trp Glu Ser Ser Gly Gln Pro Glu Asn Asn Tyr Asn Thr Thr Pro Pro
      355                    360                    365

Met Leu Asp Ser Asp Gly Ser Phe Phe Leu Tyr Ser Lys Leu Thr Val
      370                    375                    380

Asp Lys Ser Arg Trp Gln Gln Gly Asn Ile Phe Ser Cys Ser Val Met
385                      390                    395                    400

His Glu Ala Leu His Asn Arg Phe Thr Gln Lys Ser Leu Ser Leu Ser
                  405                    410                    415

Pro Gly Lys

<210> SEQ ID NO 3
<211> LENGTH: 2051
<212> TYPE: DNA
<213> ORGANISM: Artificial Sequence
<220> FEATURE:
<223> OTHER INFORMATION: Synthetic Construct

<400> SEQUENCE: 3

```
aagctttgca gagatttcat catggtctcc caggcccctca ggctcctctg ccttctgctt      60
gggcttcagg gctgcctggc tgcagtcttc gtaacccagg aggaagccca cggcgtcctg     120
caccggcgcc ggcgcgccaa cgcgttcctg gaggagctgc ggcccgggct cctggagagg     180
gagtgcaagg aggagcagtg ctccttcgag gaggcccggg agatcttcaa ggacgcggag     240
```

```
aggacgaagc tgttctggat tcttacagt gatggtgacc agtgtgcctc aagtccatgc    300
cagaatgggg gctcctgcaa ggaccagctc cagtcctata tctgcttctg cctccctgcc    360
ttcgagggcc ggaactgtga cacgcacaag gatgaccagc tgatctgtgt gaacgagaac    420
ggcggctgtg agcagtactg cagtgaccac acgggcacca agcgctcctg tcggtgccac    480 gagggtact ctctgctggc agacggggtg tcctgcacac ccacagttga atatccatgt    540
ggaaaaatac ctattctaga aaaagaaat gccagcaagc cccaagggcg aattgtgggg    600
ggcaaggtgt gccccaaagg ggagtgtcca tggcaggtcc tgttgttggt gaatggagct    660
cagttgtgtg gggggaccct gatcaacacc atctgggtgg tctccgcggc ccactgtttc    720
gacaaaatca gaactggag gaacctgatc gcggtgctcg gggagcacga cctcagcgag    780
cacgacgggg atgagcagag ccggcgggtg gcgcaggtca tcatcccag cacgtacgtc    840 ccgggcacca ccaaccacga catcgcgctg ctccgcctgc accagcccgt ggtcctcact    900
gaccatgtgg tgcccctctg cctgcccgaa cggacgttct ctgagaggac gctggccttc    960
gtgcgcttct cattggtcag cggctggggc agctgctgg accgtggcgc cacggccctg   1020
gagctcatgg tcctcaacgt gccccggctg atgacccagg actgcctgca gcagtcacgg   1080
aaggtgggag actccccaaa tatcacggag tacatgttct gtgccggcta ctcggatggc   1140
agcaaggact cctgcgcggg ggacagtgga ggcccacatg ccacccacta ccggggcacg   1200
tggtacctga cgggcatcgt cagctgggc cagggctgcg caaccgtggg ccactttggg   1260
gtgtacacca gggtctccca gtacatcgag tggctgcaaa agctcatgcg ctcagagcca   1320
cgcccaggag tcctcctgcg agccccattt cccggatccg acacacctcc cccgtgccca   1380
aggtgcccag cacctgaact cctgggagga ccgtcagtct tcctcttccc cccaaaaccc   1440 aaggatacc ttatgatttc ccggacccct gaggtcacgt gcgtggtggt ggacgtgagc   1500
cacgaagacc ccgaggtcca gttcaagtgg tacgtggacg gcgtggaggt gcataatgcc   1560
aagacaaagc cgcgggagga gcagtacaac agcacgttcc gtgtggtcag cgtcctcacc   1620
gtcctgcacc aggactggct gaacggcaag gagtacaagt gcaaggtctc caacaaagcc   1680
ctcccagccc ccatcgagaa aaccatctcc aaaaccaaag acagccccg agaaccacag   1740 gtgtacaccc tgcccccatc ccgggaggag atgaccaaga accaggtcag cctgacctgc   1800
ctggtcaaag gcttctaccc cagcgacatc gccgtggagt gggagagcag cgggcagccg   1860
gagaacaact acaacaccac gcctcccatg ctggactccg acggctcctt cttcctctac   1920
agcaagctca ccgtggacaa gagcaggtgg cagcagggga acatcttctc atgctccgtg   1980
atgcatgagg ctctgcacaa ccgcttcacg cagaagagcc tctccctgtc tccgggtaaa   2040
tgagcggccg c                                                       2051
```

<210> SEQ ID NO 4
<211> LENGTH: 673
<212> TYPE: PRT
<213> ORGANISM: Artificial Sequence
<220> FEATURE:
<223> OTHER INFORMATION: Synthetic Construct

<400> SEQUENCE: 4

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro

```
                35                  40                  45
Gly Ser Leu Glu Arg Glu Cys Lys Glu Glu Gln Cys Ser Phe Glu Glu
 50                  55                  60

Ala Arg Glu Ile Phe Lys Asp Ala Glu Arg Thr Lys Leu Phe Trp Ile
 65                  70                  75                  80

Ser Tyr Ser Asp Gly Asp Gln Cys Ala Ser Pro Cys Gln Asn Gly
                 85                  90                  95

Gly Ser Cys Lys Asp Gln Leu Gln Ser Tyr Ile Cys Phe Cys Leu Pro
                100                 105                 110

Ala Phe Glu Gly Arg Asn Cys Glu Thr His Lys Asp Asp Gln Leu Ile
                115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                    165                 170                 175

Pro Ile Leu Glu Lys Arg Asn Ala Ser Lys Pro Gln Gly Arg Ile Val
                180                 185                 190

Gly Gly Lys Val Cys Pro Lys Gly Glu Cys Pro Trp Gln Val Leu Leu
                195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                    245                 250                 255

Asp Glu Gln Ser Arg Arg Val Ala Gln Val Ile Ile Pro Ser Thr Tyr
                260                 265                 270

Val Pro Gly Thr Thr Asn His Asp Ile Ala Leu Leu Arg Leu His Gln
                275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
                340                 345                 350

Arg Lys Val Gly Asp Ser Pro Asn Ile Thr Glu Tyr Met Phe Cys Ala
    355                 360                 365

Gly Tyr Ser Asp Gly Ser Lys Asp Ser Cys Ala Gly Asp Ser Gly Gly
370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro Gly Ser Asp Thr
    435                 440                 445

Pro Pro Pro Cys Pro Arg Cys Pro Ala Pro Glu Leu Leu Gly Gly Pro
450                 455                 460
```

```
Ser Val Phe Leu Phe Pro Lys Pro Lys Asp Thr Leu Met Ile Ser
465                 470                 475                 480

Arg Thr Pro Glu Val Thr Cys Val Val Val Asp Val Ser His Glu Asp
            485                 490                 495

Pro Glu Val Gln Phe Lys Trp Tyr Val Asp Gly Val Glu Val His Asn
                500                 505                 510

Ala Lys Thr Lys Pro Arg Glu Glu Gln Tyr Asn Ser Thr Phe Arg Val
            515                 520                 525

Val Ser Val Leu Thr Val Leu His Gln Asp Trp Leu Asn Gly Lys Glu
530                 535                 540

Tyr Lys Cys Lys Val Ser Asn Lys Ala Leu Pro Ala Pro Ile Glu Lys
545                 550                 555                 560

Thr Ile Ser Lys Thr Lys Gly Gln Pro Arg Glu Pro Gln Val Tyr Thr
                565                 570                 575

Leu Pro Pro Ser Arg Glu Glu Met Thr Lys Asn Gln Val Ser Leu Thr
            580                 585                 590

Cys Leu Val Lys Gly Phe Tyr Pro Ser Asp Ile Ala Val Glu Trp Glu
                595                 600                 605

Ser Ser Gly Gln Pro Glu Asn Asn Tyr Asn Thr Thr Pro Pro Met Leu
            610                 615                 620

Asp Ser Asp Gly Ser Phe Phe Leu Tyr Ser Lys Leu Thr Val Asp Lys
625                 630                 635                 640

Ser Arg Trp Gln Gln Gly Asn Ile Phe Ser Cys Ser Val Met His Glu
                645                 650                 655

Ala Leu His Asn Arg Phe Thr Gln Lys Ser Leu Ser Leu Ser Pro Gly
            660                 665                 670

Lys

<210> SEQ ID NO 5
<211> LENGTH: 1286
<212> TYPE: DNA
<213> ORGANISM: Artificial Sequence
<220> FEATURE:
<223> OTHER INFORMATION: Synthetic Construct

<400> SEQUENCE: 5
aagcttgaat cgccaccatg gtctcccag gccctcaggc tcctctgcct tctgcttggg      60
cttcagggct gcctggctgc agtcttcgta acccaggagg aagcccacgg cgtcctgcac    120
cggcgccggc gcgccaacgc gttcctggag gagctgcggc cgggctccct ggagagggag    180
tgcaaggagg agcagtgctc cttcgaggag gcccgggaga tcttcaagga cgcggagagg    240
acgaagctgt tctggatttc ttacagtgat ggtgaccagt gtgcctcaag tccatgccag    300
aatgggggct cctgcaagga ccagctccag tcctatatct gcttctgcct ccctgccttc    360
gagggccgga actgtgagac gcacaaggat gaccagctga tctgtgtgaa cgagaacggc    420
ggctgtgagc agtactgcag tgaccacacg ggcaccaagc gctcctgtcg gtgccacgag    480
gggtactctc tgctggcaga cggggtgtcc tgcacaccca cagttgaata tccatgtgga    540
aaaataccta ttctagaaaa aagaaatgcc agcaagcccc aagggcgagg atccgacaca    600
cctcccccgt gcccaaggtg cccagcacct gaactcctgg ggaccgtc agtcttcctc      660 ttccccccaa acccaagga taccttatg atttcccgga cccctgaggt cacgtgcgtg      720
gtggtggacg tgagccacga agaccccgag gtccagttca gtggtacgt ggacggcgtg     780 gaggtgcata atgccaagac aaagccgcgg gaggagcagt acaacagcac gttccgtgtg    840
```

-continued

```
gtcagcgtcc tcaccgtcct gcaccaggac tggctgaacg gcaaggagta caagtgcaag      900
gtctccaaca aagccctccc agcccccatc gagaaaacca tctccaaaac caaaggacag      960
ccccgagaac acaggtgta cacctgccc ccatcccggg aggagatgac caagaaccag       1020
gtcagcctga cctgcctggt caaaggcttc taccccagcg acatcgccgt ggagtgggag     1080
agcagcgggc agccggagaa caactacaag accacgcctc ccatgctgga ctccgacggc     1140
tccttcttcc tctacagcaa gctcaccgtg gacaagagca ggtggcagca ggggaacatc     1200
ttctcatgct ccgtgatgca tgaggctctg cacaaccact tcacacagaa gagcctctcc     1260
ctgtctccgg gtaaatgagc ggccgc                                          1286
```

<210> SEQ ID NO 6
<211> LENGTH: 419
<212> TYPE: PRT
<213> ORGANISM: Artificial Sequence
<220> FEATURE:
<223> OTHER INFORMATION: Synthetic Construct

<400> SEQUENCE: 6

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Ser
            180                 185                 190

Asp Thr Pro Pro Pro Cys Pro Arg Cys Pro Ala Pro Glu Leu Leu Gly
        195                 200                 205

Gly Pro Ser Val Phe Leu Phe Pro Pro Lys Pro Lys Asp Thr Leu Met
    210                 215                 220

Ile Ser Arg Thr Pro Glu Val Thr Cys Val Val Val Asp Val Ser His
225                 230                 235                 240

Glu Asp Pro Glu Val Gln Phe Lys Trp Tyr Val Asp Gly Val Glu Val
                245                 250                 255

His Asn Ala Lys Thr Lys Pro Arg Glu Glu Gln Tyr Asn Ser Thr Phe
            260                 265                 270

Arg Val Val Ser Val Leu Thr Val Leu His Gln Asp Trp Leu Asn Gly
```

```
                275                 280                 285
Lys Glu Tyr Lys Cys Lys Val Ser Asn Lys Ala Leu Pro Ala Pro Ile
            290                 295                 300
Glu Lys Thr Ile Ser Lys Thr Lys Gly Gln Pro Arg Glu Pro Gln Val
305                 310                 315                 320
Tyr Thr Leu Pro Pro Ser Arg Glu Glu Met Thr Lys Asn Gln Val Ser
                325                 330                 335
Leu Thr Cys Leu Val Lys Gly Phe Tyr Pro Ser Asp Ile Ala Val Glu
            340                 345                 350
Trp Glu Ser Ser Gly Gln Pro Glu Asn Asn Tyr Asn Thr Thr Pro Pro
                355                 360                 365
Met Leu Asp Ser Asp Gly Ser Phe Phe Leu Tyr Ser Lys Leu Thr Val
            370                 375                 380
Asp Lys Ser Arg Trp Gln Gln Gly Asn Ile Phe Ser Cys Ser Val Met
385                 390                 395                 400
His Glu Ala Leu His Asn His Phe Thr Gln Lys Ser Leu Ser Leu Ser
                405                 410                 415
Pro Gly Lys

<210> SEQ ID NO 7
<211> LENGTH: 2051
<212> TYPE: DNA
<213> ORGANISM: Artificial Sequence
<220> FEATURE:
<223> OTHER INFORMATION: Synthetic Construct

<400> SEQUENCE: 7
aagctttgca gagatttcat catggtctcc caggccctca ggctcctctg ccttctgctt      60
gggcttcagg gctgcctggc tgcagtcttc gtaacccagg aggaagccca cggcgtcctg     120
caccggcgcc ggcgcgccaa cgcgttcctg gaggagctgc ggccgggctc cctggagagg     180
gagtgcaagg aggagcagtg ctccttcgag gaggcccggg agatcttcaa ggacgcggag     240
aggacgaagc tgttctggat ttcttacagt gatggtgacc agtgtgcctc aagtccatgc     300
cagaatgggg gctcctgcaa ggaccagctc cagtcctata tctgcttctg cctccctgcc     360
ttcgagggcc ggaactgtga cgcacaag gatgaccagc tgatctgtgt gaacgagaac     420
ggcggctgtg agcagtactg cagtgaccac acgggcacca gcgctcctg tcggtgccac     480
gagggtact ctctgctgg agacggggtg tcctgcacac ccacagttga atatccatgt     540
ggaaaaatac ctattctaga aaaagaaat gccagcaagc cccaagggcg aattgtgggg     600
ggcaaggtgt gccccaaagg ggagtgtcca tggcaggtcc tgttgttggt gaatggagct     660
cagttgtgtg ggggaccct gatcaacacc atctgggtgg tctccgcggc ccactgtttc     720
gacaaaatca gaactggag gaacctgatc gcggtgctcg gggagcacga cctcagcgag     780
cacgacgggg atgagcagag ccggcgggtg gcgcaggtca tcatcccag cacgtacgtc     840
ccgggcacca ccaaccacga catcgcgctg ctccgcctgc accagcccgt ggtcctcact     900
gaccatgtgg tgccctctg cctgcccgaa cggacgttct ctgagaggac gctggccttc     960
gtgcgcttct cattggtcag cggctggggc cagctgctgg accgtggcgc cacggccctg    1020
gagctcatgg tcctcaacgt gccccggctg atgacccagg actgcctgca gcagtcacgg    1080
aaggtgggag actcccccaa atatcacgag tacatgttct gtgccggcta ctcggatggc    1140
agcaaggact cctgcgcggg ggacagtgga ggcccacatg ccacccacta ccggggcacg    1200
tggtacctga cgggcatcgt cagctggggc cagggctgcg caaccgtggg ccactttggg    1260
```

```
gtgtacacca gggtctccca gtacatcgag tggctgcaaa agctcatgcg ctcagagcca   1320
cgcccaggag tcctcctgcg agccccattt cccggatccg acacacctcc cccgtgccca   1380
aggtgcccag cacctgaact cctgggagga ccgtcagtct tcctcttccc cccaaaaccc   1440 aaggatccc ttatgatttc ccggacccct gaggtcacgt gcgtggtggt ggacgtgagc   1500
cacgaagacc ccgaggtcca gttcaagtgg tacgtggacg gcgtggaggt gcataatgcc   1560
aagacaaagc cgcggagga gcagtacaac agcacgttcc gtgtggtcag cgtcctcacc   1620
gtcctgcacc aggactggct gaacggcaag gagtacaagt gcaaggtctc caacaaagcc   1680
ctcccagccc ccatcgagaa aaccatctcc aaaaccaaag acagccccg agaaccacag   1740 gtgtacaccc tgcccccatc ccgggaggag atgaccaaga accaggtcag cctgacctgc   1800
ctggtcaaag gcttctaccc cagcgacatc gccgtggagt gggagagcag cgggcagccg   1860
gagaacaact acaacaccac gcctcccatg ctggactccg acggctcctt cttcctctac   1920
agcaagctca ccgtggacaa gagcaggtgg cagcagggga acatcttctc atgctccgtg   1980
atgcatgagg ctctgcacaa ccgcttcaca cagaagagcc tctccctgtc tccgggtaaa   2040
tgagcggccg c                                                        2051

<210> SEQ ID NO 8
<211> LENGTH: 673
<212> TYPE: PRT
<213> ORGANISM: Artificial Sequence
<220> FEATURE:
<223> OTHER INFORMATION: Synthetic Construct

<400> SEQUENCE: 8

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
```

```
                210               215               220
Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                    245                 250                 255

Asp Glu Gln Ser Arg Arg Val Ala Gln Val Ile Ile Pro Ser Thr Tyr
                260                 265                 270

Val Pro Gly Thr Thr Asn His Asp Ile Ala Leu Leu Arg Leu His Gln
            275                 280                 285

Pro Val Val Leu Thr Asp His Val Val Pro Leu Cys Leu Pro Glu Arg
        290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
                    340                 345                 350

Arg Lys Val Gly Asp Ser Pro Asn Ile Thr Glu Tyr Met Phe Cys Ala
                355                 360                 365

Gly Tyr Ser Asp Gly Ser Lys Asp Ser Cys Ala Gly Asp Ser Gly Gly
            370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro Gly Ser Asp Thr
            435                 440                 445

Pro Pro Pro Cys Pro Arg Cys Pro Ala Pro Glu Leu Leu Gly Gly Pro
        450                 455                 460

Ser Val Phe Leu Phe Pro Pro Lys Pro Lys Asp Thr Leu Met Ile Ser
465                 470                 475                 480

Arg Thr Pro Glu Val Thr Cys Val Val Val Asp Val Ser His Glu Asp
                485                 490                 495

Pro Glu Val Gln Phe Lys Trp Tyr Val Asp Gly Val Glu Val His Asn
                500                 505                 510

Ala Lys Thr Lys Pro Arg Glu Glu Gln Tyr Asn Ser Thr Phe Arg Val
            515                 520                 525

Val Ser Val Leu Thr Val Leu His Gln Asp Trp Leu Asn Gly Lys Glu
        530                 535                 540

Tyr Lys Cys Lys Val Ser Asn Lys Ala Leu Pro Ala Pro Ile Glu Lys
545                 550                 555                 560

Thr Ile Ser Lys Thr Lys Gly Gln Pro Arg Glu Pro Gln Val Tyr Thr
                565                 570                 575

Leu Pro Pro Ser Arg Glu Glu Met Thr Lys Asn Gln Val Ser Leu Thr
                580                 585                 590

Cys Leu Val Lys Gly Phe Tyr Pro Ser Asp Ile Ala Val Glu Trp Glu
            595                 600                 605

Ser Ser Gly Gln Pro Glu Asn Asn Tyr Asn Thr Thr Pro Pro Met Leu
        610                 615                 620

Asp Ser Asp Gly Ser Phe Phe Leu Tyr Ser Lys Leu Thr Val Asp Lys
625                 630                 635                 640
```

Ser Arg Trp Gln Gln Gly Asn Ile Phe Ser Cys Ser Val Met His Glu
                645                 650                 655

Ala Leu His Asn His Phe Thr Gln Lys Ser Leu Ser Leu Ser Pro Gly
            660                 665                 670

Lys

<210> SEQ ID NO 9
<211> LENGTH: 2054
<212> TYPE: DNA
<213> ORGANISM: Artificial Sequence
<220> FEATURE:
<223> OTHER INFORMATION: Synthetic Construct

<400> SEQUENCE: 9

| | | | | | |
|---|---|---|---|---|---|
| aagctttgca | gagatttcat | catggtctcc | caggccctca | ggctcctctg | ccttctgctt | 60 |
| gggcttcagg | gctgcctggc | tgcagtcttc | gtaacccagg | aggaagccca | cggcgtcctg | 120 |
| caccggcgcc | ggcgcgccaa | cgcgttcctg | gaggagctgc | ggccgggctc | cctggagagg | 180 |
| gagtgcaagg | aggagcagtg | ctccttcgag | gaggcccggg | agatcttcaa | ggacgcggag | 240 |
| aggacgaagc | tgttctggat | ttcttacagt | gatggtgacc | agtgtgcctc | aagtccatgc | 300 |
| cagaatgggg | gctcctgcaa | ggaccagctc | cagtcctata | tctgcttctg | cctccctgcc | 360 |
| ttcgagggcc | ggaactgtga | gacgcacaag | gatgaccagc | tgatctgtgt | gaacgagaac | 420 |
| ggcggctgtg | agcagtactg | cagtgaccac | acgggcacca | agcgctcctg | tcggtgccac | 480 |
| gagggtact | ctctgctggc | agacggggtg | tcctgcacac | ccacagttga | atatccatgt | 540 |
| ggaaaaatac | ctattctaga | aaaagaaat | gccagcaagc | cccaagggcg | aattgtgggg | 600 |
| ggcaaggtgt | gccccaaagg | ggagtgtcca | tggcaggtcc | tgttgttggt | gaatggagct | 660 |
| cagttgtgtg | gggggaccct | gatcaacacc | atctgggtgg | tctccgcggc | ccactgtttc | 720 |
| gacaaaatca | gaactggag | gaacctgatc | gcggtgctcg | gggagcacga | cctcagcgag | 780 |
| cacgacgggg | atgagcagag | ccggcgggtg | gcgcaggtca | tcatcccag | cacgtacgtc | 840 |
| ccgggcacca | ccaaccacga | catcgcgctg | ctccgcctgc | accagcccgt | ggtcctcact | 900 |
| gaccatgtgg | tgcccctctg | cctgcccgaa | cggacgttct | ctgagaggac | gctggccttc | 960 |
| gtgcgcttct | cattggtcag | cggctggggc | cagctgctgg | accgtggcgc | cacggccctg | 1020 |
| gagctcatgg | tcctcaacgt | gccccggctg | atgacccagg | actgcctgca | gcagtcacgg | 1080 |
| aaggtgggag | actccccaaa | tatcacggag | tacatgttct | gtgccggcta | ctcggatggc | 1140 |
| agcaaggact | cctgcgcggg | ggacagtgga | ggcccacatg | ccacccacta | ccggggcacg | 1200 |
| tggtacctga | cgggcatcgt | cagctggggc | cagggctgcg | caaccgtggg | ccactttggg | 1260 |
| gtgtacacca | gggtctccca | gtacatcgag | tggctgcaaa | agctcatgcg | ctcagagcca | 1320 |
| cgcccaggag | tcctcctgcg | agccccattt | cccggatccg | acaaaactca | cacatgccca | 1380 |
| ccgtgcccag | cacctgaact | cctggggga | ccgtcagtct | tcctcttccc | cccaaaaccc | 1440 |
| aaggacaccc | tcatgatctc | ccggacccct | gaggtcacat | gcgtggtggt | ggacgtgagc | 1500 |
| cacgaagacc | ctgaggtcaa | gttcaactgg | tacgtggacg | gcgtggaggt | gcataatgcc | 1560 |
| aagacaaagc | cgcgggagga | gcagtacaac | agcacgtacc | gtgtggtcag | cgtcctcacc | 1620 |
| gtcctgcacc | aggactggct | gaatggcaag | gagtacaagt | gcaaggtctc | caacaaagcc | 1680 |
| ctcccagccc | ccatcgagaa | aaccatctcc | aaagccaaag | ggcagccccg | agaaccacag | 1740 |
| gtgtacgccc | tgcccccatc | ccgggatgag | ctgaccaaga | accaggtcag | cctgacctgc | 1800 |

-continued

```
ctggtcaaag gcttctatcc cagcgacatc gccgtggagt gggagagcaa tgggcagccg      1860
gagaacaact acaagaccac gcctcccgtg ctggactccg acggctcctt cttcctctac      1920
agcaagctca ccgtggacaa gagcaggtgg cagcagggga acgtcttctc atgctccgtg      1980
atgcatgagg ctctgcacaa ccactacacg cagaagagcc tctccctgtc tccgggtaaa      2040
tgataagcgg ccgc                                                        2054
```

<210> SEQ ID NO 10
<211> LENGTH: 673
<212> TYPE: PRT
<213> ORGANISM: Artificial Sequence
<220> FEATURE:
<223> OTHER INFORMATION: Synthetic Construct

<400> SEQUENCE: 10

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320
```

Gly Trp Gly Gln Leu Leu Asp Arg Gly Ala Thr Ala Leu Glu Leu Met
            325                 330                 335

Val Leu Asn Val Pro Arg Leu Met Thr Gln Asp Cys Leu Gln Gln Ser
        340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Ala Gly Asp Ser Gly Gly
        370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
            405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Ser Asp Lys
            435                 440                 445

Thr His Thr Cys Pro Pro Cys Pro Ala Pro Glu Leu Leu Gly Gly Pro
        450                 455                 460

Ser Val Phe Leu Phe Pro Pro Lys Pro Lys Asp Thr Leu Met Ile Ser
465                 470                 475                 480

Arg Thr Pro Glu Val Thr Cys Val Val Val Asp Val Ser His Glu Asp
            485                 490                 495

Pro Glu Val Lys Phe Asn Trp Tyr Val Asp Gly Val Glu Val His Asn
            500                 505                 510

Ala Lys Thr Lys Pro Arg Glu Glu Gln Tyr Asn Ser Thr Tyr Arg Val
        515                 520                 525

Val Ser Val Leu Thr Val Leu His Gln Asp Trp Leu Asn Gly Lys Glu
        530                 535                 540

Tyr Lys Cys Lys Val Ser Asn Lys Ala Leu Pro Ala Pro Ile Glu Lys
545                 550                 555                 560

Thr Ile Ser Lys Ala Lys Gly Gln Pro Arg Glu Pro Gln Val Tyr Ala
            565                 570                 575

Leu Pro Pro Ser Arg Asp Glu Leu Thr Lys Asn Gln Val Ser Leu Thr
            580                 585                 590

Cys Leu Val Lys Gly Phe Tyr Pro Ser Asp Ile Ala Val Glu Trp Glu
            595                 600                 605

Ser Asn Gly Gln Pro Glu Asn Asn Tyr Lys Thr Thr Pro Pro Val Leu
        610                 615                 620

Asp Ser Asp Gly Ser Phe Phe Leu Tyr Ser Lys Leu Thr Val Asp Lys
625                 630                 635                 640

Ser Arg Trp Gln Gln Gly Asn Val Phe Ser Cys Ser Val Met His Glu
            645                 650                 655

Ala Leu His Asn His Tyr Thr Gln Lys Ser Leu Ser Leu Ser Pro Gly
            660                 665                 670

Lys

<210> SEQ ID NO 11
<211> LENGTH: 2054
<212> TYPE: DNA
<213> ORGANISM: Artificial Sequence
<220> FEATURE:
<223> OTHER INFORMATION: Synthetic Construct

<400> SEQUENCE: 11

```
aagctttgca gagatttcat catggtctcc caggccctca ggctcctctg ccttctgctt      60
gggcttcagg gctgcctggc tgcagtcttc gtaacccagg aggaagccca cggcgtcctg     120
caccggcgcc ggcgcgccaa cgcgttcctg gaggagctgc ggccgggctc cctggagagg     180
gagtgcaagg aggagcagtg ctccttcgag gaggcccggg agatcttcaa ggacgcggag     240
aggacgaagc tgttctggat tcttacagt gatggtgacc agtgtgcctc aagtccatgc      300
cagaatgggg gctcctgcaa ggaccagctc cagtcctata tctgcttctg cctccctgcc     360
ttcgagggcc ggaactgtga gacgcacaag gatgaccagc tgatctgtgt gaacgagaac     420
ggcggctgtg agcagtactg cagtgaccac acgggcacca gcgctcctg tcggtgccac      480
gagggtact ctctgctggc agacggggtg tcctgcacac ccacagttga atatccatgt      540
ggaaaaatac ctattctaga aaaagaaat gccagcaagc cccaagggcg aattgtgggg      600
ggcaaggtgt gccccaaagg ggagtgtcca tggcaggtcc tgttgttggt gaatggagct     660
cagttgtgtg gggggaccct gatcaacacc atctgggtgg tctccgcggc ccactgtttc     720
gacaaaatca gaactggag gaacctgatc gcggtgctcg gggagcacga cctcagcgag      780
cacgacgggg atgagcagag ccggcgggtg gcgcaggtca tcatcccag cacgtacgtc      840
ccgggcacca ccaaccacga catcgcgctg ctccgcctgc accagcccgt ggtcctcact     900
gaccatgtgg tgccctctg cctgcccgaa cggacgttct ctgagaggac gctggccttc     960
gtgcgcttct cattggtcag cggctggggc cagctgctgg accgtggcgc cacggccctg    1020
gagctcatgg tcctcaacgt gccccggctg atgacccagg actgcctgca gcagtcacgg    1080
aaggtgggag actccccaaa tatcacggag tacatgttct gtgccggcta ctcggatggc    1140
agcaaggact cctgcgcggg ggacagtgga ggcccacatg ccacccacta ccggggcacg    1200
tggtacctga cgggcatcgt cagctgggc cagggctgcg caaccgtggg ccactttggg     1260
gtgtacacca gggtctccca gtacatcgag tggctgcaaa agctcatgcg ctcagagcca    1320
cgcccaggag tcctcctgcg agccccattt cccggatccg acaaaactca cacatgccca    1380
ccgtgcccag cacctgaact cctgggggga ccgtcagtct tcctcttccc cccaaaaccc    1440
aaggacaccc tcatgatctc ccggacccct gaggtcacat gcgtggtggt ggacgtgagc    1500
cacgaagacc ctgaggtcaa gttcaactgg tacgtggacg gcgtggaggt gcataatgcc    1560
aagacaaagc cgcggaggga gcagtacaac agcacgtacc gtgtggtcag cgtcctcacc    1620
gtcctgcacc aggactggct gaatggcaag gagtacaagt gcaaggtctc caacaaagcc    1680
ctcccagccc ccatcgcgaa aaccatctcc aaagccaaag gcagccccg agaaccacag      1740
gtgtacaccc tgcccccatc ccgggaggag atgaccaaga accaggtcag cctgacctgc    1800
ctggtcaaag gcttctatcc cagcgacatc gccgtggagt gggagagcaa tgggcagccg    1860
gagaacaact acaagaccac gcctcccgtg ctggactccg acggctcctt cttcctctac    1920
agcaagctca ccgtggacaa gagcaggtgg cagcagggga acgtcttctc atgctccgtg    1980
atgcatgagg ctctgcacaa ccactacacg cagaagagcc tctccctgtc tccgggtaaa    2040
tgataagcgg ccgc                                                      2054
```

<210> SEQ ID NO 12
<211> LENGTH: 673
<212> TYPE: PRT
<213> ORGANISM: Artificial Sequence
<220> FEATURE:
<223> OTHER INFORMATION: Synthetic Construct

<400> SEQUENCE: 12

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Ala Asn Ala Phe Leu Glu Glu Leu Arg Pro
        35                  40                  45

Gly Ser Leu Glu Arg Glu Cys Lys Glu Glu Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
            115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
            195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
            245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
    275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
            325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Ala Gly Asp Ser Gly Gly
            370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
            405                 410                 415
```

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro Gly Ser Asp Lys
            435                 440                 445

Thr His Thr Cys Pro Pro Cys Pro Ala Pro Glu Leu Leu Gly Gly Pro
        450                 455                 460

Ser Val Phe Leu Phe Pro Pro Lys Pro Lys Asp Thr Leu Met Ile Ser
465                 470                 475                 480

Arg Thr Pro Glu Val Thr Cys Val Val Val Asp Val Ser His Glu Asp
                485                 490                 495

Pro Glu Val Lys Phe Asn Trp Tyr Val Asp Gly Val Glu Val His Asn
            500                 505                 510

Ala Lys Thr Lys Pro Arg Glu Glu Gln Tyr Asn Ser Thr Tyr Arg Val
        515                 520                 525

Val Ser Val Leu Thr Val Leu His Gln Asp Trp Leu Asn Gly Lys Glu
    530                 535                 540

Tyr Lys Cys Lys Val Ser Asn Lys Ala Leu Pro Ala Pro Ile Ala Lys
545                 550                 555                 560

Thr Ile Ser Lys Ala Lys Gly Gln Pro Arg Glu Pro Gln Val Tyr Thr
                565                 570                 575

Leu Pro Pro Ser Arg Glu Glu Met Thr Lys Asn Gln Val Ser Leu Thr
            580                 585                 590

Cys Leu Val Lys Gly Phe Tyr Pro Ser Asp Ile Ala Val Glu Trp Glu
        595                 600                 605

Ser Asn Gly Gln Pro Glu Asn Asn Tyr Lys Thr Thr Pro Pro Val Leu
    610                 615                 620

Asp Ser Asp Gly Ser Phe Phe Leu Tyr Ser Lys Leu Thr Val Asp Lys
625                 630                 635                 640

Ser Arg Trp Gln Gln Gly Asn Val Phe Ser Cys Ser Val Met His Glu
                645                 650                 655

Ala Leu His Asn His Tyr Thr Gln Lys Ser Leu Ser Leu Ser Pro Gly
            660                 665                 670

Lys

<210> SEQ ID NO 13
<211> LENGTH: 1307
<212> TYPE: DNA
<213> ORGANISM: Artificial Sequence
<220> FEATURE:
<223> OTHER INFORMATION: Synthetic Construct

<400> SEQUENCE: 13
aagcttgaat tcgccaccat ggtctcccag gccctcaggc tcctctgcct tctgcttggg    60
cttcagggct gcctggctgc agtcttcgta acccaggagg aagcccacgg cgtcctgcac   120
cggcgccggc gcgccaacgc gttcctggag gagctgcggc cgggctccct ggagagggag   180
tgcaaggagg agcagtgctc cttcgaggag gcccgggaga tcttcaagga cgcggagagg   240
acgaagctgt tctggatttc ttacagtgat ggtgaccagt gtgcctcaag tccatgccag   300
aatgggggct cctgcaagga ccagctccag tcctatatct gcttctgcct ccctgccttc   360
gagggccgga actgtgagac gcacaaggat gaccagctga tctgtgtgaa cgagaacggc   420
ggctgtgagc agtactgcag tgaccacacg ggcaccaagc gctcctgtcg gtgccacgag   480
gggtactctc tgctggcaga cggggtgtcc tgcacaccca cagttgaata tccatgtgga   540
aaaataccta ttctagaaaa aagaaatgcc agcaagcccc aagggcgagg atccgcagag   600

```
cccaaatctt gtgacaaaac tcacacatgc ccaccgtgcc cagcacctga actcctgggg    660
ggaccgtcag tcttcctctt ccccccaaaa cccaaggaca ccctcatgat ctcccggacc    720
cctgaggtca catgcgtggt ggtggacgtg agccacgaag accctgaggt caagttcaac    780
tggtacgtgg acggcgtgga ggtgcataat gccaagacaa agccgcggga ggagcagtac    840
aacagcacgt accgtgtggt cagcgtcctc accgtcctgc accaggactg gctgaatggc    900
aaggagtaca agtgcaaggt ctccaacaaa gccctcccag cccccatcga aaaaccatc    960 tccaaagcca aagggcagcc ccgagaacca caggtgtaca ccctgccccc atcccgggat   1020
gagctgacca agaaccaggt cagcctgacc tgcctggtca aaggcttcta tcccagcgac   1080
atcgccgtgg agtgggagag caatgggcag ccggagaaca actacaagac cacgcctccc   1140
gtgctggact ccgacggctc cttcttcctc tacagcaagc tcaccgtgga caagagcagg   1200
tggcagcagg ggaacgtctt ctcatgctcc gtgatgcatg aggctctgca caaccactac   1260
acgcagaaga gcctctccct gtctccgggt aaatgataag cggccgc                 1307
```

<210> SEQ ID NO 14
<211> LENGTH: 425
<212> TYPE: PRT
<213> ORGANISM: Artificial Sequence
<220> FEATURE:
<223> OTHER INFORMATION: Synthetic Construct

<400> SEQUENCE: 14

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Ser
            180                 185                 190

Ala Glu Pro Lys Ser Cys Asp Lys Thr His Thr Cys Pro Pro Cys Pro
        195                 200                 205

Ala Pro Glu Leu Leu Gly Gly Pro Ser Val Phe Leu Phe Pro Pro Lys
    210                 215                 220

Pro Lys Asp Thr Leu Met Ile Ser Arg Thr Pro Glu Val Thr Cys Val
225                 230                 235                 240
```

```
Val Val Asp Val Ser His Glu Asp Pro Glu Val Lys Phe Asn Trp Tyr
            245                 250                 255

Val Asp Gly Val Glu Val His Asn Ala Lys Thr Lys Pro Arg Glu Glu
        260                 265                 270

Gln Tyr Asn Ser Thr Tyr Arg Val Val Ser Val Leu Thr Val Leu His
    275                 280                 285

Gln Asp Trp Leu Asn Gly Lys Glu Tyr Lys Cys Lys Val Ser Asn Lys
290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Asp Glu Leu
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys
                420                 425

<210> SEQ ID NO 15
<211> LENGTH: 1289
<212> TYPE: DNA
<213> ORGANISM: Artificial Sequence
<220> FEATURE:
<223> OTHER INFORMATION: Synthetic Construct

<400> SEQUENCE: 15
aagcttgaat tcgccaccat ggtctcccag gccctcaggc tcctctgcct tctgcttggg      60
cttcagggct gcctggctgc agtcttcgta acccaggagg aagcccacgg cgtcctgcac     120
cggcgccggc gcgccaacgc gttcctggag gagctgcggc cgggctccct ggagagggag     180
tgcaaggagg agcagtgctc cttcgaggag gcccgggaga tcttcaagga cgcggagagg     240
acgaagctgt tctggatttc ttacagtgat ggtgaccagt gtgcctcaag tccatgccag     300
aatgggggct cctgcaagga ccagctccag tcctatatct gcttctgcct ccctgccttc     360
gagggccgga actgtgagac gcacaaggat gaccagctga tctgtgtgaa cgagaacggc     420
ggctgtgagc agtactgcag tgaccacacg ggcaccaagc gctcctgtcg gtgccacgag     480
gggtactctc tgctggcaga cggggtgtcc tgcacaccca cagttgaata tccatgtgga     540
aaaataccta ttctagaaaa aagaaatgcc agcaagcccc aagggcgagg atccgacaaa     600
actcacacat gcccaccgtg cccagcacct gaactcctgg ggggaccgtc agtcttcctc     660
ttccccccaa acccaagga cacccctcatg atctcccgga cccctgaggt cacatgcgtg     720
gtggtggacg tgagccacga agaccctgag gtcaagttca actggtacgt ggacggcgtg     780
gaggtgcata atgccaagac aaagccgcgg gaggagcagt acaacagcac gtaccgtgtg     840
gtcagcgtcc tcaccgtcct gcaccaggac tggctgaatg gcaaggagta caagtgcaag     900
gtctccaaca agccctcccc agcccccatc gagaaaacca tctccaaagc caaagggcag     960
```

-continued

```
ccccgagaac cacaggtgta cgccctgccc ccatcccggg atgagctgac caagaaccag    1020
gtcagcctga cctgcctggt caaaggcttc tatcccagcg acatcgccgt ggagtgggag    1080
agcaatgggc agccggagaa caactacaag accacgcctc ccgtgctgga ctccgacggc    1140
tccttcttcc tctacagcaa gctcaccgtg gacaagagca ggtggcagca ggggaacgtc    1200
ttctcatgct ccgtgatgca tgaggctctg cacaaccact acacgcagaa gagcctctcc    1260
ctgtctccgg gtaaatgata agcggccgc                                      1289
```

<210> SEQ ID NO 16
<211> LENGTH: 419
<212> TYPE: PRT
<213> ORGANISM: Artificial Sequence
<220> FEATURE:
<223> OTHER INFORMATION: Synthetic Construct

<400> SEQUENCE: 16

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Gly Ser
            180                 185                 190

Asp Lys Thr His Thr Cys Pro Pro Cys Pro Ala Pro Glu Leu Leu Gly
        195                 200                 205

Gly Pro Ser Val Phe Leu Phe Pro Pro Lys Pro Lys Asp Thr Leu Met
    210                 215                 220

Ile Ser Arg Thr Pro Glu Val Thr Cys Val Val Val Asp Val Ser His
225                 230                 235                 240

Glu Asp Pro Glu Val Lys Phe Asn Trp Tyr Val Asp Gly Val Glu Val
                245                 250                 255

His Asn Ala Lys Thr Lys Pro Arg Glu Glu Gln Tyr Asn Ser Thr Tyr
            260                 265                 270

Arg Val Val Ser Val Leu Thr Val Leu His Gln Asp Trp Leu Asn Gly
        275                 280                 285

Lys Glu Tyr Lys Cys Lys Val Ser Asn Lys Ala Leu Pro Ala Pro Ile
    290                 295                 300
```

| | | | | | | | | | | | | | | |
|---|---|---|---|---|---|---|---|---|---|---|---|---|---|---|
| Glu | Lys | Thr | Ile | Ser | Lys | Ala | Lys | Gly | Gln | Pro | Arg | Glu | Pro | Gln | Val |
| 305 | | | | 310 | | | | | 315 | | | | | 320 |
| Tyr | Ala | Leu | Pro | Pro | Ser | Arg | Asp | Glu | Leu | Thr | Lys | Asn | Gln | Val | Ser |
| | | | 325 | | | | | 330 | | | | | 335 | |
| Leu | Thr | Cys | Leu | Val | Lys | Gly | Phe | Tyr | Pro | Ser | Asp | Ile | Ala | Val | Glu |
| | | 340 | | | | | 345 | | | | | 350 | | | |
| Trp | Glu | Ser | Asn | Gly | Gln | Pro | Glu | Asn | Asn | Tyr | Lys | Thr | Thr | Pro | Pro |
| | | 355 | | | | | 360 | | | | | 365 | | | |
| Val | Leu | Asp | Ser | Asp | Gly | Ser | Phe | Phe | Leu | Tyr | Ser | Lys | Leu | Thr | Val |
| | 370 | | | | | 375 | | | | | 380 | | | | |
| Asp | Lys | Ser | Arg | Trp | Gln | Gln | Gly | Asn | Val | Phe | Ser | Cys | Ser | Val | Met |
| 385 | | | | 390 | | | | | 395 | | | | | 400 | |
| His | Glu | Ala | Leu | His | Asn | His | Tyr | Thr | Gln | Lys | Ser | Leu | Ser | Leu | Ser |
| | | | 405 | | | | | 410 | | | | | 415 | | |
| Pro | Gly | Lys | | | | | | | | | | | | | |

<210> SEQ ID NO 17
<211> LENGTH: 1289
<212> TYPE: DNA
<213> ORGANISM: Artificial Sequence
<220> FEATURE:
<223> OTHER INFORMATION: Synthetic Construct

<400> SEQUENCE: 17

```
aagcttggat tcgccaccat ggtctcccag ccctcaggc tcctctgcct tctgcttggg      60
cttcagggct gctggctgc agtcttcgta acccaggagg aagcccacgg cgtcctgcac     120
cggcgccggc gcgccaacgc gttcctggag gagctgcggc cgggctccct ggagagggag    180
tgcaaggagg agcagtgctc cttcgaggag gcccgggaga tcttcaagga cgcggagagg    240
acgaagctgt tctggatttc ttacagtgat ggtgaccagt gtgcctcaag tccatgccag    300
aatgggggct cctgcaagga ccagctccag tcctatatct gcttctgcct ccctgccttc    360
gagggccgga actgtgagac gcacaaggat gaccagctga tctgtgtgaa cgagaacggc    420
ggctgtgagc agtactgcag tgaccacacg ggcaccaagc gctcctgtcg gtgccacgag    480
gggtactctc tgctggcaga cggggtgtcc tgcacaccca cagttgaata tccatgtgga    540
aaaataccta ttctagaaaa aagaaatgcc agcaagcccc aagggcgagg atccgacaaa    600
actcacacat gcccaccgtg cccagcacct gaactcctgg ggggaccgtc agtcttcctc    660
ttccccccaa acccaaggga caccctcatg atctcccgga cccctgaggt cacatgcgtg    720
gtggtggacg tgagccacga agaccctgag gtcaagttca actggtacgt ggacggcgtg    780
gaggtgcata atgccaagac aaagccgcgg gaggagcagt acaacagcac gtaccgtgtg    840
gtcagcgtcc tcaccgtcct gcaccaggac tggctgaatg gcaaggagta caagtgcaag    900
gtctccaaca agccctccc agccccatc gcgaaaacca tctccaaagc caaagggcag    960
ccccgagaac cacaggtgta caccctgccc ccatcccggg aggagatgac caagaaccag   1020
gtcagcctga cctgcctggt caaaggcttc tatcccagcg acatcgccgt ggagtgggag   1080
agcaatgggc agccggagaa caactacaag accacgcctc ccgtgctgga ctccgacggc   1140
tccttcttcc tctacagcaa gctcaccgtg gacaagagca ggtggcagca ggggaacgtc   1200
ttctcatgct ccgtgatgca tgaggctctg cacaaccact acacgcagaa gagcctctcc   1260
ctgtctccgg gtaaatgata agcggccgc                                      1289
```

<210> SEQ ID NO 18

```
<211> LENGTH: 418
<212> TYPE: PRT
<213> ORGANISM: Artificial Sequence
<220> FEATURE:
<223> OTHER INFORMATION: Synthetic Construct

<400> SEQUENCE: 18
```

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
130                 135                 140

Gly Thr Lys Arg Ser Cys Arg Cys His Glu Gly Tyr Ser Leu Leu Ala
145                 150                 155                 160

Gly Val Ser Cys Thr Pro Thr Val Glu Tyr Pro Cys Gly Lys Ile Pro
                165                 170                 175

Ile Leu Glu Lys Arg Asn Ala Ser Lys Pro Gln Gly Arg Gly Ser Asp
            180                 185                 190

Lys Thr His Thr Cys Pro Pro Cys Pro Ala Pro Glu Leu Leu Gly Gly
        195                 200                 205

Pro Ser Val Phe Leu Phe Pro Pro Lys Pro Lys Asp Thr Leu Met Ile
    210                 215                 220

Ser Arg Thr Pro Glu Val Thr Cys Val Val Val Asp Val Ser His Glu
225                 230                 235                 240

Asp Pro Glu Val Lys Phe Asn Trp Tyr Val Asp Gly Val Glu Val His
                245                 250                 255

Asn Ala Lys Thr Lys Pro Arg Glu Glu Gln Tyr Asn Ser Thr Tyr Arg
            260                 265                 270

Val Val Ser Val Leu Thr Val Leu His Gln Asp Trp Leu Asn Gly Lys
        275                 280                 285

Glu Tyr Lys Cys Lys Val Ser Asn Lys Ala Leu Pro Ala Pro Ile Ala
    290                 295                 300

Lys Thr Ile Ser Lys Ala Lys Gly Gln Pro Arg Glu Pro Gln Val Tyr
305                 310                 315                 320

Thr Leu Pro Pro Ser Arg Glu Glu Met Thr Lys Asn Gln Val Ser Leu
                325                 330                 335

Thr Cys Leu Val Lys Gly Phe Tyr Pro Ser Asp Ile Ala Val Glu Trp
            340                 345                 350

Glu Ser Asn Gly Gln Pro Glu Asn Asn Tyr Lys Thr Thr Pro Pro Val
        355                 360                 365

Leu Asp Ser Asp Gly Ser Phe Phe Leu Tyr Ser Lys Leu Thr Val Asp
    370                 375                 380

```
Lys Ser Arg Trp Gln Gln Gly Asn Val Phe Ser Cys Ser Val Met His
385                 390                 395                 400

Glu Ala Leu His Asn His Tyr Thr Gln Lys Ser Leu Ser Leu Ser Pro
                405                 410                 415

Gly Lys
```